US005552299A

United States Patent [19]

Ott et al.

[11] Patent Number: 5,552,299

[45] Date of Patent: Sep. 3, 1996

[54] PLASMIDS AND PROCESS FOR PRODUCING RECOMBINANT DESULPHATOHIRUDIN HV-1 PEPTIDES

[75] Inventors: István Ott; Tibor Klupp; István Molnár; András Patthy; István Barta; Zsuzsa Barkó née Tóth; Gábor Ambrus; János Salát; Anikó Tegdes; Imre Moravcsik; Cecilia Együd; Kárnly Albrecht; Kálmán Könczöl; Attila Vincze; Éva Barabás; György Máté, all of Budapest; György B. Kiss; Péter Kiss, both of Szeged; Kálmán Pólya, Debrecen; János Erdei, Debrecen; Éva Gulyás, Debrecen; Erika Zilahi, Debrecen, all of Hungary

[73] Assignee: Biogal Gyogyszergyar Rt., Budapest, Hungary

[21] Appl. No.: 44,506

[22] Filed: Apr. 9, 1993

[30] Foreign Application Priority Data

Apr. 9, 1992 [HU] Hungary ................................ 92-01200

[51] Int. Cl.$^6$ ............................ C12P 21/06; C12N 1/19; C12N 15/81

[52] U.S. Cl. .................. 435/69.1; 435/320.1; 435/255.2; 536/23.5; 536/24.1; 530/381

[58] Field of Search ............................ 435/172.1, 172.3, 435/69.1, 320.1, 255.2; 536/23.5, 24.1; 530/381

[56] References Cited

U.S. PATENT DOCUMENTS

| | | | |
|---|---|---|---|
| 5,089,398 | 2/1992 | Rosenburg et al. | 435/69.1 |
| 5,096,815 | 3/1992 | Ladner et al. | 435/69.1 |
| 5,162,208 | 11/1992 | Lemoine et al. | 435/69.1 |
| 5,182,195 | 1/1993 | Nakahama et al. | 435/69.1 |
| 5,268,296 | 12/1993 | Maschler et al. | 435/252.3 |

OTHER PUBLICATIONS

Bennetzen et al. 1982. J. Biol. Chem. 257(6):3026–3031.

Chen et al. 1988. Gene 69:181–192.

*Primary Examiner*—Robert A. Wax
*Assistant Examiner*—Keith D. Hendricks
*Attorney, Agent, or Firm*—Keil & Weinkauf

[57] ABSTRACT

The present invention relates to a process for producing recombinant desulphatohirudin by means of culturing microorganisms.

Concerning the codon usage of microorganisms the synthesized nucleotide sequences were joined downstream of and in reading frame with isolated promoters and signal sequences, subsequently the expression/secretion cassettes comprising the foregoing elements were inserted into plasmid DNAs allowing the cultivation of cells under selective culture conditions. *E. coli*, Saccharomyces and Streptomyces species were transformed with the said recombinant plasmids to biosynthesize the thrombin inhibitor desulphatohirudin HV-1 which was then isolated and identified.

The thus-produced desulphatohirudin can be used to inhibit blood coagulation.

11 Claims, 25 Drawing Sheets

```
       5'-CTGGCC ATG GTT GTT TAC ACC GAC TGT ACC GAA TCT GGT
                     I. fragment

       3'-CATGGACCGG TAC CAA CAA ATG TGG CTG ACA TGG CTT AGA CCA
                     MET Val Val Tyr Thr Asp Cys Thr Glu Ser Gly
                     II. fragment

CAA AAC TTG TGT TTA TGT GAA G GT TCT AAC GTC TGC GGT CAG�↓GGT
GTT TTG AAC ACA AAT ACA CTT C CA AGA TTG CAG ACG CCA GTC CCA
Gln Asn Leu Cys Leu Cys Glu G↑ly Ser Asn Val Cys Gly Gln Gly
                     III. fragment

AAC AAG TGT ATC TTG GGT TCT RAC GGT GAA AAA AAT CAA TGT GTC
TTG TTC ACA TAG AAC CCA AGA ZTC CCA CTT TTT TTA GTT ACA CAG
Asn Lys Cys Ile Leu Gly Ser Asx Gly Glu Lys Asn Gln Cys Val
                     IV. fragment

ACT GGC GAA GGT ACT C CA AAG CCA CAA TCC↓CAC AAC GAT GGT GAC
TGA CCG CTT CCA TGA G GT TTC GGT GTT AGG GTG TTG CTA CCA CTG
Thr Gly Glu Gly Thr P↑ro Lys Pro Gln Ser His Asn Asp Gly Asp
                     V. fragment

TTC GAG GAA ATT CCT GAA GAA TAC CTA CAA TAG TAA GCA TG
AAG CTC CTT TAA GGA CTT CTT ATG GAT GTT ATC ATT C
Phe Glu Glu Ile Pro Glu Glu Tyr Leu Gln TER TER
                     VI. fragment
```

FIG. 1a

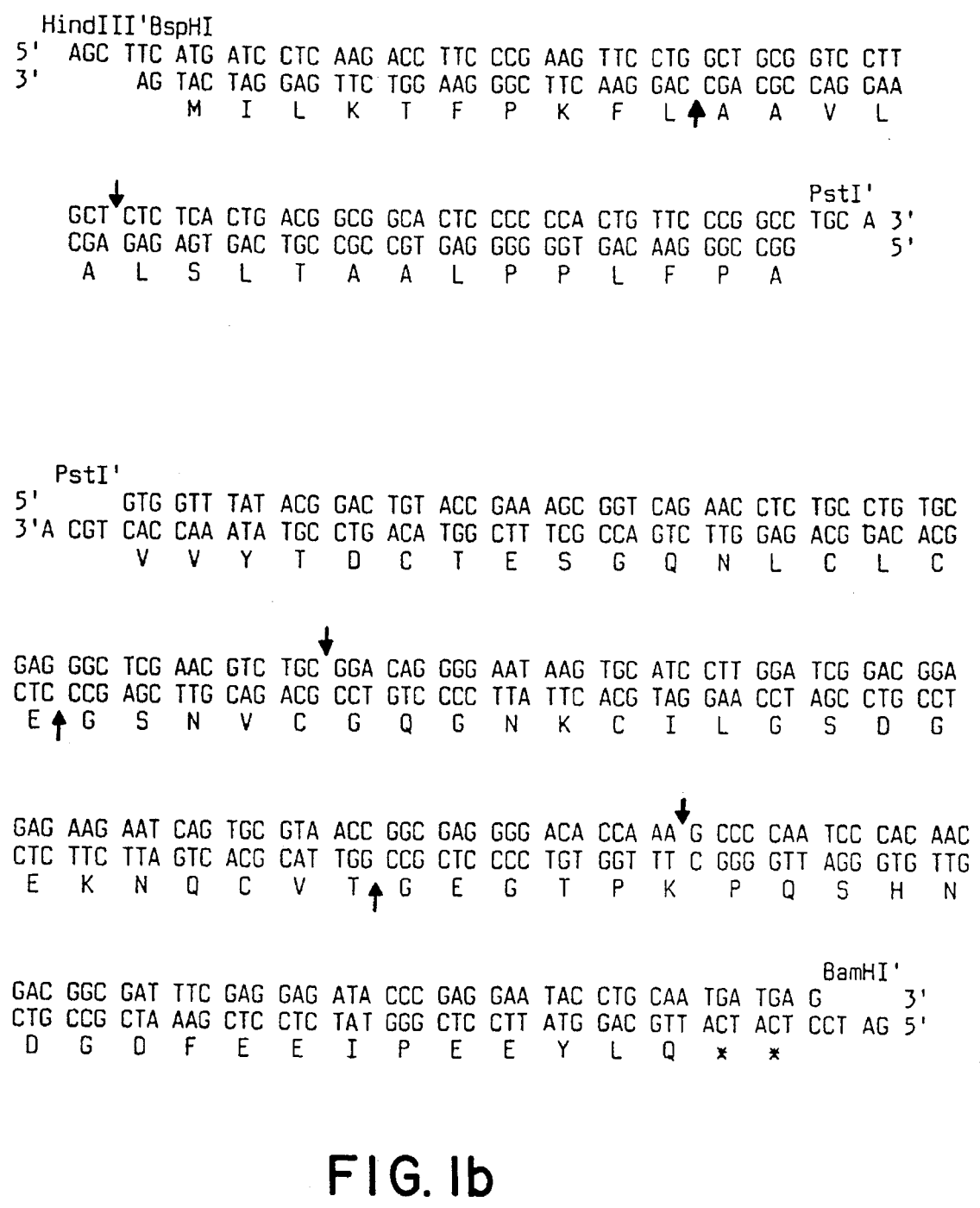

```
       HindIII'BspHI
5' AGC TTC ATG ATC CTC AAG ACC TTC CCG AAG TTC CTG GCT GCG GTC CTT
3'         AG TAC TAG GAG TTC TGG AAG GGC TTC AAG GAC CGA CGC CAG GAA
              M   I   L   K   T   F   P   K   F   L↑A   A   V   L

         ↓                                                    PstI'
   GCT CTC TCA CTG ACG GCG GCA CTC CCC CCA CTG TTC CCG GCC TGC A 3'
   CGA GAG AGT GAC TGC CGC CGT GAG GGG GGT GAC AAG GGC CGG       5'
    A   L   S   L   T   A   A   L   P   P   L   F   P   A

      PstI'
5'     GTG GTT TAT ACG GAC TGT ACC GAA AGC GGT CAG AAC CTC TGC CTG TGC
3'A CGT CAC CAA ATA TGC CTG ACA TGG CTT TCG CCA GTC TTG GAG ACG GAC ACG
        V   V   Y   T   D   C   T   E   S   G   Q   N   L   C   L   C

                            ↓
GAG GGC TCG AAC GTC TGC GGA CAG GGG AAT AAG TGC ATC CTT GGA TCG GAC GGA
CTC CCG AGC TTG CAG ACG CCT GTC CCC TTA TTC ACG TAG GAA CCT AGC CTG CCT
 E↑G   S   N   V   C   G   Q   G   N   K   C   I   L   G   S   D   G

                                                ↓
GAG AAG AAT CAG TGC GTA ACC GGC GAG GGG ACA CCA AA G CCC CAA TCC CAC AAC
CTC TTC TTA GTC ACG CAT TGG CCG CTC CCC TGT GGT TT C GGG GTT AGG GTG TTG
 E   K   N   Q   C   V   T↑G   E   G   T   P   K   P   Q   S   H   N

                                                            BamHI'
GAC GGC GAT TTC GAG GAG ATA CCC GAG GAA TAC CTG CAA TGA TGA G      3'
CTG CCG CTA AAG CTC CTC TAT GGG CTC CTT ATG GAC GTT ACT ACT CCT AG 5'
 D   G   D   F   E   E   I   P   E   E   Y   L   Q   *   *
```

FIG. 1b

```
 STRUCTURE OF H16
=====================

                                    Hind III
                                     /----/
                              5' ... AAGCTTCGCGCCGCATGAGGGGCTGAAGAAAAAAATCTC

   "-35"                    "-10"          TI
   ------                   ------         -
TCGATTGACAAATTCATGCAATCGAATTTACAATGATCTTGTAGAAAATCAACATAAGGGCCATGCATTT
   ------------------------------          --------------------------
           PR                                       5'NT

TTTAGACCGATATCGTTATCGGTTTGGAAAACAACCCCGGTATCTCTTAGGAGACGCCGGGGTTGTTCGC
----------------------------------------------------------------------
                              5'NT

TTTAAAGGGGGTGATCCATCGGAAGCCGGATCAAACGACAAAATGTAAGCGTTTCATTTTTTTCACAGAC
----------------------------------------------------------------------
                              5'NT

         "SD"
        ------
ACTTAGGAAGCAGGAGGACATGATATTGAAAACATTCCCGAAATTTCTTGCAGCCGTTCTTGCATTGTCG
------------------- M  I  L  K  T  F  P  K  F  L  A  A  V  L  A  L  S
     5'NT                                 SP

                                                       HIR
                                    V  V  Y  T  D  C  T  E  S  G  Q  N
CTGACCGCAGCCCTGCCCCCGCTTTTGCCGGCGGTTGTTTACACCGACTGTACCGAATCTGGTCAAAACT
 L  T  A  A  L  P  P  L  L  P  A

                                    HIR
L  C  L  C  E  G  S  N  V  C  G  Q  G  N  K  C  I  L  G  S  D  G  E  K
TGTGTTTATGTGAAGGTTCTAACGTCTGCGGTCAGGGTAACAAGTGTATCTTGGGTTCTGACGGTGAAAA

                                    HIR
 N  Q  C  V  T  G  E  G  T  P  K  P  Q  S  H  N  D  G  D  F  E  E  I
AAATCAATGTGTCACTGGCGAAGGTACTCCAAAGCCACAATCCCACAACGATGGTGACTTCGAGGAAATT

    HIR
 P  E  E  Y  L  Q
CCTGAAGAATACCTACAATAGTAAGCATGCAAGCTTGG ... 3'
                              /----//----/
                              Sph I Hind III
```

FIG. 7

PLASMIDS AND PROCESS FOR PRODUCING RECOMBINANT DESULPHATOHIRUDIN HV-1 PEPTIDES

The present invention relates to novel plasmids and processes for production recombinant desulphatohirudin HV-1 peptides. More particularly, the invention concerns a method for the production of nucleotide sequences determining the amino acid sequences of desulphatohirudin HV-1 33 (ASP) and HV-1 33 (ASN) variants (at the 33 position asparagine or aspartic acid), to clone the aforesaid DNA sequences into expression/secretion vector DNAs, to transform the said vector DNAs into microorganisms, to select the cells having the desired DNA sequences and to culture and isolate the foregoing cells.

Furthermore, the invention relates to the nucleotide sequences encoding hirudin HV-1, the regulatory nucleotide sequences necessary to express hirudin and the novel plasmid DNAs comprising the aforesaid sequences.

Hirudin is produced in the salivary glands of the leech (*Hirudo medicinalis*). It is a polypeptide of 65 amino acid residues and comprises three disulphide bridges. Hirudin is the most potent inhibitor of blood coagulation known up to the present, its function is accomplished through the specific inhibition of thrombin which is one of the proteolytic enzymes of the blood-clotting cascade. Function and structure of hirudins (HV-1, HV-2 and PA in the literature) produced in leech have been well known for a long time, hirudins have been produced from the body of leech and also by recombinant techniques. Recombinant hirudins are the desulphato variants of the natural hirudins since microorganisms are not able to sulphate tyrosine at the 63 position. The blood-clotting inhibitory effect of desulphatohirudin and its dissociation constant in the thrombinhirudin complex are almost the same as those of the sulphated hirudin.

For the sake of simplicity desulphatohirudin produced by recombinant techniques will be called as hirudin in this description. Hirudin as the selective inhibitor of thrombin blocks not only the thrombin but the activation of V, VIII and XIII blood clotting factors and the platelet reaction, too. Its application can be particularly preferred in thromboembolical diseases, for the blocking of arterial thrombosis and prevention of venous thrombosis, in disseminated intravascular coagulation, in extracorporeal circulation, in the condition of antithrombin III deficiency, in prevention of reocclusion during thrombolysis by fibrinolytic agents, in heart operation and in hemodialysis.

In the basic and applied research laboratories the number of pharmacologically active peptides and proteins produced by recombinant DNA technology is continuously increasing. To produce hirudin—the anticoagulant agent of Hirudo medicinalis—experiments have been achieved by recombinant techniques since 1984.

Hirudins, similarly to other peptides, can be efficiently produced by recombinant techniques using microorganisms with known genetics and providing the desired structural gene and regulatory nucleotide sequences of transcription and translation to biosynthesize the target compound. In general, the expression/secretion systems can be introduced into the cells in some kind of carrier DNA molecules such as plasmids.

Hirudin was first produced microbiologically in *Escherichia coli* cells.

According to the European patent specification No. 158,564 recombinant hirudin was biosynthesized by *E. coli* cells, using pTG vectors constructed from pBR322 plasmid to the expression. The PL promoter of lambda phage was used as promoter. The fermentation broth produced by this process contained 10–15 units/ml of hirudin (1 mg hirudin equals 13,000–15,000 units). The active material accumulated in the cells, therefore for separating it the cells had to be lysed. The antithrombin activity of hirudins in the cultures was not exactly identified.

The authors of the published German patent application No. 3,445,517 employed expression systems comprising lac, β-lactamase, trp and lipoprotein promoters to produce recombinant hirudin. The biosynthesized hirudin produced by their expression system based on EMBL8 plasmid remained in the intracellular space, therefore the cells had to be lysed. Cultures having 1–2 units/liter of hirudin activity can be obtained by their process. It is questionable, however, which component of the hirudin is responsible for the activity since the product was not identified.

The European patent specification No. 258,118 discloses the production of γ-interferon, antitrypsin and hirudin by means of *E. coli* cells, essentially with the pTG vector series employing the expression system given in the European patent specification No. 158,564, with the difference that the plasmids were stabilized by inserting DAP (diaminopimelic acid) gene. The 10–20 units/ml of thrombin-blocking activity of the obtained culture broth was not identified.

According to the European patent specification No. 356,335 the authors produced hirudin HV-2 in concentrations of 13–45 units/ml by means of culturing *E. coli* cells employing signal sequences suitable to secrete the product into the periplasmatic space, where it could be isolated by osmotic shock. The active agent responsible for the hirudin-like activity was not identified by convincing data.

The authors of the European patent specification No. 448,093 disclosed the production of hirudin analogs under the control of a trp-lac fusion promoter employing the alpha-cyclodextringlycosyl transferase signal sequence. During the fermentation the hirudin biosynthesis was induced by isopropyl-β-D-thiogalactoside (IPTG). The hirudin activity appearing in the culture broth was measured by biological methods. Isolation and structural determination of the product were not reported.

According to the European patent specification No. 168,342 (it corresponds to the Hungarian patent specification No. 202,288) hirudin HV-1 was produced using the derivatives of the known pBR322 plasmid DNA, under the control of tryptophan (trp) operon. Here the target compound remained in the *E. coli* cells, therefore the cells had to be lysed to isolate 3–6 units/ml of biosynthesized hirudin from the culture. The product was characterized only by N- and C-terminal amino acid analysis.

Hirudins can be produced in the form of fusion proteins, too. In this case the hirudin is produced together with an other protein, and the fusion protein accumulates in the cytoplasm in the form of a so-called inclusion body. The advantage of this method is that the heterologous protein being optionally formed in high amounts and in precipitated form does not poison the cells and it can be easily prepared from the lysed cells. The hirudin can be extracted from the fusion product by enzymatical or chemical methods.

The authors of the European patent specification No. 171,024 expressed hirudins by synthetically produced nucleotide sequences using known *E. coli* plasmids (pUC12, pKK177.3, pAT153). Under the regulation of Lac UV5 promoter after induction with IPTG, the active agent responsible for the hirudin activity was prepared by lysing the cells and cleaving the fusion product by cyanogen bromide. From the undetailed description it does not turn out whether the obtained product has the sequence of hirudin and, if any, in what amount it has been synthesized.

According to the German patent specification No. 3,526, 995, under the transcriptional control of tac promoter, by means of IPTG induction and *E. coli* cells, fusion proteins could be produced by utilizing regions of the trp structural gene and hirudin or proinsulin nucleotide sequences located in vector DNA. The description does not contain data about the isolation and identification of the product.

In the German patent specification No. 3,541,856 the production of fusion proteins containing interleukin-2 and hirudin analogs employing the lac repressor gene was disclosed. The reproducibility and efficiency of the process can not be inferred from this patent because of the lacking data about the isolation and identification of the product.

The German patent specification No. 3,636,903 discloses the production of interleukin-2, colony stimulating factor and hirudin fusion proteins by means of *E. coli* cells under the regulation of lac and tac promoters. The existence of product was confirmed with western-blotting using proper antibodies. Because of the missing data the efficiency and applicability of the process can not be stated.

The authors of the European patent specification No. 286,956 set an aim to produce fusion proteins from β-galactosidase, proinsulin, interleukin, calcitonin and hirudin peptides by using *E. coli* cells, pUC, pBR and pW types plasmids and lac promoter. They have described neither details of the procedure nor examples of production.

The published PTC application No. WO 90/13560 concerns the production of fusion proteins comprising for example tissue-activating peptide and hirudin or laminin B1. In the process *E. coli* cells and $pNP_6$ plasmid are used.

According to the published PTC application No. WO 90/13647 the aforesaid $pNP_6$ plasmid, E1 colicin promoter and lex a operator region are employed to produce among others fusion proteins containing hirudin by means of *E. coli* cells. According to HPLC analysis, using known methods, the purity of hirudin was 95% but neither the efficiency data of production nor the quantity of hirudin in the cultures are disclosed.

In the German patent specification No. 3,942,580 the production of protein A—hirudin fusion protein is disclosed by means of *E. coli* N.4830-1 strain using pRIT and pPRIT plasmids known in the literature.

The authors of the European patent specification No. 412,526 produced porcine adenylate kinase—hirudin fusion protein employing *E. coli* cells. To construct the expression vectors they utilize trp promoter building into the said vector.

One of the favorite object of genetic engineering is the Saccharomyces. The genetics and biochemistry of yeast are relatively well known, their expression/secretion systems have been quickly developed. Production of hirudin can be favourably accomplished by Saccharomyces cells.

In the European patent specification No. 168,342 (it corresponds to the Hungarian patent specification No. 202, 288) a process to produce hirudin is disclosed in which the HV-1 analog is biosynthesized by *Saccharomyces cerevisiae* under the control of PHO5 promoter. The expressed product is not secreted into the culture broth, therefore the cells had to be lysed to prepare the product. The amount of the produced hirudin can not be deduced from the description and the supposed structure thereof has not satisfactorily been proved.

In the published PCT application No. WO 86/01224 a process is disclosed by the aid of which cultures with 10–15 units/ml of hirudin activity were obtained by means of *Saccharomyces cerevisiae* cells employing the pTG plasmid series (comprising pheromone promoter), although the product has not been identified.

The authors of the French patent specification No. 2,607, 517 (corresponds to the Hungarian patent specification No. 202,919) produced hirudin HV-2 variant employing the members of pTG plasmid series. In the expressional bifunctional plasmid the hirudin gene was expressed by means of pheromone promoter and PGK terminator region. The signal sequence of α-sexpheromone was employed to secrete the product into the intercellular space. The plasmid comprises the *E. coli* sequence of pBR322 as well as URA3 and leu2-d genes. With this process 20 units/ml of hirudin activity were produced in cultures and the active agent was determined by polyacrylamide gel electrophoresis.

The European patent specification No. 225,633 discloses the production of hirudin variants by means of cultivating *Saccharomyces cerevisiae* cells. The promoter sequences of GAPDH and PHO5 genes, furthermore the hybrids of them and trp sequences were employed. The secretion of the product was directed by PHO5 or invertase signal peptide sequences into the intracellular space. The terminator region of PHO5 gene was used as transcription terminator while LEU2 gene was employed as selection marker. The total amino acid sequence of the product was not determined.

The authors of the European patent specification No. 252,854 have further developed the pTG expression plasmids known from the French patent specification No. 2,607, 517. According to this method 4–9 units/ml hirudin activity were received in the cultures of *Saccharomyces cerevisiae* strain. The active compound was not identified and its structure was not analyzed.

The authors of the European patent specification No. 340,170 cultivated *Saccharomyces cerevisiae* cells to produce hirudins employing plasmids which comprised the total two-micron sequence. They used PHO5 sequence for signal sequence and GAPDH or PHO5 sequences for promoter. One of the hirudins isolated from the culture broth was identical with HV-1, the others were damaged on their C-terminal.

According to the European patent specification No. 341, 215 hirudins are produced by *Saccharomyces cerevisiae* strains having no carboxypeptidase activity. The essence of this process is that the DNA constructions disclosed in the aforesaid European patent specification No. 340,170 are expressed in Saccharomyces strain producing no ysc peptidase. The authors prove by reversed-phase HPLC that the formation of C-terminally damaged hirudins can be suppressed. No information is given about the isolation and identification of the product.

The authors of the European patent specification No. 390,676 were engaged in selecting *Saccharomyces cerevisiae* strain which was damaged in its proteolytic function. With this strain hirudin HV-2 was produced the proteolytic degradation of which could be decreased by this method.

According to the published PCT application No. WO 90/13646 DNA sequences encoding signal peptides were inserted into plasmids which were disclosed above. *Saccharomyces cerevisiae* cell cultures having the said plasmid produced 40–130 units/ml of hirudin activity. The hirudin HV-2 was identified by HPLC analysis and N-terminal amino acid analysis.

The published PCT application No. WO 91/09125 discloses among others the production of hirudin and fusion proteins comprising hirudin by means of *Saccharomyces cerevisiae* cells. The pSW6 expression vector employed in the process comprises LEU2 gene, α-factor prepro-peptide gene, gal and PGK promoters as well as PGK terminator region. Using this process cultures showing 100–150 units/ml of hirudin activity were obtained.

According to the European patent specification No. 435, 776 hirudin HV-2 was expressed in *Saccharomyces cerevisiae* cells employing artificially constructed GAL7 and ADH2 promoters. The amount of the produced and unidentified hirudin was 5 units/mi.

The authors of the European patent specification No. 396,436 have further developed the expression of hirudin HV-2 by *Saccharomyces cerevisiae* cells by inserting the gene encoding for yscF protease into the genome of yeast or into expression plasmid. The concentration of hirudin HV-2 in units/A600 (absorbance of the cultures at 600 nm) was 23–74. The product was not identified.

The authors of European patent specification No. 273,800 used Saccharomyces plasmid vectors, described formerly, for the construction of HV-2 variants. The same aim was set by the European patent specifications Nos. 324,712 and 332,523.

Experiments for hirudin expression are known not only with *E. coli* and Saccharomyces cells but also by means of *Bacillus subtilis* (European patent specification No. 402, 159) and *Bacillus amyloliquefaciens* (European patent specification No. 402,159), insects [L. Benatti et al., Gene 101, 255–260 (1991)] and mammalian cells (French patent specification No. 2,611,723). HV-1 modified in amino acid sequence was produced by means of Bacillus cells, with the aid of synthetic secretion sequence and under the transcriptional regulation of the neutral protease promoter.

There was only one experiment in which hirudin expression was accomplished in Streptomyces cells [E. Bender et al., Appl. Microbiol. Biotechnol. 34, 203–207 (1990)]. Using the signal sequence of tendamistat amylase inhibitor and a fusion promoter the authors attempted the expression of synthetic hirudin structural gene based on *E. coli* codon usage. Although in their culture media hirudin-like molecules were detected by immunoblotting, their hirudin activities were only twentieth of the hirudin standard. On the basis of this finding they concluded that the synthesized and secreted agent was a terminally degraded hirudin-like peptide.

From the above summary of the present state of the art it appears that many teams are intensively engaged in producing hirudin HV-1 and HV-2 and variants thereof. To the expression and secretion of the target compound DNA vectors and regulatory sequences are used.

It can be concluded that the level of expression is low in most cases, even in the most expediently developed process. All the more, the same conclusion can be drawn because the authors use methods to determine the amount of hirudin measuring not only the target compound but also molecules damaged in their N- or C-terminal (the aforesaid can also block the thrombin). Since in most patent specifications the expressed compound is not isolated in pure form, data concerning the yield are not published, the amino acid sequence of the product is not analyzed and the pure product is not characterized, respectively. Therefore it is not actually possible to state the concentration of hirudin in the cultures, that is the effectiveness of the expression and secretion systems.

On the basis of the available data the efficiency of most known procedures can be compared neither with each other nor with a novel process, and even the occasional reproduction of these processes may ran into difficulties since in some cases the descriptions are perfunctory, not to mention the accessibility of starter strains and DNA.

The purpose of the present invention is to ensure a novel process for the production of two hirudin forms: variants HV-1 33 ASP and HV-1 33ASN by recombinant technology.

The invention is based on the recognition that under the control of α-amylase promoter and a signal sequence isolated from the chromosomal DNA of *Bacillus circulans* (their sequences have been determined) stable hirudin production can be achieved by means of *E. coli* cells.

Similarly, large amounts of hirudin can be achieved in *E. coli* cells using our artificial operon constructed in vitro on a single messenger RNA determining the translation of two peptides.

We have succeeded in producing hirudin-delated β-galactosidase fusion protein under the transcriptional regulation of λ-phage PR promoter.

We have succeeded in producing hirudin HV-1 in the fermentation broth of Saccharomyces cells under the translational regulation of a new pX promoter identified by us, and under the control of UAS transcription activating sequence, applying initiating and terminating codons, using a signal peptide and amino acid sequence to ensure a cleavage site for endopeptidase, employing expression/secretion cassettes determining the level of expression in DNA plasmids comprising URA3 and leu2-d genes determining the stability in strains having reg1 and gal1 mutations.

By the utilization of URA3 and leu2-d genes we have succeeded in regulating the copy number and on this basis the production of hirudin and the plasmid stability, respectively. Particularly good fermentation technology can be achieved by galactose-inducible UAS region in strains having reg1 mutation—in the presence of this mutation the UAS region is unrepressible—and gal1 mutation blocking the consumption of galactose inducer from the fermentation broth. We could overcome the difficulties emerging in the scale-up process and the stability of plasmid in Saccharomyces bayanus. Stable hirudin HV-1 .expression and secretion have been for the first time achieved by means of Streptomyces cells known from industrial fermentation employing new expression/secretion DNA vectors comprising synthetic nucleotide sequences designed on the basis of Streptomyces codon usage.

According to the process of the invention reproducible hirudin HV-1 production suitable for scale up has been accomplished by means of *Escherichia coli*, Saccharomyces and Streptomyces strains, the highest hirudin HV-1 production level being at about 140–180 mg/liter of culture. The hirudin HV-1 peptide has been isolated in pure form and its total amino acid sequence has been determined.

Based on the above the invention relates to a process for producing desulphatohirudin HV-1 33ASP and desulphatohirudin HV-1 33 ASN peptides comprising the steps of biosynthesizing the said hirudin HV-1 peptides by expressing the nucleotid sequences coding for the hirudin HV-1 peptides synthesized in vitro on the basis of the codon usage of microorganisms a) under the control of nucleotide sequences of a promoter derived from *Bacillus circulans* α-amylase gene and signal sequence in *E. coli*, or b) under the control of PR promoter locating on the right arm of λ-phage, from one operon, translating the two amino acid sequences successively and independently from a single messenger RNA, or as a fusion protein in *E. coli* cells, or c) under the control of pX promoter, UAS transcription activating sequence, initiation and termination codons, employing the synthetic nucleotide sequence:

. . . 5'-TCA TTC GTT CAA GGT GTA TCT TTG GAT AAG AGA-3' (this sequence coding for signal peptide and an amino acid sequence to ensure the secretion and a cleavage site for endopeptidase), using the URA3 and leu2-d genes to determine the level of expression and stability of plasmid vector DNAs, applying expression/secretion cassettes in the aforesaid plasmids, by means of *Saccharomyces bayanus* and *Saccharomyces cerevisiae* cells, or d) under the control of promoter, signal and regulatory nucleotide sequences of *Bacillus circulans* α-amylase gene or under the control of the promoter of neomycin R gene derived from Streptomyces and an in vitro synthesized signal sequence, in expression/secretion DNA vectors suitable to replicate in Streptomyces cells, by cultivating the foregoing microorganisms under proper fermentation conditions after transformation of plasmids comprising the aforesaid elements, then separating the hirudins accumulated extracellularly or produced in the form of fusion proteins.

In the Examples we disclose the production of the two forms of hirudin HV-1 (HV-1 33ASP and HV-1 33ASN) by means of *E. coli*, Saccharomyces and Streptomyces microorganisms.

The employed expression/secretion systems and the nucleotide sequences encoding the structural gene designed on the basis of the codon usage of said microorganisms are new.

The fragments of nucleotide sequences being competent with the used microorganisms and determining the amino acid sequences of hirudin HV-1s, coding for the necessary restriction sites and for the stop codons, were synthesized in the way as described in Example 1.

FIGS. 1*a* and 1*b* show the amino acid and nucleotide sequences of hirudin HV-1s; aspartic acid and asparagine in the 33 position are marked by Asx, R means adenine or guanine, Z means cytosine or thymine.

FIG. 2 shows the insertion of the structural gene verified by nucleotide sequence analysis into pUC19 plasmid (New England Biolabs. Inc., Canada); accession numbers are: *E. coli* JM 109 (pUC19::H207 Asp) [NCAIM (P)B 1171] and (pUC19::H221 Asn) [NCAIM P(B) 1175].

Thereafter, to express hirudin the said sequences were ligated into expression/secretion DNA vectors of *E. coli*, Saccharomyces and Streptomyces operably linked to the regulatory sequences.

To express the structural gene designed on the basis of *E. coli* codon usage total DNA was prepared from *Bacillus circulans* [GYOKb-243, accession number/NCAIM (P)B 1159/] according to the method of Example 2, subsequently DNA gene bank was produced using the pGY97 phasmid [*E. coli* pGY97,/NCAIM P(B) 358/] (see also Hungarian patent specification No. 204,892).

FIG. 3 is the schematic representation of pGY97 phasmid vector. Following the in vitro phage packaging the promoter of *Bacillus circulans* α-amylase structural gene and its signal sequence were identified on the pGYOKI plasmid.

FIG. 4 shows the appearance of phage plaque carrying the α-amylase gene in *E. coli* cells.

FIGS. 5 and 6 are the schematic representations of the procedures used for recloning and converting the hirudin structural gene.

FIG. 7 shows the nucleotide sequence of the expression/secretion cassette named H16.

FIGS. 8, 9 and 10 show the position of α-amylase promoter and signal sequence joined in reading frame to the synthetic sequence of hirudin in pUC19 or in pUN121, respectively [*E. coli* GY 1095 (pUN121)/NCAIM (P)B 1163/and *E. coli* 1095/NCAIM P(B) 1162/]. *E. coli* cells were transformed with plasmids comprising the amylase-hirudin (H16) expression/secretion cassettes, then the transformants were selected on plates containing ampicillin or oxytetracycline. The production of hirudin was determined by the methods fully detailed in the Examples, then the strains having stable and high hirudin activity were chosen for laboratory fermentation [the strains were deposited under the name *E. coli* JM109 (pUC19::H16 and pUN121::H16)/NCAIM P(B) 1170 and NCAIM P(B) 1176/]. Peptides having hirudin activity were prepared, purified and identified by HPLC and by amino acid sequencing as desulphatohirudin HV-1.

An artificial operon was constructed to produce hirudin in *E. coli.* The structural gene encoding hirudin was inserted into M13mp18 phage (New England Biolabs. Inc., Canada) according to Example 4, then it was inserted into pEX1 plasmid (Boehringer Mannheim Biochemica GmbH.) to the C terminal end of β-galactosidase structural gene (see FIG. 10). In this construction the β-galactosidase is transcribed from the PR promoter of λ-phage, while the hirudin from the promoter of α-amylase gene. A fragment was cleaved from the nucleotide sequence of β-galactosidase by EcoRV digestion. This fragment comprises the C-terminal end of β-galactosidase sequence and the amylase promoter. The remainder sequence comprises the N-terminal end of β-galactosidase, the non-translating sequence (NT) of *Bacillus circulans* α-amylase, the hirudin structural gene (Hir), the ribosome binding site (SD) located upstream of Hir and the artificial operon directed by the heat-inducible promoters of the λ-phage. This operon transcribes only one mRNA, but during the translation hirudin and a deleted β-galactosidase are biosynthesized. The hirudin HV-1 was isolated and purified using the methods given in the Examples from heat-induced *E. coli* culture transformed by the aforesaid constructions. Furthermore, the hirudin was identified by HPLC analysis and/or amino acid sequencing. The foregoing *E. coli* pop 2136 (pEXl::H16 deltaEcoRV) strain was deposited [accession number: NCAIM (P)B 1165].

To construct the β-galactosidase-hirudin fusion protein according to the method described in Example 5, hirudin structural gene was isolated, then subcloned in M13mp18 and Bluescript (Stratagene) vectors (FIG. 11) and inserted into pEX1 plasmid in reading frame to a site immediately after the nucleotide sequence encoding the C-terminal of β-galactosidase (FIG. 12). The thus-obtained fusion protein was biosynthesized under the transcriptional control of the heat inducible, strong PR promoter of λ-phage. To increase the amount of the hirudin produced in *E. coli* pop 2136 [NCAIM (P)B 1161] cells under the control of cI ts 857 temperature sensitive repressor, the nucleotide sequence of β-galactosidase was deleted by PvuII, SmaI and EcoRV restriction enzymes. The foregoing constructions were transformed in *E. coli* pop 2136 strain, the cells were heat induced and the product was analyzed by polyacrylamide gel electrophoresis. According to this analysis the aforesaid fusion proteins were as long as expected. After cleavage by cyanogen bromide the hirudin HV-1 was released and analyzed by HPLC and amino-acid sequencing.

The accession numbers of the *E. coli* pop 2136 (pEXl::BH 207 Aspfp) and *E. coli* pop 2136 (pEXl::BH221 AsndeltaEcoRV-SmaI) strains are [NCAIM P(B) 1169] and [NCAIM P(B) 1177], respectively.

From the above brief overview and from the examples it turns out that our process to produce recombinant desulphatohirudin HV-1 variants in *E. coli* cells concerning the used structural gene, the control sequences and the expression/secretion systems, furthermore, the strains are new. Using the promoter and signal sequences of *Bacillus circulans* α-amylase gene, the artificial operon to be formed in pEX1 plasmid and the nucleotide sequences coding for the fusion proteins, we have achieved a high amount of product which after the isolation, purification and amino acid sequence analysis proved to be hirudin HV-1.

We have carried out experiments, which are detailed in Example 6, to produce recombinant desulphatohirudin HV-1 variants in Saccharomyces cells. The structural genes (33ASP and 33ASN), which were designed on the basis of Saccharomyces codon usage and had the necessary sticky ends, were inserted in YpGYOK1 and YpGYOK2 expression and secretion plasmid DNAs [*E. coli* MC1061 (YpGYOK1)/NCAIM P(B) 1166/ and *E. coli* MC1061 (YpGYOK2)/NCAIM P(B) 1167/].

The aforesaid plasmids were constructed from the plasmid DNAs pJDB207 [Beggs, Molec. Genetics in Yeast, Alfred Benzon Symposium, Vol. 18, 383–390, 1981, accession number/NCAIM (P)B 1184/], G2 [Guarente, Methods in Enzymology, 101, 181–191, 1983, accession number/ NCAIM P(B) 1182/] and Bluescript (Stratagene).

The YpGYOK1 plasmid comprises an UAS (upstream activating sequence), which can be induced by galactose and repressed by glucose, further a new pX promoter isolated and sequened by us and a part of the two-micron endogenous yeast plasmid having the terminator region of FLP gene. Besides, this plasmid contains the *E. coli* replication origin, a gene encoding the ampicillin resistance, and a bacteriophage $f_1$ origin which is necessary to the single strand formation of said plasmid together with the transfection of a helper phage, furthermore, the URA3 and leu2-d genes to control the copy number of YpGYOK1. Finally it comprises also a fragment encoding the signal sequence of the killer toxin gene of the yeast *Kluyveromyces lactis.*

The nucleotide sequence (SEQ ID NO: 31) of the pX promoter is as follows:

| | | | | | |
|---|---|---|---|---|---|
| XhoI | | | | | |
| CTCGAGGCCT | GCATTGTCAC | GAGAACATTG | AAACATATAC | AAAAAACAAA | TTTGAAATAG |
| AAAACAAAGA | ATTTACAGAA | ATGACTGCCT | GGTGCTAATT | CTTGCATATA | TTTTATTTTT |
| AATTAACTAG | AAATCAGCGT | CAATTATAGT | TTCTGGTGAG | TCAGCCAATG | TCTGTAAATA |
| AAAACAATAT | GCTTAATTAA | GAGGATTAAC | AGTGGCACAA | GAGGCAAAGA | AGGGAAGAAG |
| GCGTACACGT | CACATGAATA | TATAAAAAGA | AGAGGTTACA | TCAATTGGAC | CATCTTCGAC |
| GTTTCTATCT | GCTACAAGCC | TGTGTCGCCG | AATTACTTTA | TTGGGTCTTG | TAGAGACGCC |
| GAAATACATC | ATCATTCCAA | GATCGACGAT | AAAATCATCC | AAAAATTGTT | GCCGAAAAAA |
| AAATTGGAAA | AGGTGAAAAA | AAAATCAAAA | TACGGGTAAA | CGAGCAATCC | CTGTTCGGTG |
| CGGTGATTGG | CTTGAGGCAA | AGAGGTGTTA | TAGGAACGCA | GATCCAAA . . . SacI -- | |

FIG. 13 shows the insertion of synthetic hirudin genes into the foregoing plasmid, after in vitro site specific oligonucleotide-mediated mutagenesis using a 48- mer synthetic nucleotide fragment (FIG. 14), by fusing the regulatory sequences of the expression/secretion cassettes and the structural gene in reading frame, furthermore, by creating the cleavage site for a yeast endopeptidase, whereby the YEpGYOK1H expression/secretion plasmid was finally obtained.

Different expression/secretion plasmid systems were constructed using the above plasmid by the methods disclosed in the Examples and shown in FIGS. 15, 16, 18 and 19.

The synthetic hirudin structural genes were inserted also into the YpGYOK2 plasmid [NCAIM (P)B 1167] (FIG. 18). This plasmid comprises the whole sequence of the two-micron plasmid, the *E. coli* replication origin, a gene coding for the ampicillin resistance, furthermore the URA3 and leu2-d genes to ensure selection and the regulation of copy number of the said plasmid. The hirudin expression/secretion cassette from YEpGYOK1eb1 without the FLP terminator region and the terminator region encoding the GAPDH gene from *E. coli* MC1061 (pGAPT) [NCAIM P(B) 1164] were inserted into the foregoing plasmid. In this way we obtained the YEpGYOK2eb2 expression/secretion plasmid (FIG. 19).

Structural genes encoding hirudins were inserted into YpGYOK1 and YpGYOK2 plasmids to express hirudin under the control of the promoter and signal sequence of *Bacillus circulans* α-amylase (FIGS. 17, 18). The aforesaid expression/secretion vectors—with theoretically supposed hirudin HV-1 production in Saccharomyces cells—were transformed into Saccharomyces strains.

The *Saccharomyces cerevisiae* GYOKI1, leu, ura, ade strain is $cir^+$ [GYOKI (M)1/NCAIM (P)Y 1156/], the *Saccharomyces cerevisiae* GYOKI-5, leu, ura, gal1, reg1 strain is $cir^+$ [GYOKI (M) 5/NCAIM (P)Y 1157/] while the *Saccharomyces bayanus* GYOKI-1139, leu strain is $cir^o$ [GYOKI BO-74/NCAIM (P)Y 1158/]. *Saccharomyces cerevisiae* GYOKI (M1) was deposited at the National Collection of Agricultural and Industrial Microorganisms (NCAIM), H-1502 Budapest, Hungary, on Mar. 12, 1992, under the accession number NCAIM(P)Y 001156. *Saccharomyces cerevisiae* GYOKI M(5) was deposited at the NCAIM, on Mar. 12, 1992, under the accession number NCAIM(P)Y 001157. *Saccharomyces bayanus* GYOKI BO-74 was deposited at the NCAIM, on Mar. 12, 1992, under the accession number NCAIM(P)Y 001158.

The $cir^o$ strain contains endogenous plasmid whereas the $cir^o$ does not. In the genome of GYOKI-5 strain the gal1 gene responsible for the galactose utilization as carbon source has been damaged, therefore these cells are incapable to catabolize galactose.

After screening the hirudin production the following strains were deposited: *Saccharomyces cerevisiae* K25/2 (YEpGYOK1eb2) [NCAIM (P)Y 1172], *Saccharomyces bayanus* K9 (YEpGYOK2eb2) [NCAIM (P)Y 1173], *Saccharomyces cerevisiae* K 25/4 (YEpGYOK2eb2) [NCAIM (P) Y 1174 ] and *Saccharomyces cerevisiae* K/34 (YEpGYOL1eb1) NCAIM (P) Y 1187]. *Saccharomyces cerevisiae* K 25/2 was deposited at the NCAIM on Mar. 12, 1992, under the accession number NCAIM(P)Y 001172.

From the above brief summary and from the detailed examples it turns out that our process to produce recombinant desulphatohirudin HV-1 by means of Saccharomyces cells is new concerning the structural gene, the regulatory sequences, the expression/secretion systems in totality as well as the strains.

Employing the aforesaid nucleotide sequeñces in the constructed systems we were able to obtain cultures in high amounts and with concentrations above 100 μg/ml. After isolation and purification the product proved to have the proper HV-1 amino acid sequence.

To produce desulphatohirudin HV-1 by means of Streptomyces cells, the cassettes operating under the control of *Bacillus circulans* α-amylase promoter and signal sequence, used also to create *E. coli* and Saccharomyces expression/secretion vectors, were cloned into Streptomyces—*E. coli* bifunctional vectors in the way as disclosed in detail in Example 7, subsequently they were transformed into *Streptomyces lividans* cells [NCAIM (P)B 257]. In these constructions the synthetic hirudin HV-1 gene is under the regulation of α-amylase promoter or neomycin transferase gene and a transcription terminator. The α-amylase signal sequence provides for the secretion of the product into the intercellular space. The proper function of α-amylase signal sequence in Streptomyces cells was checked by measuring the α-amylase activity in the supernatants of *S. lividans* cells carrying α-amylase expression secretion cassettes derived from *Bacillus circulans* in Streptomyces plasmid. The restriction and functional maps of pMI 1.3, pMIAMHIR3/A, pNeoAMHIR, pdeltaNeoAMHIR, pMIdeltaNeo, pKKdeltaNeo and pMI-K2deltaNeo recombinant plasmids are shown in FIGS. 20 to 26, their construction is disclosed in detail in Example 7.

The *Streptomyces lividans* cells were transformed with the aforesaid recombinant plasmids, the transformants were cultivated and the hirudin activity of the cultures was measured. As the hirudin activity of fermentation broth was slight, new desulphatohirudin HV-1 structural gene was synthesized on the basis of better considered codon usage of Streptomyces. Cultures having hirudin activity were produced by means of this construction (Example 7).

The new gene (see FIG. 1b) was deposited under the name *E. coli* JM109 (pUC19::SH16) [NCAIM P(B) 1182] . The foregoing gene was inserted into pGYOKI1 and pGYOKI1/2 vector DNAs capable to replicate also in Streptomyces cell [NCAIM (P)B 1008 and NCAIM (P)B 1009; see also Hungarian patent specification No. 197,045]. The pGYOKI::NSH16 plasmid containing the inserted gene was deposited as *E. coli* (pGYOKI::NSH16) [NCAIM (P)B 1186].

Our *E. coli*—Streptomyces shuttle plasmid vectors and strains producing hirudin are new. The following strains were deposited from them: *E. coli* [pMIAMHIR3/A/NCAIM (P)B 1181/], *E. coli* MC1061 [pMIdeltaNeo/NCAIM (P)B 1180/] and *E. coli* MC1061 [pMI-K2deltaNeo/NCAIM (P)B 1178/].

The hirudin production by means of *E. coli* Saccharomyces and Streptomyces transformants comprising the aforesaid plasmids was investigated (see details in Example 8) under different fermentation conditions. Here we disregard the detailed description of media, because of the great number of strains and the differences in fermentation conditions.

To the maintenance and culture of strains it is required to ensure the propagation of as many living cells as possible in unit volume of cultures and to maintain the given plasmids in the cells. The medium may contain in addition to carbon and nitrogen sources also inorganic salts, trace elements, vitamins and inducers, differently depending on the strains used. The media given in Example 8 do not restrict the scope of protection because it is obvious for a skilled person that the carbon source may be not only glucose but for example saccharose, starch, maltose etc. and instead of yeast extract for example hydrolysed casein or amino acids can be used.

For the fermentation it is advantageous to use *Saccharomyces cerevisiae* GYOKI (M) 5 strain comprising plasmid with galactose-inducible UAS sequence, since the pX promoter is under the control of UAS, whereas the UAS is not repressed by glucose because of the reg1 mutation in the foregoing strain. On the other hand, the expensive galactose used as inducer does not run out of the medium, because of the presence of gal1 mutation.

The above recognition can be advantageously applied to maintain and transfer the strains and to design the steps of fermentation.

The URA3 and leu2-d genes are used as selection marker in our expression/secretion plasmids. When the transformants are grown up in minimal medium containing uracil, they develop 10–14 days and the copy number of plasmid amounts to 60–100 in these cells.

On the other hand, when the selection is carried out in the presence of leucine, the copy number is generally 10–20 and the development of transformant is much more quicker (5–6 days). At the same time, when the cells are cultivated in liquid medium in the presence of leucine, they contain the original plasmids, whereas in the presence of uracil the copy number is high, the hirudin production fluctuates and, according to our experiments, at least four different plasmid derivatives can be isolated from the cells. This means that the fermentation broth containing uracil can be advantageously used to produce higher amounts of hirudin at the final stage of fermentation, because of the higher copy number of plasmid, while media containing leucine ensuring stable plasmid maintenance are suitable in the first stage of fermentation.

The blood-clotting activity of cultures prepared by the method of Example 9 was measured by two kinds of blood tests or by using the synthetic thrombin Chromozym substrate. Since these methods determine the activity not only of the target compound, that is of hirudin HV-1, but also of the N- or C-terminally damaged derivatives, after prescreening the strains the hirudin HV-1 production of the selected cultures was determined by HPLC analysis, too.

Hirudin was prepared and purified from the culture media (Example 10), then it was identified by N- and C-terminal end-group analysis or by total amino-acid-sequence determination (Example 11).

The desulphatohirudin HV-1 compounds produced by the process of the invention are equivalent to the natural hirudins concerning their biological activity. Therefore, they can be similarly applied in the treatment and prophylaxis of thrombosis, thromboembolism etc.

Pharmaceutical products can be prepared from the produced and isolated desulphatohirudin HV-1 using the process as given in Example 12.

BRIEF DESCRIPTION OF THE DRAWINGS

The invention will be better understood with the aid of the following Figures.

FIG. 1a is the sequence of hirudin HV-1 structure gene designed on the basis of *E. coli*—Saccharomyces codon usage.

FIG. 1b is the nucleotide sequence of signal peptide and desulphatohirudin based on Streptomyces codon usage comprising the corresponding amino acid sequence. The arrows indicate the ends of oligonucleotides.

FIG. 7 is the nucleotide sequence of H16 containing the following regulatory elements: promoter (PR) with the −35, −10 and transcription initiation sites; non-translating region (5'NT); Shine-Dalgarno sequence (SD); gene coding for signal peptide; hirudin structural gene (HIR).

Figure 2:
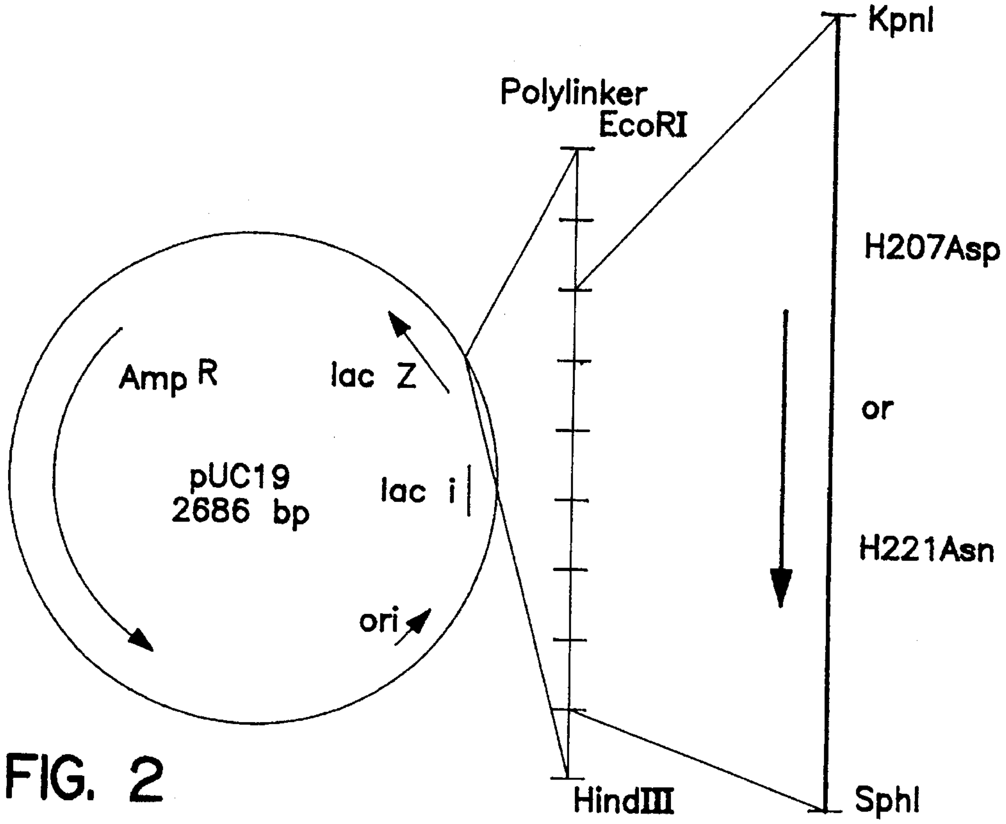
FIG. 2 is a schematic representation of the process for producing pUC19::H207 Asp and pUC19::H221 Asn vector DNAs.

The following strains as used in the process of the present invention were deposited according to the Budapest Treaty in the National Collection of Agricultural and Industrial Microorganisms (NCAIM):

*E. coli* pop 2136 (pEXl::H16 deltaEcoRV) NCAIM (P)B 001165

*E. coli* MC1061 (pGAPT) NCAIM (P)B 001164

*E. coli* GY1095 (pUN121) NCAIM (P)B 001163

*E. coli* GY1095 NCAIM (P)B 001162

*E. coli* pop 2136 NCAIM (P)B 001161

*Bacillus circulans* GYOKb-243 NCAIM (P)B 001159

*Saccharomyces bayanus* leu GYOKI BO-74 NCAIM (P)Y 001158

*Saccharomyces cerevisiae* gal1, reg1, ura3, leu GYOKI (M) 5 NCAIM (P)Y 001157

*Saccharomyces cerevisiae* ade, leu, ura GYOKI (M)1 NCAIM (P)Y 001156

*E. coli* MC1061 (YpGYOK2) NCAIM (P)B 001167

*E. coli* MC1061 (YpGYOK1) NCAIM (P)B 001166

*E. coli* pop 2136 (pEXl::BH207 Aspfp) NCAIM (P)B 001169

*E. coli* JM109 (pUC19::H16) NCAIM (P) B -001170

*E. coli* JM109 (pUC19::H207 Asp) NCAIM (P)B 001171

*Saccharomyces cerevisiae* K25/2 (YEpGYOK 1eb2 ) NCAIM (P)Y 001172

*Saccharomyces cerevisiae* K25/4 (YEpGYOK 2eb2 ) NCAIM (P)Y 001174

*Saccharomyces bayanus* K9 (YEpGYOK 2eb2) NCAIM (P)Y 001173

*E. coli* JM109 (pUC19::H221 Asn) NCAIM (P)B 001175

*E. coli* JM109 (pUN121::H16) NCAIM (P)B 001176

*E. coli* pop 2136 (pEXl::BH221 AsndeltaEcoRV-SmaI) NCAIM (P)B 001177

*E. coli* MC1061 (GYOKI-pG2) NCAIM (P)B 001183

*E. coli* MC1061 (pJDB207) NCAIM (P)B 001184

*E. coli* JM109 (pUC19::SH16) NCAIM (P)B 001182

*E. coli* MC1061 (pGYOKI::NSH16) NCAIM (P)B 001179

*Streptomyces lividans* (pGYOKI1::NSH16) NCAIM (P)B 001186

*E. coli* (pMIAMHIR 3/A) NCAIM (P)B 001181

*E. coli* MC1061 (pMIdeltaNeo) NCAIM (P)B 001180

*E. coli* MC1061 (pMIK2deltaNeo) NCAIM (P)B 001178

*Streptomyces lividans* pIJ 702 NCAIM (P)B 001185

*Streptomyces lividans* NCAIM (P)B 000257

*E. coli* K1400 pGY97 NCAIM (P)B 000358

*E. coli* pGYOKI1 NCAIM (P)B 001008

*E. coli* pGYOKI1/2 NCAIM (P)B 001009

*E. coli* NM526 NCAIM (P)B 001006

*E. coli* K 1400 NCAIM (P)B 000357

*Streptomyces tenebrarius* NCAIM (P)B 000169 1 *Saccharomyces cerevisiae* K/34 (YEpGYOK 1eb1) NCAIM (P)Y 001187

Hungarian patent specification No. 197,045 (Process to construct bifunctional DNA cloning vectors and to produce their transformants) and No. 204,892 (Process to produce new DNA cloning vector and gene bank) are referred to here as literature sources.

The invention is further illustrated, without restricting the scope claimed, in the following Examples. The % denote mass percentages if not otherwise mentioned.

EXAMPLE 1

Production and Cloning of Gene Encoding Hirudin

1.A. In vitro synthesis of the hirudin gene

The isoform of hirudin HV-1 gene was designed on the basis of *Escherichia coli* and *Saccharomyces cerevisiae* combined codon usage. The designed nucleotide order is shown in FIG. 1*a*. The gene was joined together from oligonucleotides (see the arrows in FIG. 1*b*) in such a way that the necessary overlapping base pairs (14–20 bp) were designed. The oligonucleotides were chemically synthesized in Applied Biosystem Cyclone DNA-synthesizer according to the instructions of the manufacturer from β-cyanoethyl-diisopropyl-phosphoramidite monomers. At the triplet encoding the 33th amino acid mixed matching was applied to join the first base of the codon (in the III. fragment A+G and in the IV. fragment T+C).

At the end of the synthesis the optical density of the obtained solutions was measured at 260 nm and the concentration was calculated with the aid of the following equation: OD260/sum epsilon=concentration (mole/liter). Sum epsilon is the sum of molar extinctions of nucleotides to be found in oligonucleotides. This value is for the individual nucleotides as follows: A: 15.4×103 l/M; C: 7.3×103 l/M; G: 11.7×103 l/M; T: 8.8×103 l/M. After synthesis the detritylated oligonucleotides obtained were purified by vertical preparative denaturing polyacrylamide gel electrophoresis in 10% of urea. To prepare the gel 84 g of urea, 15 ml of 10-fold TEB buffer, and 50 ml of 40% acrylamide and bisacrylamide in a ratio of 19:1 were adjusted to 200 ml with distilled water, the urea was dissolved therein, then 600 μl of 10% ammonium persulphate (APS) and 140 μl of N,N,N',N'-tetramethyl-ethylenediamine (TEMED, Sigma, USA) were added and the gel was poured between two glass plates located 2 mm from each other. The composition of 10-fold TEB buffer is as follows: 0.89M Tris base, 0.89M boric acid and 0.02M ethylenediaminetetraacetic acid (EDTA) in water. After 30 minutes polymerization the gel was placed into the electrophoresis apparatus. 10 μM of oligonucleotide were mixed with the same amount of formamide loading buffer (95% of formamide, 10 mM of EDTA, 0.05% of bromophenol blue and 0.05% of xylene cyanol) and after 5 min. boiling it was loaded into the slab of the gel. The gel was run at constant power (45 W) as long as the bromophenol blue reached the end of it. The glass plates were removed, the gel was laid onto plastic wrap and the highest density band of interest was excised in ultraviolet light (UV, 260 nm) using a white paper sheet as background. After vigorous crushing the gel was rotated for 16 hours in 5 ml of 0,1M sodium chloride (NaCl) solution. The gel fragments were centrifuged [Janeczky K23 swinging bucket rotor, in glass centrifuge tube (10 ml), at 4200 revolution per minute (rpm) at 4° C. for 10 min]. The supernatant was recovered and loaded onto preactivated DE 52 column, which was washed three times with 4 ml of distilled water, and the DNA was eluted three times with 1 ml of 1M NaCl.

The activated DE 52 column was made in the following way: 5 g of DE 52 cellulose (Whatman) were suspended in 75 ml of 1M NaCl solution in Erlenmeyer flask for 0.5 hour, the resin was allowed to settle and the supernatant was removed by aspiration. This procedure was repeated three times, finally the supernatant was left. Cotton-wool was stuffed into the conical end of a Gilson-pipette tip. 1.5 ml of the DE 52 slurry was packed into the aforesaid column. After desalting with water the oligonucleotide sample was loaded. The eluted oligonucleotides were precipitated by threefold volume of ammonium acetate and ethanol mixture in liquid nitrogen. The ammonium acetate and ethanol mixture was made by mixing 30 ml of 7.5M ammonium acetate and 180 ml of 96% ethanol. To recover the oligonucleotides the DNA was thawed, centrifuged (12,000 rpm for 10 min. at room temperature), desiccated under vacuum and redissolved in sterile distilled water.

The ends of the synthetic fragments were phosphorylated all but I and VI. For the phosporylation 150 pM deoxy-5'-adenosine-triphosphate (in 1.5 μl of water), 5 μCi γ-32 P-dATP, 3 μl 5-fold kinase buffer [250 mM of Tris.Cl (pH 7.5), 50 mM of magnesium chloride, 10 mM of dithiothreitol] and 1 μl (10 units) of T4 polynucleotide kinase (BRL, USA) were added to 10 μl of 10 pM oligonucleotide solution and incubated for 45 min. at 37° C., then it was boiled for 3 min. at 100° C. and subsequently purified on the aforesaid denaturing gel, with the difference that the oligonucleotide band was detected by autoradiography. The gel was wrapped in plastic wrap and in darkroom the sample was placed onto a sheet of x-ray film (MEDIFORT RT, Forte, Vác) and exposed for 5 min, subsequently the film was developed according to the instructions of the manufacturer firm and then it was replaced on the gel as it had been under the exposition. The piece of gel was excised corresponding to the black spot on the film and it was extracted, chromatographed and precipitated as given above.

The oligonucleotides were mixed (10–10 μl) and annealed (at 65° C. for 1 hour), precipitated and purified on gel by methods given above, except that the urea was omitted. After reprecipitation they were dissolved. The resulted duplices were linked together in such a way that 6 μl (40 pM) of I+II duplices +6 μl (40 pM) of III+IV duplices+6 μl (40 pM) of V+VI duplices and 6 μl of 5-fold ligase buffer [250 mM Tris. Cl (pH 7.5) and 50 mM of magnesium chloride], 3 μl of 10 mM adenosine 5'-triphosphate (ATP), 3 μl of 100 mM dithiothreitol (DTT), and 0.5 μl (0.5 unites) of T4 ligase (Boehringer Mannheim GmbH, Germany) were mixed, then that the reaction mixture was incubated at 16° C. for 16 hours, and finally the ligation product was repurified on neutral gel using the aforesaid methods.

1.B. Cloning of the synthesized gene

The cloning was carried out using pUC19 plasmid vector. The *Escherichia coli* JM109 (pUC19) (New England Biolabs., USA) strain was maintained on LBa medium. To prepare LBa 10 g of tryptone (Bacto), 5 g of yeast extract (Bacto) and 10 g of NaCl were dissolved in 0.8 1 of distilled water, pH 7.5 was adjusted with 0.01M sodium hydroxide or 0.01M hydrochloric acid and 17 g of Bacto agar were added, then the volume of the solution was adjusted to 11 and the solution was sterilized for 30 min at 37° C.

The plasmid DNA was isolated by maxiprep method. The microorganisms were cultivated in LB medium. The composition of LB medium is the same as that of the LBa but it contains no agar. The sterile medium containing 50 μg/ml of ampicillin was inoculated with 0.1 ml of the aforesaid culture. The cultures were shaken on a rotary shaker (200 rpm) for 16 hours at 37° C. Cells produced in this way were harvested in Sorvall RC3B centrifuge at 4° C. for 30 min. at 4200 rpm. The cells were suspended in 67 ml of TGE. The TGE solution contains 2.3 ml of 40% glucose solution in water, 2.5 ml of 1M Tris. C1 solution (pH 8.0) in water, 4 ml of 0.25M EDTA (Reanal, Budapest) solution and 91.2 ml of deionized water. Cells suspended in TGE were treated with 134 ml of NSE. To prepare NSE solution the following ingredients were added to 138.7 ml of distilled water: 13.3 ml of 3M sodium hydroxide solution in water, 8 ml of 25% sodium lauryl sulphate solution and 40 ml of 0.25M EDTA solution in water. The clearing lysate was incubated for 1 hour at 0° C., then 100 ml of 3/5M potassium acetate solution were added and it was left to stand at 0° C. for 20 minutes. The potassium acetate solution was prepared by adding 230 ml of glacial acetic acid and 57 ml of distilled water to 588.9 g of potassium acetate dissolved in 1200 ml of distilled water. The above suspension was centrifuged in Sorvall RC-5 centrifuge at 8000 rpm in GS-3 rotor at 0° C. for 20 min. The supernatant was precipitated by 18 ml of −20° C. isopropanol and incubated for 1 hour at −20° C. The DNA precipitate was harvested by centrifugation at 0° C. and it was washed with 10 ml of ethanol, finally dried in vacuum desiccator. The product was dissolved in 7 ml of TE solution containing 250 ml of 0.01M Tris.Cl (pH 7.5) buffer and 1 ml of 0.25M EDTA in water.

Cesium chloride (Serva) and 10 μg/ml of ethidium bromide were dissolved in the 7 ml of the foregoing solution, then the obtained solution was centrifuged in T865.1 rotor of Sorvall OTD-50B ultracentrifuge for 48 hours at 15° C. and at 39000 rpm. The lower band was detected in UV light and removed by syringe, the ethidium bromide was extracted three times with double volume of butanol. The solution containing the plasmid was dialyzed in a 1000-fold volume of TE solution resulting in pure pUC19 plasmid DNA. The concentration of DNA was calculated on the basis of optical density at 260 nm; 10 D 260 equals 50 μg/ml of DNA. The pUC19 DNA was digested by using KpnI and SphI restriction endonucleases according to the instructions of the manufacturer. Thereafter 50 μl of digested pUC19 DNA and 5 pM of double-stranded hirudin gene were mixed and ligated with T4 DNA ligase (Boehringer Mannheim GmbH, Germany) according to the instructions of the manufacturer.

The ligated DNA was transformed into *E. coli* JM109 competent cells (Pharmacia LKB). The competent cells were produced by the following method:

*E. coli* JM109 strain was preserved at −70° C. For this preservation the *E. coli* JM109 strain was cultivated in M9 medium for 48 hours at 37° C. using vigorous shaking. For preparaing the M9 medium 6 g of disodium hydrogen phosphate, 3. g of potassium dihydrogen phosphate, 1 g of ammonium chloride, and 0.5 g of sodium chloride were dissolved in 1 l of distilled water and sterilized for 30 min. at 121° C. After sterilization and cooling the following sterile solutions were added: 1 ml of 1M magnesium sulphate, 1 ml of 0.1M calcium chloride, 1 ml of 1.0M thiamine hydrochloride and 5 ml of 20% glucose. To 3 ml of grown culture 225 μl of dimethyl-sulphoxide (DMSO) were added and after mixing it was stored at −70° C. 0.1 ml of the thus-preserved culture was inoculated into 5 ml of 2TY medium and vigorously shaken at 37° C. for 16 hours to propagate the cells. To prepare the 2TY medium 16 g of tryptone (Bacto), 10 g of yeast extract (Bacto) and 5 g of NaCl were dissolved in 1 l of distilled water and adjusted to pH 7.3 with 0.1M sodium hydroxide solution, then it was sterilized for 30 min. at a temperature of 121° C. The cells were then cultivated in a prewarmed Erlenmeyer flask (37° C.) in 100 ml of 2TY medium inoculated with 1 ml of said cells and the flask was vigorously shaken at 37° C. Subsequently, the culture was chilled by placing the flask in ice and harvested in Janetzky K23 centrifuge using swinging bucket rotor at 4000 rpm for 10 min at 0° C. The supernatant was discarded and the pellet was suspended in 50 ml of 50 mM sterile chilled calcium chloride solution, left to stand for 20 min. at 0° C., centrifuged as above, the supernatant was discarded, the sediment was suspended in 9 ml of 50 mM sterile chilled calcium chloride solution, then 1.5 ml of 87% aqueous sterile chilled glycerine were added, and after vigorous mixing 300 μl portions of the suspension were divided into Eppendorf tubes (1.5 ml, Greiner, Germany). After freezing in liquid nitrogen they were stored at −70° C.

To transform the competent cells they were thawed, 5 μl of ligate were added, then they were incubated for 20 min. in ice bath, for 3 min. at 30° C. and again in ice bath for 2 min. After 1 hour incubation in 1000 μl of 2TY medium at 37° C., the following substances were added: 25 μl of 0.1M IPTG, 25 μl of 2% 5-bromo-4-chloro-3-indolyl-β-D-galactoside (X-gal) and the thus-obtained mixture was plated at 1:10, 1:100 and 1:1200 dilutions onto LBa plates containing 50 μg/ml of ampicillin. The thus-grown white colonies were inoculated and cultured in 3 ml of LB medium containing 50 μg/ml of ampicillin for 16 hours in a shaking incubator at 37° C.

The isolation of plasmid DNA by miniprep method was carried out as follows: 1.5 ml of cell culture grown at 37° C. for 16 hours were centrifuged in Eppendorf tube (1,5 ml) for 2 min. at 1200 rpm. The supernatant was discarded and the pellet was suspended in 100 μl of TGE, then 200 μl of NSE (see above) were added. After vigorous mixing it was incubated in ice bath for 5 min. Subsequently, 150 μl of 3/5M potassium acetate solution were added and incubated for 5 min. in ice bath. After centrifugation (5 min., 12,000 rpm) the supernatant was collected and precipitated in 700 μl of −20° C. absolute ethanol. The DNA precipitate was collected by centrifugation (5 min., 12,000 rpm), and after dessication it was dissolved in TE containing 100 μg/ml of ribonuclease (Reanal, Budapest) and incubated for 1 hour at 37° C. Subsequently, the DNA sample was treated with phenol, then precipitated and dissolved in 50 μl of TE. The TGE, NSE and 3/5M potassium acetate solutions were prepared according to the methods described at maxiprep. In the case of phenol treatment the sample was mixed on a vortex with an equal volume of a 25:24:1 mixture of phenol, chloroform, and isoamyl-alcohol. After centrifugation of the suspension the aqueous phase was carefully removed. To equilibrate the phenol 1l of liquified phenol and 1 l of 0.1M Tris. Cl (pH 8) were shaken and in a separatory funnel the aqueous phase was adjusted to pH 8 with 1M sodium hydroxide solution under permanent stirring. Subsequently, the lower phase was equilibrated again with 1 l of 0.1M Tris base, then 0.2% of β-mercaptoethanol and 0.1% of 8-hydroxy-quinoline were added. The phenol prepared in this way was mixed with chloroform and isoamyl-alcohol in the ratio mentioned above.

The foregoing DNA was digested with PvuII restriction endonuclease (New England Biolabs., USA) according to the instructions of the manufacturer, and the nucleotide order was determined by sequenation. This was achieved by Sequenase version 2.0 DNA sequencing kit (United States Biochemical, USA) according to the procedure of the manufacturer. The desired clones were selected on the basis of sequence analysis. Two of them were named *E. coli* JM109 (pUC19::H207 Asp) and *E. coli* JM109 (pUC19::H221Asn). FIG. 2 shows their physical and functional maps.

One colony was selected by streaking the original population on LBa containing 50 μg/ml of ampicillin and it was inoculated in 5 ml LB containing 50 μg/ml of ampicillin. After 16 hours of incubation at 37° C., 3 ml of the resulted culture and 225 μl of DMSO were mixed and stored at −70° C.

The strains were deposited under the following accession numbers:

*E. coli* JM109 (pUC19::H207 Asp) [NCAIM (P)B 1171] and

*E. coli* JM109 (pUC19::H221 Asn) [NCAIM (P)B 1175].

EXAMPLE 2

Cloning and Expressing the α-Amylase Gene of *Bacillus Circulans*

2.A. Cultivation of *Bacillus circulans* cells

The *Bacillus circulans* GYOKb-243 [NCAIM (P)B 1159] microorganism was cultivated in LB (see Example 1) for 1 day at 37° C. 100 ml of LB medium were inoculated with a cell derived from solid culture in a 500 ml total-volume Erlenmeyer flask and cultivated for 12 hours at 37° C. The cell count of the cultures was 4–6×$10^8$/ml.

2.B. Isolation and purification of *Bacillus circulans* total DNA

The cells were harvested by centrifugation from the culture cultivated according to the method described in Example 2A. After that the cells were washed with 0.1M EDTA and 0.15M NaCl solution (pH 8.0) and resuspended in 7 ml of the above solution containing also 1 mg/ml of lysozyme (Sigma). The suspension was incubated for 1.5 hours at 37° C. Thereafter sodium dodecyl sulphate (SDS) and sodium perchlorate (at 1.3M and 1M total end concentrations, respectively) were added to the viscous mixture and carefully extracted with chloroform and isoamylalcohol in the ratio of 2.5:1. The upper phase was separated by centrifugation (3000 rpm, 2 min.) and treated with 120 μg/ml of ribonuclease (Sigma) for 60 min. at 37° C. to degradate the ribonucleic acids. After that sodium-4-amino salicylic acid was added at a final concentration of 6%. The reaction mixture was carefully extracted with an equal volume of phenol which was distilled and saturated with water for 30 min. After centrifugation the upper phase was recentrifuged. To remove the phenol the phase containing DNA was extracted two times with ether and the traces of ether were removed by bubbling air through the solution. The DNA was precipitated with double volume of ethanol, then the precipitation and the dissolution were repeated three times. Finally the DNA was dissolved in a mixture of 0.15M NaCl and 0,015M sodium citrate solutions and the DNA was stored in refrigerator until utilization.

2.C. Construction of pGY97 phasmid vector

Figure 3:
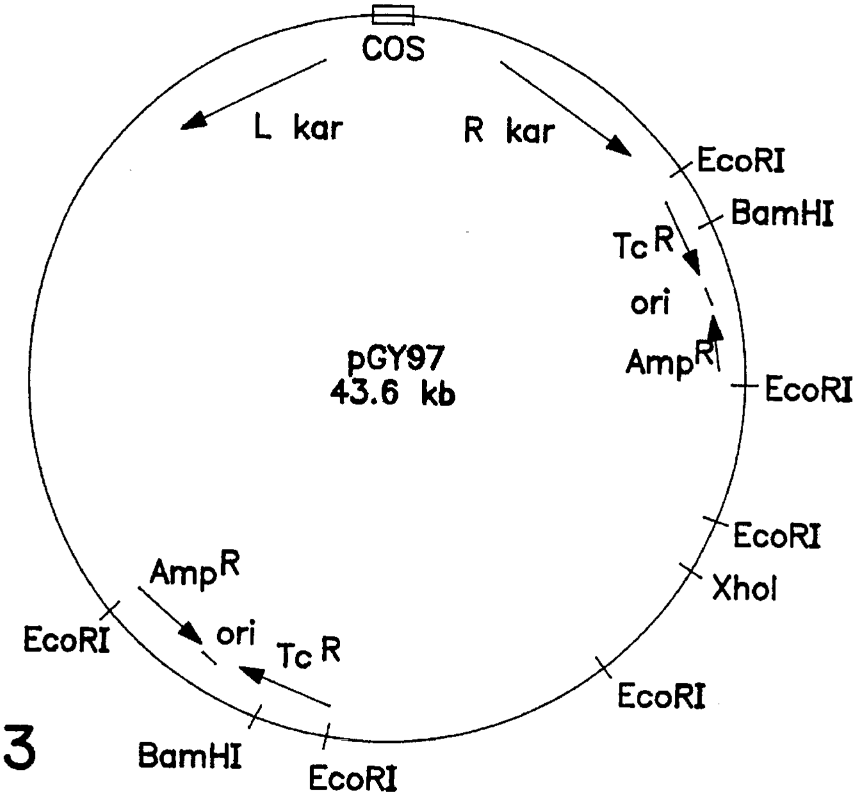
FIG. 3 shows the partial restriction and functional map of pGY97 vector.

The Hungarian patent specification No. 204,892 discloses the production, purification and usage for cloning of the pGY97 phasmid vector (its physical and functional map is presented in FIG. 3). Our work is based on these detailed methods, therefore only the brief description thereof is presented here.

*E. coli* K1400 (pGY97) [accession number: NCAIM (P)B 358] strain was stored at −70° C. The cells were cultivated until the stationary phase of growth in TA medium containing 50 μg/ml of ampicillin at 28° C. Thereafter 3 ml of the culture broth and 0.225 ml of DMSO (Sigma) were mixed and stored at −70° C. To prepare TA medium 10 g of tryptone (Bacto), 1 g of yeast extract (Difco) and 5 g of NaCl were dissolved in 1 l of distilled water, then 1 ml of 0.1M magnesium chloride and 1 ml of 1M calcium chloride solutions were added. The medium was sterilized for 30 min. at 121° C. To make solid TAg medium the same procedure was applied, with the difference that the TAg was supplemented with 20 g/l of agar.

2.D. Production of pGY97 recombinant phasmid in phage form from *E. coli* K1400 (pGY97) [NCAIM (P)B 358] cells The *E. coli* K1400 (pGY97) [NCAIM (P)B 358] strain was stored and cultivated according to Example 2C. The accession number of *E. coli* K1400 is NCAIM P(B) 357. To purify the pGY97 phasmid in phage form *E. coli* NM526 strain was transfected at 37° C. and the phage titer was determined. At this temperature the pGY97 phasmid propagates in phage form. The phage stock was stored in a suspension containing chloroform at 4° C. 4 ml of the phage suspension produced by *E. coli* NM526 [NCAIM (P)B 1006] in TA medium and 0.1 ml of chloroform were vigorously mixed and stored at 4° C. To obtain single plaques the phage stock was diluted, then *E. coli* NM526 strain was transfected. A single plaque was picked and suspended in 1 ml of SM, thereafter it was gently shaken for 4–6 hours at 0° C. To prepare SM solution 20 ml of 1M Tris.Cl (pH 7.5) buffer, 5.8 g of NaCl, 2.0 g of magnesium sulphate, and 20 g of gelatine were dissolved in 1 l of distilled water. The solution was sterilized for 20 min. at 121° C. From 0.1 ml of phage suspension a plate lysate was prepared on TAg medium.

The plates were incubated for 8–10 hours at 37° C. 6 ml of SM buffer were poured onto the totally cleared plate lysate and it was gently shaken at 0° C. 5 ml of aforesaid plate lysate were added to 500 ml of bacterial cell culture reaching the exponential phase of growth (OD600=0.3) in TA medium, and the transfected culture was incubated in a 37° C. shaking incubator. The value OD600 of the culture was measured at every 30 minutes, and at reaching the minimum the lysate was cooled to room temperature and 5 ml of chloroform were added. After intensive shaking it was treated with RN-ase (Sigma) at 1 μg/ml final concentration and incubated for 30 min. To 500 ml of lysate 29.2 g of crystalline NaCl were added and the salt was dissolved by blending for 1 hour. The debris of cells were removed by centrifugation (1100 rpm) at 4° C. for 10 min. The supernatant was collected and crystalline polyethylene glycol 6000 (PEG 6000, FLUKA) was added (final concentration 10%). After dissolving the PEG therein it was incubated for 1 hour at 0° C. and the formed precipitate was collected by centrifugation (11,000 rpm). The supernatant was discarded and the pellet was carefully extracted with an equal volume of chloroform. The two phases were selected by centrifugation and 0.5 g/ml of cesium chloride (Serva) was added to the aqueous phase. After the CsCl was dissolved, the phage suspension was carefully layered onto CsCl step gradient. The CsCl gradient was prepared in SM using the following solutions:

| Solution | Density (g/ml) | CsCl (g) | SM (ml) | Refractive index (n) |
|---|---|---|---|---|
| a | 1.45 | 60 | 85 | 1.3768 |
| b | 1.50 | 67 | 82 | 1.3815 |
| c | 1.70 | 95 | 75 | 1.3990 |

3 ml of solution c was pipetted into SW28 clear polypropylene centrifuge tubes (Sorvall), thereafter 3 ml of solution b, then 4 ml of solution a were carefully layered on one another. 20 ml of phage suspension was layered onto this gradient. The centrifugation was carried out in Sorvall OTD-50B ultracentrifuge for 2 hours at 4° C. in SW28 rotor (22,000 rpm). The phage band was collected by hypodermic needle (an opalescent band between a and b layers) and its volume was adjusted to 10 ml with 1.5 g/ml of CsCl dissolved in SM.

This suspension was poured into a plastic centrifuge tube and centrifuged in SW50.1 rotor at 38,000 rpm for 24 hours at 4° C. in the above centrifuge. The phage band was collected by hypodermic needle and dialyzed against a 1000-fold volume of NTM buffer [10 ml of 1.0M NaCl, 20 ml of 1.0M Tris.Cl (pH 7.5), 10 ml of 1.0M magnesium chloride and 960 ml of deionized water].

2.E. Isolation of pGY97 phase DNA

After dialyzation the following ingredients were added to 1.0 ml of phage suspension: 0.5M of EDTA (pH 8.0) at 20 mM final concentration, 50 μg/ml of proteinase K and 20% sodium lauryl sulphate at 0.5% final concentration. The mixture was incubated for 1 hour at 37° C. After digestion it was treated with phenol by stirring the mixture with an equal volume of phenol and chloroform in a ratio of 1:1, then the two phases were separated by centrifugation (10 min., 10,000 rpm). The aqueous phase was dialyzed against a 1000-fold volume of TE buffer. The concentration of DNA was calculated on the basis of the measured optical density at 260 nm (1 OD260 unit equals 50 μ/ml DNA).

2.F. Preparation and ligation of vector and insert DNA 12.5 μl of B-buffer were added to 12.5 μl of phasmid DNA purified according to Example 2E. To the reaction mixture containing phasmid DNA 5 units of XhoI restriction endonuclease (BRL, Maryland, USA) were added and incubated for 1 hour at 37° C. To prepare the B-buffer 1000 μl of 3M NaCl, 120 μl of 1M Tris.Cl (pH 7.5) and 120 μl of 1M magnesium chloride, furthermore 8.4 μl of β-mercaptoethanol and 8650 μl of distilled water were mixed. The efficiency of digestion was controlled by gel electrophoresis. The quality of digestion was controlled by ligation and redigestion with XhoI. If the first digestion is correct, the bands of first digestion pattern will appear after subsequent ligation and redigestion. To 1 μl of digested samples 10 μl of D-buffer were added and the obtained fragments were separated by agarose gel electrophoresis in a known way. For preparing the D-buffer 5 ml of 80% sucrose, 0.01 g of bromophenol blue, 0.4 ml of 1M Tris.Cl (pH 7.5) and 4.0 ml of distilled water were added. The agarose gel was prepared by adding 1 g of agarose (Sigma, St. Louis, USA) to 80 ml of TEA buffer and this suspension was boiled for 2 min. After cooling to 60° C. it was poured into horizontal mold. For preparing the TEA buffer 48.4 g of Tris base, 3.7 g of disodium-EDTA and 16.4 g of sodium acetate were dissolved in 800 ml of distilled water. In the above case the TEA was supplemented with 0.05 ml of 10 mg/ml of ethidium bromide solution. The TEA buffer was adjusted with concentrated acetic acid to pH 8.5 and distilled water was added to reach the final volume of 1000 ml.

After checking the aforesaid fragments, they were treated with phosphatase. The phosphatase treatment was accomplished in the following way: to the DNA treated with XhoI enzyme 20 units of phosphatase (Calf Intestinal, Boehringer Mannheim GmbH, Germany) were added and first incubated for 15 min. at 37° C., then for 15 min. at 56° C. Following that, the sample was treated with 20 units of bacterial alkaline phosphatase (BRL, Maryland, USA) in the same buffer for 60 min. at 68° C. After these treatments the sample was extracted with an equal volume of phenol and chloroform in the ratio of 1:1. After careful mixing the two phases were separated by centrifugation (10 min., 10,000 rpm). The aqueous phase was extracted three times with ether and precipitated by adding two and a half volume of 96% ethanol. The precipitated DNA was collected by centrifugation (10,000 rpm). The supernatant was discarded and the DNA was desiccated and dissolved in 20 μl of TE solution. The efficiency of phosphatase treatment was checked by ligation (using untreated XhoI fragments as control). If the treatment is proper, after ligation the starting fragments can be received. The phosphatase-treated vector fragments can not ligate to themselves (see Hungarian patent specification No. 204,892). 12.5 μl of the thus-produced pGY97 phasmid DNA and 12.5 μl of B-buffer were mixed and digested with 5 units of BamHI restriction endonuclease (BRL, Maryland, USA) by incubating for 1 hour at 37° C.

125 μl of *Bacillus circulans* total DNA solution purified according to the method described in Example 2B were digested with 1 unit of Sau3AI restriction endonuclease (BRL, Maryland, USA) in 125 μl of B-buffer by incubating for 10 min. at 37° C. The partially digested DNA was treated with phenol and precipitated with ethanol.

The DNA was redissolved in 500 μl of TE. The Sau3AI partially digests the DNA, resulting in fragments of different lengths. Because the optimal length of fragments to be cloned into the vector is in the range of 9 to 15 kb, to separate these fragments the partial digest was loaded onto sucrose gradient. During the gradient centrifugation the fragments separate from one another according to their size. In this way there is a good opportunity to isolate the preferred fragments. The sucrose gradient centrifugation was performed in the following way: a continuous sucrose gradient (ranging from 10 to 40%) in SW41 centrifuge tube was prepared. The 10 and 40% sucrose solutions were made in TE buffer containing 1M of sodium chloride. 6 ml each of these solutions were mixed with a gradient mixer apparatus and filled into centrifuge tubes. 500 μl of DNA sample was loaded onto the top of the gradients and centrifuged in Sorvall OTD-50B ultracentrifuge at 4° C. for 16 hours at 32,000 rpm. After finishing the centrifugation 200 μl fractions were collected and the size of DNAs was determined by agarose gel electrophoresis. 10 μl each of the DNA fractions were mixed with 10 μl each of D buffer, then the solutions were loaded into the slabs of the gel and the samples were analyzed by electrophoresis (40 V, 40mA) in TEA buffer.

DNA bands corresponding to different sizes of DNA fragments were observed on the basis of their fluorescence in UV light and they were identified by taking photograph. The proper fractions were united, precipitated with ethanol and redissolved in 10 μl of TE. The BamHI restriction endonuclease cleaves the DNA at GGATCC sequence whereas the Sau3AI at GATC sequence. After cleavage so called "sticky ends" are created having 4 bases in common, therefore they can join together. 10 μl of pGY97 DNA digested with BamHI and 10 μl of partially digested (Sau3AI) *Bacillus circulans* DNA were ligated by adding 5 μl of L buffer and 5 units of T4 DNA ligase (BRL, Maryland, USA) to the reaction mixture and incubating it for 16 hours at 15° C.

The L buffer contains 1.25 ml of 1M Tris.Cl (pH 8.0), 0.25 ml of 1M magnesium chloride, 0.5 ml of 1M dithiothreitol, 30.3 mg of ATP and 3 ml of deionized water.

2.G. In vitro packaging of phage DNA

In the reaction mixture those DNA molecules appear during the ligation which contain the proper fragments of *Bacillus circulans* DNA between two properly oriented vector-arm molecules. These molecules were packed into phage particles by in vitro packaging mixtures.

The in vitro packaging means that infectious phage particles can be formed by adding phage DNA to appropriate *E. coli* cell lysates (SE and FTL) in a proper buffer.

Figure 4:
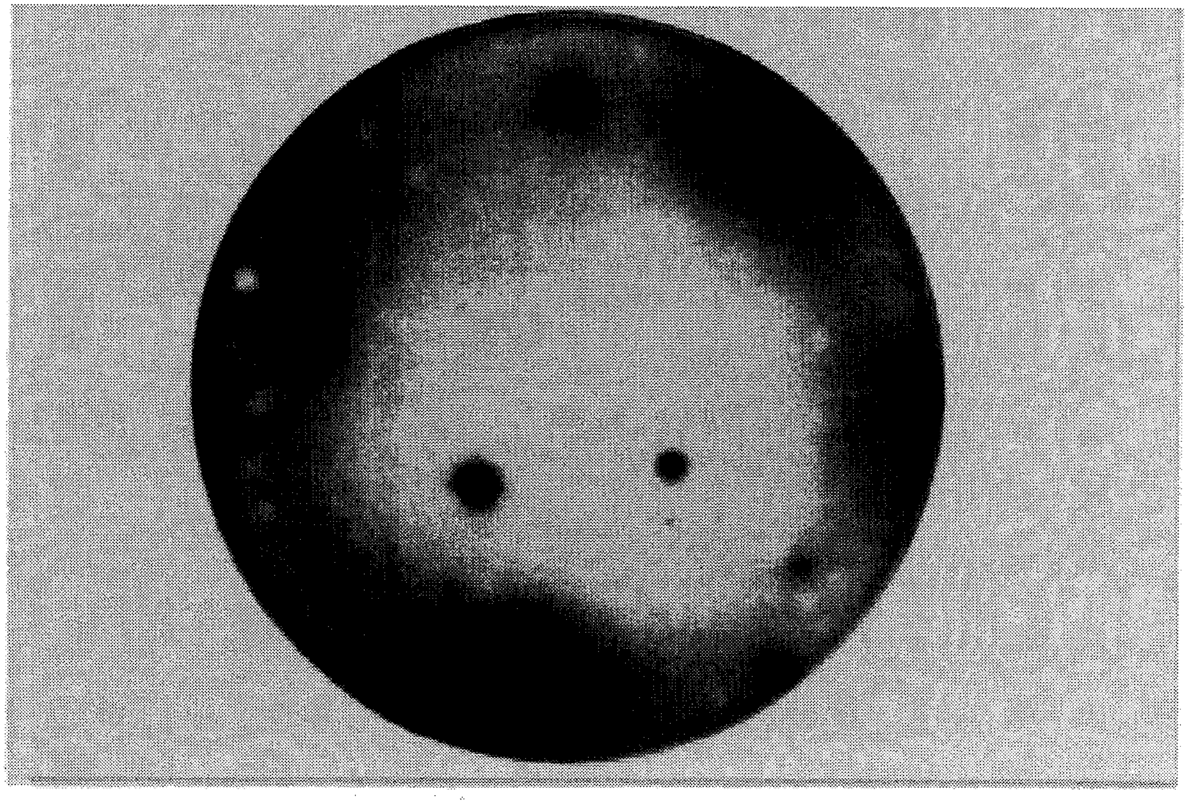
FIG. 4 is the photograph of a plate transfected by phage and stained by iodine. The arrow indicates one of the phage plaque containing the pGYOKI 30 vector.

The packaging was achieved by a commercially available in vitro kit (Amersham) according to the description of the manufacturer. Briefly, the packaging was carried out in the following way: 2 μl SE and 5 μl FTL lysates from the kit were thawed in an ice-water bath, then they were added to 8 μl of DNA packaging buffer and 10 μl of ligate (see above). After immediate mixing the mixture was incubated first at 0° C. for 10 min, then at 25° C. for 60 min. The cultivation of host bacteria and determination of the number of phages were carried out by the instructions of the in vitro packaging kit. The TAK medium is the same as TA but the former contains 2.2% of agar (Bacto) and 1% of starch (BDH). After 12 hours incubation 1300 plaques were found. In the control ligation (without *Bacillus circulans* DNA) no plaque appeared. Among the 1300 plaques there was one $Amy^+$ (digesting starch and having amylase activity) recombinant phage (FIG. 4). To detect the $Amy^+$ phage plaque the plate containing the transfected culture was placed into iodine vapour. The iodine stains the starch blue, therefore the plaque which contains biosynthesized amylase digesting starch remains white (FIG. 4). The $Amy^+$ phage plaque was multiplicated according to the methods given in Examples 2D and 2E, subsequently the phage DNA was isolated and digested by using BamHI, BglII, EcoRI, HindIII, PstI (New England Biolabs., USA) restriction enzymes according to the instructions of the manufacturer. The digests were analyzed by gel electrophoresis (according to Example 2F) and their restriction map shown in FIG. 5 was constructed. The recombinant phage clone was called pGYOKI-30.

2.H. Subcloning of α-amylase gene

Figure 5:
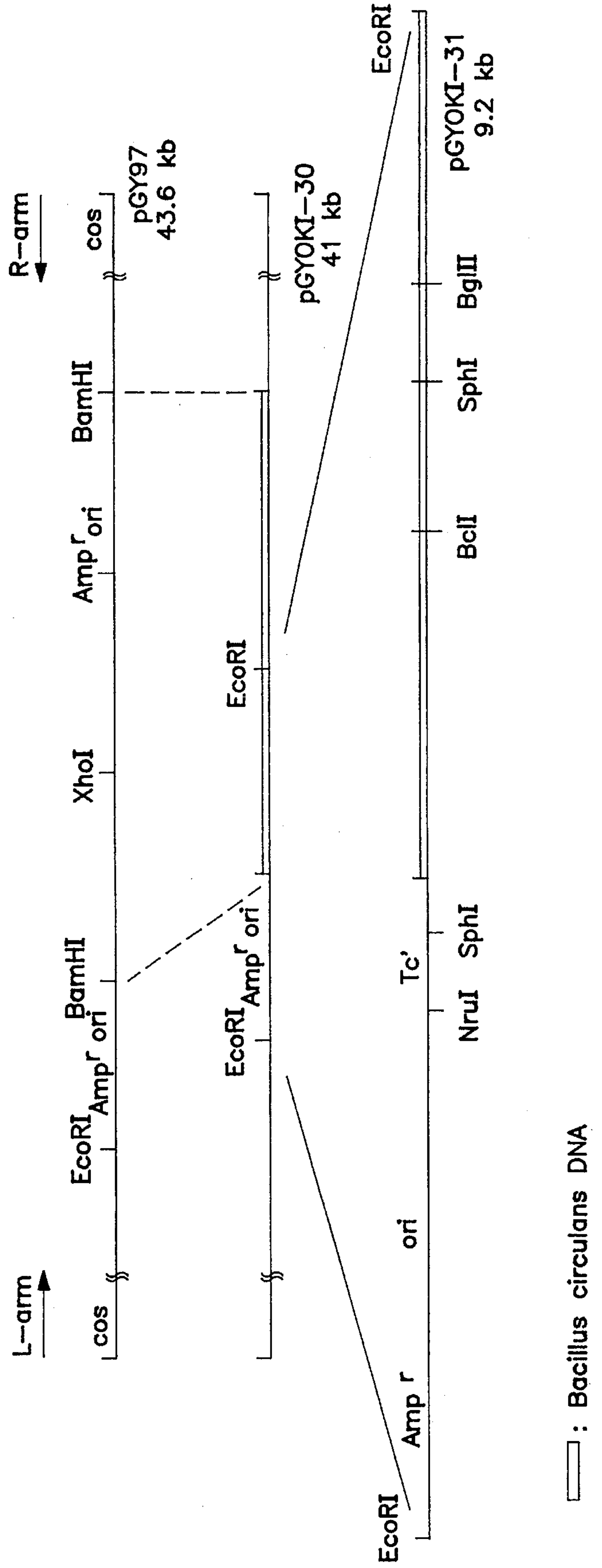
FIG. 5 is a schematic representation of the process used for producing the pGYOKI30 and pGYOKI31 vector DNA.

DNA described in Example 2G was digested with EcoRI (New England Biolabs., USA) restriction endonuclease (using the method of the manufacturer). The digestion was controlled by gel electrophoresis method described in Example 2F; the digestion was partial. Thereafter the mixture was extracted with phenol, precipitated with ethanol and religated by the method of Example 2G. *Escherichia coli* GY1095 [NCAIM P(B) 1162] competent cells were transformed with 10 μl of ligate. The competent cells were produced by the procedure described in Example 1B except that *E. coli* GY1095 [NCAIM P(B) 1162] strain was applied. The transformed cells were plated on solid TAK medium containing 50 μg/ml of ampicillin. The cultures were incubated for 12 hours at 37° C. The ampicillin-resistant (ApR) colonies (transformation frequency: 10,000 transformants/1 μg DNA) were checked in iodine vapour for Amy phenotype. One $Amy^+$ colony was propagated and the resulted strain was called GY1095 (pGYOKI-31). FIG. 5 shows its physical and functional map.

2.I. Production and purification of pGYOKI-31 plasmid DNA

The GY1095 (pGYOKI-31) strain was preserved at −20° C. Plasmid DNA was isolated therefrom by maxiprep described in Example 1B, except that the medium was inoculated by GY1095 (pGYOKI-31) strain. The partial restriction map of the plasmid was determined by the method described in Example 2C. using AvaI, BclI, ClaI, KpnI, and PvuI enzymes, too.

2.J. Production of pGYOKI-33 and pGYOK-34 plasmids

Plasmid DNAs were isolated from *E. coli* JM109 (pUC19) and GY1095 (pGYOKI-31) strains using the maxiprep method mentioned in Example 1B. The pUC19 vector DNA was digested with SphI. Thereafter to make linear form and delete fragments from the pGYOKI-31 it was digested with SphI and NruI (New England Biolabs., USA) restriction endonucleases using the circumstances given by the manufacturer. The mixture was extracted with phenol in the way as described in Example 1B, subsequently it was precipitated (Example 2F), and after redissolving it was ligated in the ligation buffer with T4 DNA ligase (Boehringer Mannheim GmbH, Germany) applying the method of the manufacturer for 16 hours at 16° C. After ligation it was transformed into *E. coli* GY1095 competent cells and plated onto TAK medium containing 50 μg/ml of ampicillin according to Example 2H.

Figure 6:
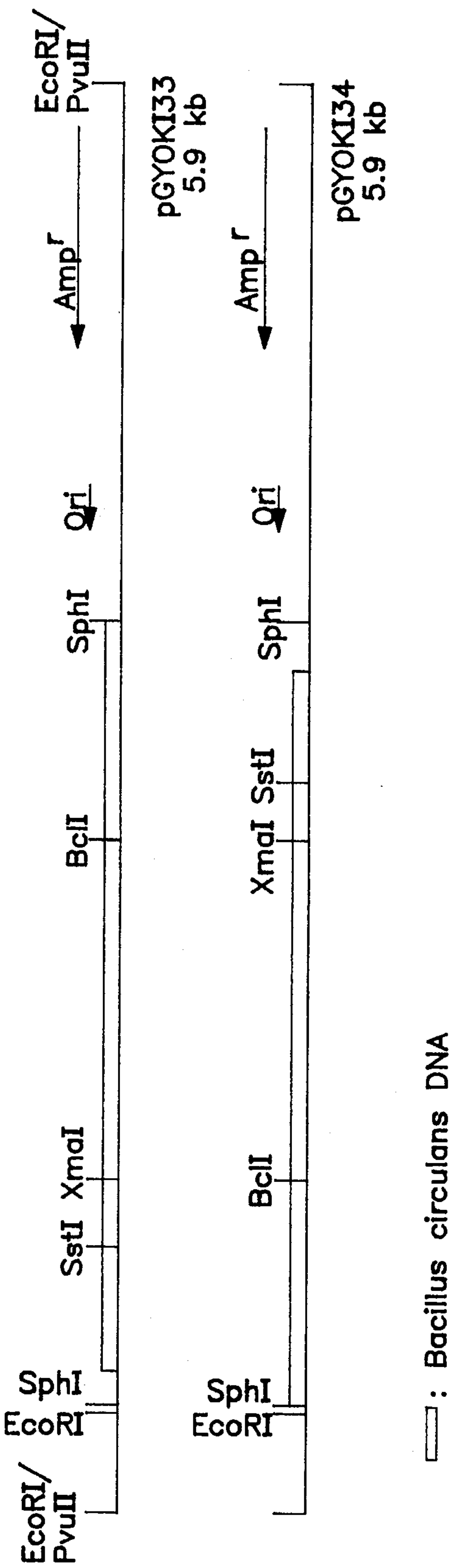
FIG. 6 is a schematic representation of the process used for producing the pGYOKI33 and pGYOKI34 vector DNAs.

The obtained $Amy^+$ colonies were propagated and plasmid DNA was isolated from them by miniprep method described in Example 1B. Thereafter the plasmid was digested by PstI restriction endonuclease (New England Biolabs., USA) using the process of the manufacturer, furthermore the DNA fragments of $Amy^+$ in two different orientations from the pUC19 plasmid were prepared by gel electrophoresis method described in Example 2F. The obtained clones were called GY1095 (pGYOKI-33) and GY1095 (pGYOKI-34). FIG. 6 shows their physical and functional maps.

EXAMPLE 3

Production of Amylase-Hirudin Expression/Secretion Cassettes

Plasmid DNA was isolated from *E. coli* JM109 (pUC19::H207 Asp) (Example 1B) and *E. coli* GY1095 (pGYOKI-34) strains (Example 2J) by maxiprep method (Example 1B). The pUC19::H207 Asp plasmid was digested by using KpnI, the pGYOKI-34 plasmid by KpnI, EcoRI and BclI restriction endonucleases (New England Biolabs., USA) according to the circumstances described by the manufacturer. After extracting them by phenol (Example 1B) they were ligated with T4 DNA ligase (New England Biolabs., USA) using the instruction of the manufacturer, thereafter the ligate was transformed into *E. coli* competent cells (Example 1B). Miniprep was made (Example 1B) from the $Amp^R$ colonies.

The identity of clones containing DNA derived from *Bacillus circulans* and synthetic hirudin gene, joined together in proper orientation, was confirmed by PstI restriction enzyme analysis (Example 2J).

The desired constructions were transformed into *E. coli* GY1095 cells (Example 1B) and plasmid DNA was isolated from these cells, too (Example 1B). The strain was called *E. coli* GY1095 (pUC19-AH). To construct the GY1095 (pUC19-deltaAH) deletion plasmid the aforesaid construction was partially digested with ClaI and totally with AccI. After ligation, transformation, plasmid isolation by miniprep method and restriction analysis the desired construction having only one ClaI cleavage site was chosen. DNA was isolated from this clone by maxiprep method (Example 1B), the DNA was digested with ClaI (New England Biolabs., USA) according to the instructions of the manufacturer, subsequently it was treated with Bal31 exonuclease (BRL, USA) according to the method of the manufacturer to reach a deletion ranging from 10–100 nucleotides in length. Thereafter it was treated by Mung Bean nuclease (Pharmacia, Sweden) using the instructions of the manufacturer, finally it was ligated (Example 3). The pUC19::H16 (FIG. 7) expressing and secreting hirudin can be found in this ligation mixture.

EXAMPLE 4

Expression of Hirudin in *E. coli*

Figure 8:
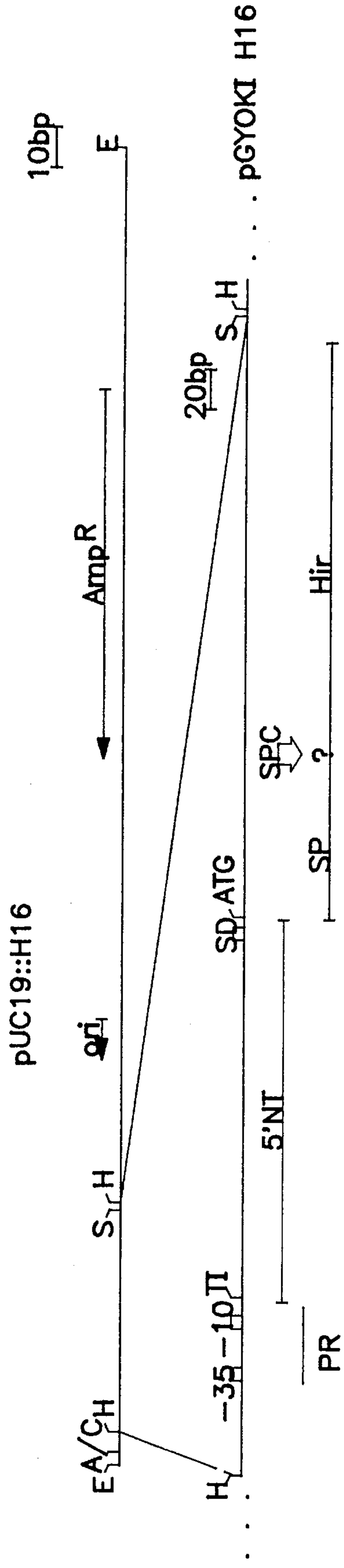
FIG. 8 is the schematic representation of a part of pGYOKI1-H16 plasmid. The H16 sequence was cloned from pUC19::H16. The abbreviations of the Figure are the same as in FIG. 7. SPC denotes the supposed cleavage site for endopeptidase.

4.A. Hirudin expression by means of *E. coli* JM109 (pUC19::H16) strain (FIG. 8)

*E. coli* JM109 competent cells were transformed (Example 1B) with the final ligation mixture described in Example 3 and the transformed bacteria were plated onto LBa medium containing 50 μg/ml of ampicillin. The developed colonies were inoculated in 5 ml LB liquid medium containing 50 μg/ml of ampicillin and shaken for 16 hours at 37° C. The hirudin activity of the culture was determined by blood test and Chromozym method (see Example 9). One of the culture showing hirudin-like activity was called *E.*

*coli* JM109 (pUC19::H16). The strain was deposited under the accession number NCAIM (P)B 1170. The pUC19::H16 sequence was analyzed by Sequenase version 2.0 kit (United States Biochemical, USA) according to the instructions of the manufacturer, and computer analysis of the sequence predicted the proper joining point of signal sequence and structural gene. This was also supported by sequencing hirudin protein (see Example 11).

FIG. 7 is the nucleotide sequence of H16.

4.B. Hirudin expression in *E. coli* JM109 (pUN121::H16) strain

Plasmid DNAs were isolated from *E. coli* JM109 (pUC19::H16) and GY1095 (pUN121) [accession number: NCAIM (P)B 1163] strains using the maxiprep method given in Example 1B and both of them were digested with HindIII (New England Biolabs., USA) enzyme according to the method of the manufacturer.

The isolated DNAs were mixed, precipitated, ligated and transformed into *E. coli* JM109 competent cells (Example 1B). The transformed cells were plated onto LBa medium containing 15 μg/ml of tetracycline and incubated for 20 hours at 28° C. Plasmid DNA was isolated by miniprep method from TcR derivatives, after that the pUC121 construction containing the H16 insert was selected using PstI digestion according to the method described in Example 1B, and the hirudin-like activity was controlled (Example 9). The producer strain was called *E. coli* JM109 (pUN121::H16) and it was deposited under accession number NCAIM (P)B 1176.

Figure 9:
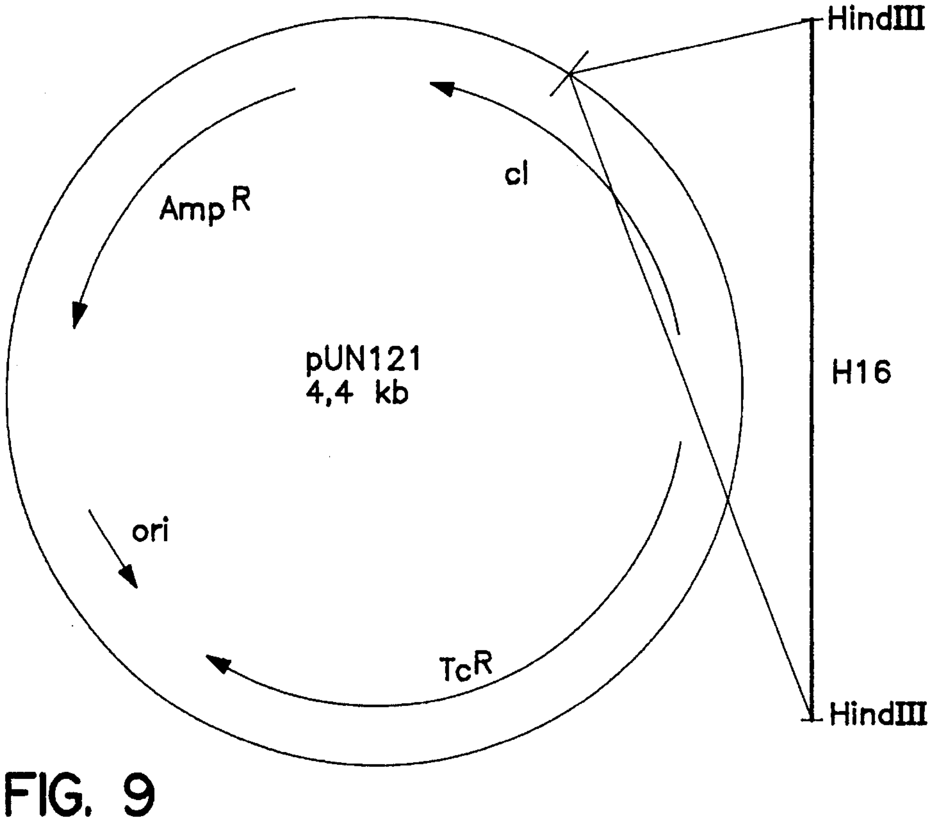
FIG. 9 is a schematic map of pUN121::H16 vector.

FIG. 9 shows its physical and functional map.

4.C. Expressing hirudin by artificial operon

In order to get the H16 expression/secretion cassettes in easily clonable form, different kinds of subclonings were carried out. Plasmid DNA was isolated from JM109 (pUC19::H16) strain described in Example 4A, using the maxiprep method disclosed in Example 1B. *E. coli* JM109M13mp18 strain (New England Biolabs., USA) was maintained according to the method described in Example 2C, with the difference that the strain was grown on 2TY medium at 37° C. without ampicillin.

Double-stranded phage DNA was isolated from the *E. coli* JM109 (M13mp18) strain by the maxiprep method described in Example 1B, with the difference that the *E. coli* JM109 (M13mp18) strain was incubated in 1l LB liquid medium. The pUC19::H16 plasmid DNA and the M13mp18 double-stranded phage DNA were digested with HindIII (New England Biolabs., USA) restriction endonuclease according to the instructions of the manufacturer. The two digested DNA samples were mixed and precipitated with ethanol and the precipitate was redissolved in the ligation mixture. After ligation it was transformed into *E. coli* JM109 competent cells using the method of Example 1B. After transformation phages were sought on solid medium. For this process 100 μl of JM109 culture grown in M9 medium (see its composition above) for 48 hours, 25 μl of 0.1M IPTG and 25 μl of 2% X-gal were added to 2.5 ml of top layer agar H melted to 42° C. To prepare the top agar H 10 g of tryptone (Bacto) and 8 g of NaCl were dissolved in 1l of distilled water, 8 g of agar (Bacto) were added and it was sterilized for 30 min. at 121° C. 100 μl of transformation mixture were added to the thus-obtained melted agar, and after mixing it was immediately poured and evenly spread onto H medium. The H medium was prepared in the same way as top agar H, with the exception that it contained 18 g of agar, instead of 8 g.

The top agar was solidified for 5 min. at room temperature, afterwards it was incubated for 16 hours at 37° C. After incubation white and blue plaques could be found on the plates. The white plaques were picked by using toothpicks and incubated into 2 ml of fresh 2TY liquid medium containing 100-fold diluted *E. coli* JM109 cells. The phages were propagated for 6 hours at 37° C. under vigorous shaking. To check the presence of H16 cassette in our recombinant M13mp18 phage, double-stranded phage DNA was isolated from the cultures using the method given in Example 1B; the cultures were screened by the blood test described in Example 9. The isolated DNA was digested with EcoRI and HindIII (New England Biolabs., USA) applying the method of the manufacturer. Double-stranded phage DNA was isolated from the foregoing recombinant M13mp18-H16 and plasmid DNA from the *E. coli* pop 2136 (pEX1) (Boehringer Mannheim Biochemical) strain using the maxiprep method of Example 1B, with the difference that the M13mp18-H16 was propagated in 1 l of fresh liquid LB medium for 16 hours at 37° C., inoculated with 10 ml of JM109 culture grown in 2TY medium containing the picked plaque. The pop 2136 pEX1) strain was cultivated at maximum 28° C.

The pop 2136 (pEX1) strain was maintained according to the method described in Example 2C. The isolated DNAs were digested with HindIII (New England Biolabs., USA) enzymes according to the instructions of the manufacturer. The two digests were mixed, precipitated, ligated and transformed into pop2136 competent cells applying the methods given in Example 1B, with the difference that the pop2136 (pEX1) strain was cultivated at 28° C. The transformed cells were plated onto LBa medium and incubated for 20 hours at 28° C.

Figure 10:
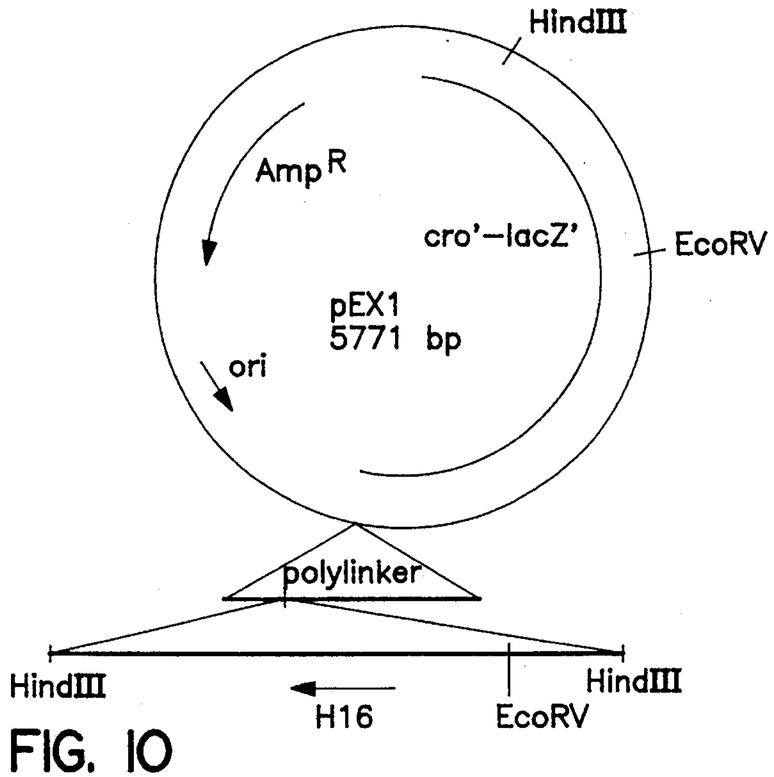
FIG. 10 is a schematic map of pEXl::H16 vector.

The H16 derivative, which was cloned into the HindIII polylinker site of pEX1 in the orientation corresponding to the β-galactosidase, was selected from the AmpR derivatives by PstI enzyme digestion (New England Biolabs., USA). The resulting strain was designated *E. coli* pop2136 (pEX1-H16). FIG. 10 shows the physical and functional map of the plasmid. Plasmid DNA was isolated from the said strain by the maxiprep method given in Example 1B, then it was digested with EcoRV endonuclease (New England Biolabs., USA) according to the procedure provided by the manufacturer. Thereafter it was precipitated, ligated and transformed into pop 2136 [NCAIM P(B) 1161] competent cells. Subsequently the transformants were plated and handled according to the method described in Example 1B. The resulting strain carrying the artificial operon was called pop2136 (pEXl::H16 deltaEcoRV) and deposited under accession number NCAIM P(B) 1165.

EXAMPLE 5

Production of β-Galactosidase-Hirudin Fusion Protein

Different subclonings were accomplished to ensure the preferred cloning of synthetic hirudin gene. Plasmid DNA was isolated from *E. coli* JM109 (pUC::H207 Asp) strain described in Example 1 by maxiprep method (Example 1B). Double-stranded phage DNA was isolated from *E. coli* M13mp18 strain by maxiprep method (Example 1B). The isolated double-stranded phage DNA was digested with EcoRI and HindIII enzymes (New England Biolabs., USA) and the H207 Asp cassette was subcloned into M13mp18 vector in the way as described in Example 4C. The clone was named M13mp18::H207 Asp. These subcloning experimental steps were repeated, with the difference that the donor construction was M13mp18::H207 Asp, while the recipient was pBLUESCRIPT KS$^+$ (Stratagene). After transformation the cells were plated onto LB medium containing 50 μg/ml of ampicillin, without JM109 cells. From the blue and white colonies a white one was inoculated into 3 ml of LB medium containing 50 μg/ml of ampicillin. After intensive shaking for 16 hours at 37° C. plasmid DNA was isolated by the miniprep method and it was checked by EcoRI-HindIII double digestion for the presence of H207 Asp gene.

Figure 11:
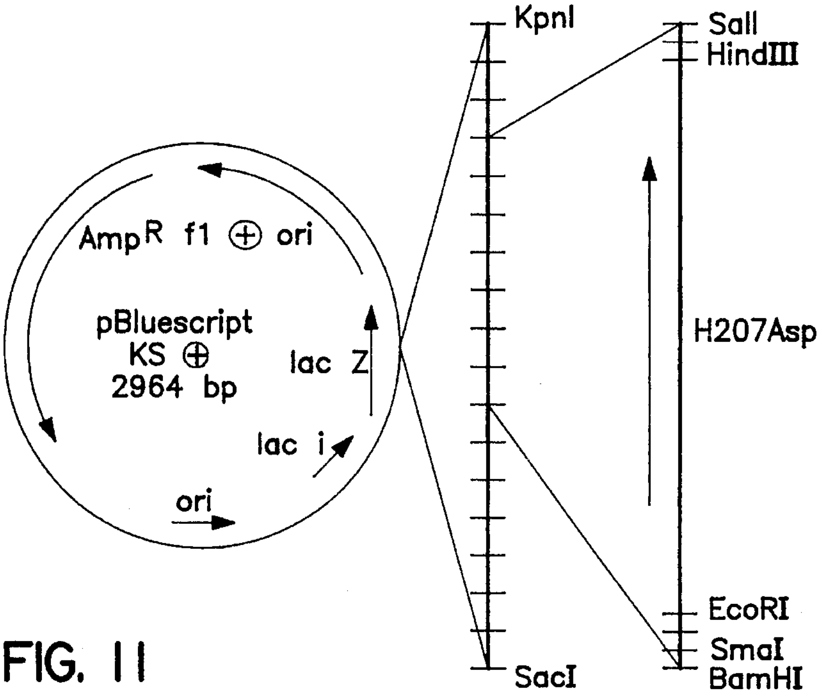
FIG. 11 is a schematic representation of a process for cloning hirudin HV-1 sequence into pBluescript KS+ vector DNA.
Figure 12:
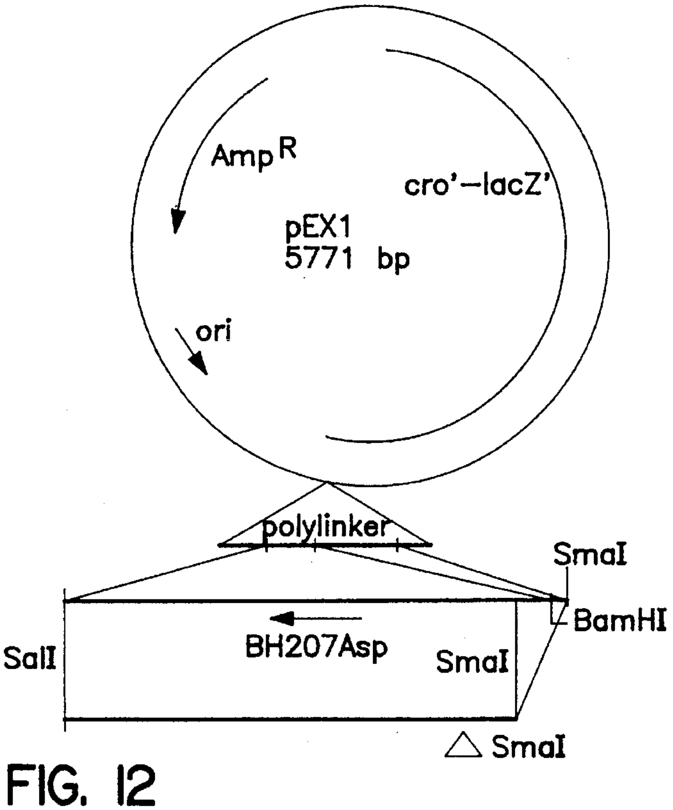
FIG. 12 is a schematic representation of a process for producing vector DNA to express β-galactosidase-hirudin fusion protein.

The desired clone was designated *E. coli* JM109 (pBLUESCRIPT KS+::H207 Asp). FIG. 11 shows its physical and functional map. The same subcloning steps were repeated but in this case the donor construction was JM109 (pBLUESCRIPT KS+::H207 Asp), whereas the recipient was M13mp18 and the cleavage enzymes were BamHI and SalI. After transformation the cells were plated onto M-medium together with *E. coli* JM109 cells. The white plaques were incubated from the developed white and blue plaques. After vigorous shaking for 16 hours at 37° C. double-stranded phage DNA was isolated by the miniprep method and it was checked for the presence of H207 Asp gene by EcoRI-HindIII digestion. The clone was called pop2136 (pEX-1::BH207 Asp). FIG. 12 shows its physical an functional map.

Plasmid DNA was isolated from this clone by the maxiprep method given in Example 1B, after that it was digested with SmaI enzyme (New England Biolabs., USA) according to the instruction of the manufacturer, then it was precipitated, ligated and transformed into pop2136 competent cells. Plasmid DNA was isolated from the culture of developed colonies and the DNA was digested with BamHI (all steps were carried out according to Example 1B). The construction, which could not be digested with BamHI, was called *E. coli* pop2136 (pEX1::BH207 Aspfp). The strain was deposited under accession number NCAIM P(B) 1169.

The correctness of the construction was controlled by sequenation. For this operation control plasmid DNA was isolated from pop2136 (pEX1::BH207 Aspfp) strain by maxiprep method (Example 1B) and the BH207 Asp construction was subcloned into M13mp19 phage vector (New England Biolabs., USA) by using HindIII enzyme.

The construction was sequenced in the aforesaid vector by using Sequenase version 2.0 kit (United States Biochemical, USA) according to the procedure described by the manufacturer. From the analysis of the received sequence it turned out that the hirudin was joined in frame with β-galactosidase, consequently the production of fusion protein is guaranteed. To increase the ratio of hirudin in the fusion protein PvuII-SmaI and EcoRI-SmaI deletions were similarly constructed as in the case of pop2136 (pEXl::BH207 Aspfp), with the difference that, in addition to SmaI, PvuII digestion (New England Biolabs., USA) and EcoRV digestion, respectively, were applied according to the instructions of the manufacturer. One of the thus-obtained strains was designated *E. coli* pop 2136 (pEX1::BH207 AsndeltaEcoRV-SmaI) and it was deposited under accession number NCAIM (P)B 1177 (see also Examples 10 and 11).

EXAMPLE 6

Hirudin Expression in Saccharomyces Cells

6.A. Construction of Saccharomyces expression/secretion cassettes

6.A.a) Production of YpGYOK1 and YpGYOK2 vectors

To express and secrete hirudin by *E. coli* —Saccharomyces bifunctional vector we took those nucleotide sequences into consideration which comprise:

- the URA3 and leu2-d genes,
- the replication origins of *E. coli* and Saccharomyces,
- the bacteriophage $f_1$ origin for in vitro oligonucleotide-mediated mutagenesis to the formation of single-stranded DNA,
- the transcriptional and translational regulators operating in Saccharomyces (e.g.: enhancer, promoter, secretion signal, transcription terminator).

The starting plasmids are the 3.2 kb *E. coli* pBS(±) (Stratagene) and the Saccharomyces pJDB207 [*E. coli* MC1061 (pJDB207) (NCAIM P/B/ 1184)] plasmids. The pBS(±) plasmid carries the $f_1$ replication origin and the gene conferring ampicillin resistance. The pJDB207 comprises the ori gene and the transcription terminator of FLP gene of two-micron yeast plasmid on a 3.22 kb long nucleotide fragment; furthermore, it contains the leu2-d gene. A 1.6 kb long fragment from the G2 plasmid [*E. coli* MC1061 (GYOKI-pG-2) (NCAIM/P/B 1183)] carries the URA3 gene and the GAL1 -GAL10 intergenic region.

At the planning of the YpGYOK1 plasmid we took into consideration the pX promoter isolated by our promoter-probe plasmid from Saccharomyces. To design signal sequence we took the gene fragment encoding the leader peptide of *Kluyveromyces lactis* into consideration as starting substance, that was in vitro synthesized on the Applied Biosystem Cyclone DNA-synthesizer using the methods of Example 1 and the instructions of the manufacturer. The following nucleotide sequence was synthesized (SEQ ID NO:1 ) ATG AAT ATA TTT TAC ATA TTT TTG TTT TTG CTG TCA TTC GTT CAA GGT ACC CGG GGA.

Figure 18:
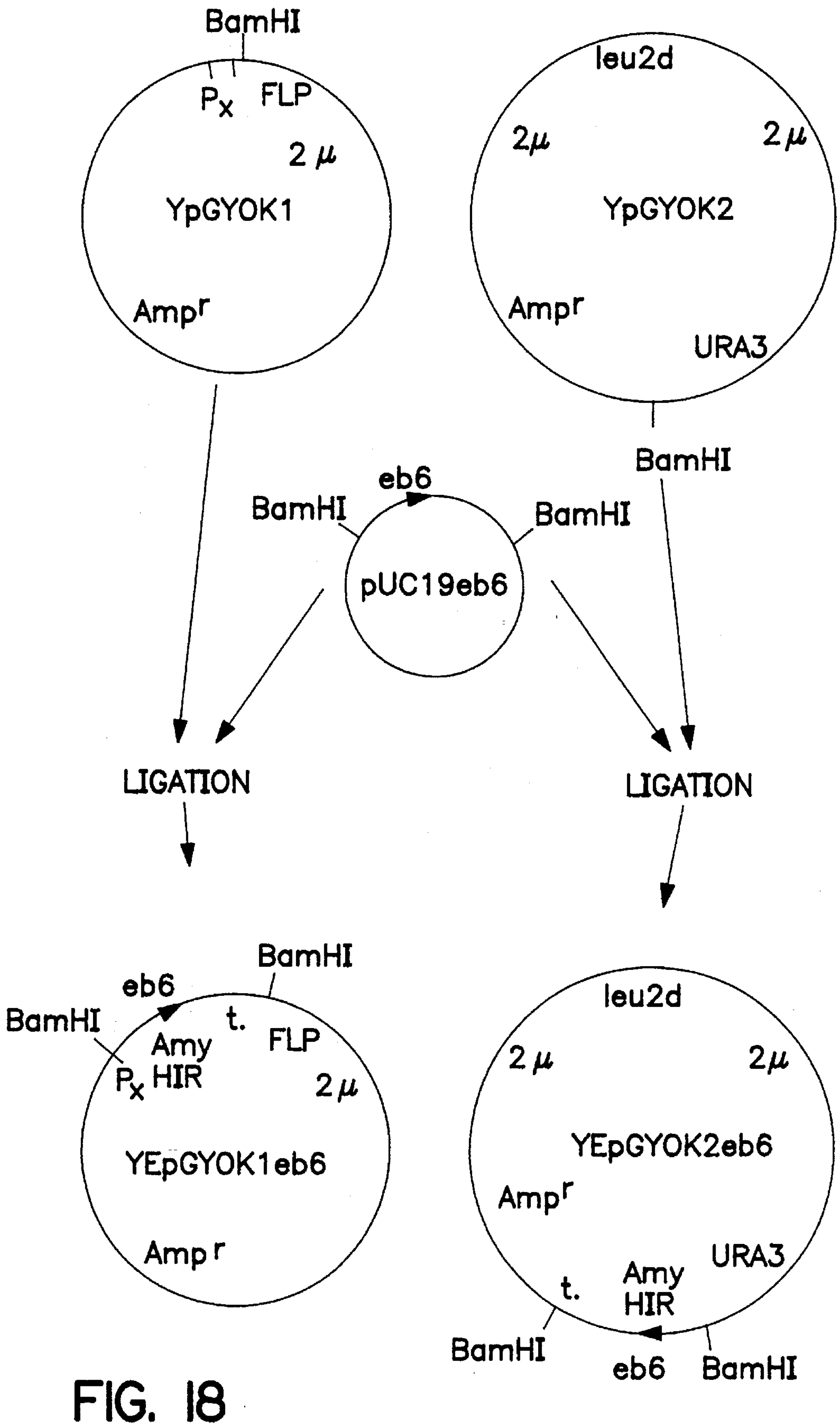
FIG. 18 represents the process used for the production of YEpGYOK1eb6 and YEpGYOK2eb6 vector DNAs.

The aforesaid gene fragment and the polylinker sequence of M13mp19 phage vector were also inserted. The latter contains the following restriction cleavage sites: XhoI, SacI, SmaI, BamHI, SalI, HindIII. After restriction digestion using the instructions of the manufacturer the fragments were isolated by electroelution and ligated, subsequently the *E. coli*—Saccharomyces plasmid was isolated and named YpGYOK1. The *E. coli* strain containing the said plasmid was deposited under accession number NCAIM (P)B 1166. FIG. 18 shows the partial restriction and functional map of YpGYOK1 plasmid.

The YpGYOK2 plasmid comprises the total two-micron sequence, in contrast to YpGYOK1 vector. FIG. 18 shows its partial restriction and functional map. The *E. coli* strain carrying the YpGYOK2 plasmid was deposited under accession number NCAIM (P)B 1167.

6.A.b) Production of YpGYOK1HN and YpGYOK1HP

The *Escherichia coli* JM109 [pUC19::H207 Asp (NCAIM /P/B 1171)] and the *Escherichia coli* JM109 [pUC19::H221 Asn (NCAIM P/B 1175)] strains (produced in the above-described way) contain the synthetic hirudin structural gene cloned between Kpn-SphI restriction sites. The about 0.2 kb long fragment comprising the hirudin gene was cleaved from isolated plasmid DNA (the method was given above) by SacI and HindIII restriction endonucleases (Amersham) according to the instruction of the manufacturer. Thereafter it was separated by gel electrophoresis in 1.8% of agarose, subsequently the desired fragment was cut out and electroeluted in dialysis bag. After extraction with chloroform the DNA was precipitated with ethanol and redissolved in 10 μg of distilled water.

YpGYOK1 plasmid was isolated from *E. coli* (see above in Example 6Aa) and the DNA was digested with BamHI and HindIII enzymes (Amersham) using the method of the manufacturer. After separation by gel electrophoresis and purification (see above) the 8.9 kb long fragment was redissolved in distilled water.

3 μl of the 0.2 kb long SacI-HindIII fragment and 3 μl of the 8.9 kb long BamHI-HindIII fragment were mixed and ligated (T4 DNA ligase, Boehringer Mannheim GmbH., Germany) according to the instruction of the manufacturer by joining the BamHI and SacI sticky ends with a synthetic adapter produced by the method given in Example 1. The nucleotide sequence of the aforesaid adapter is:

(SEQ ID NO:2) 5'-GATCCGGGCCCTGTTAGAGCT-3'

(SEQ ID NO:3) 3'-GCCCGGGACAATC-5'

After ligation the *E. coli* MC1061 cells (Pharmacia LKB) were transformed using the method given above. After the introduction of hirudin structure, in the DNAs of the obtained YpGYOK1HN and YpGYOK1HP vectors the following nucleotide sequence was formed by joining with the region encoding signal sequence:

Met Asn Ile Phe Thr Ile Phe Leu Phe Leu Leu Ser Phe
ATG AAT ATA TTT TAC ATA TTT TTG TTT TTG CTG TCA TTC

Val Gln Gly thr arg gly ser gly pro cys STOP
GTT CAA GGT ACC CGG GGA TCC GGG CCC TGT TAG AGC TCG
KpnI BamHI ApaI SacI GTA CCT GGC CAT GGT-HIRUDIN-TA GTA AGC ATG CAA GCT T
SphI HindIII The adapter sequence is underlined and the amino acid sequence of the disadvantageous gene part is denoted by small letters. The nucleic acid sequence before "HIRUDIN" is SEQ ID NO: 4 and the nucleic acid sequence after "HIRUDIN" is SEQ ID NO: 5.

Figure 13:
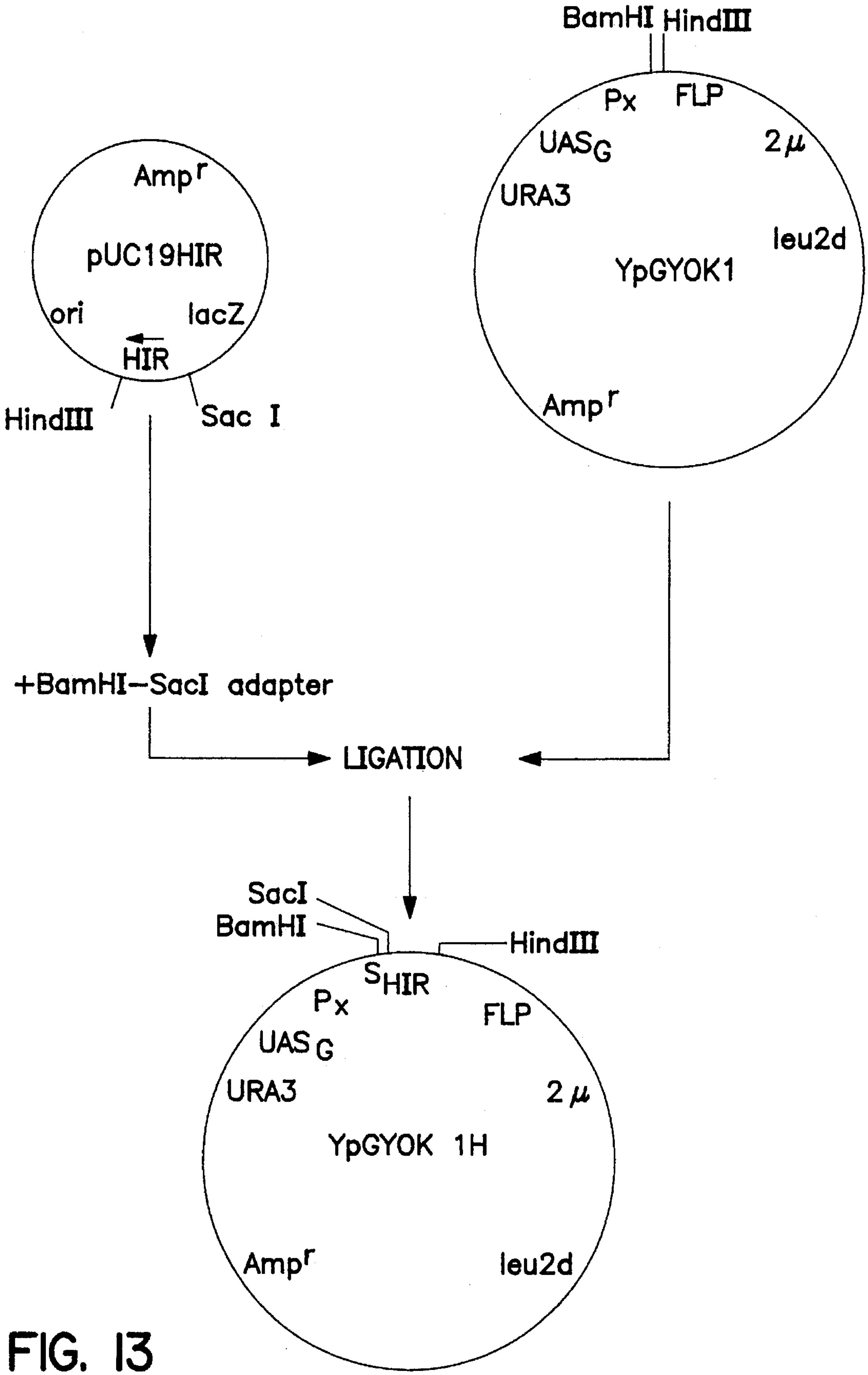
FIG. 13 is a schematic representation of a process used for producing YpGYOK1H vector DNA.
Figure 14:
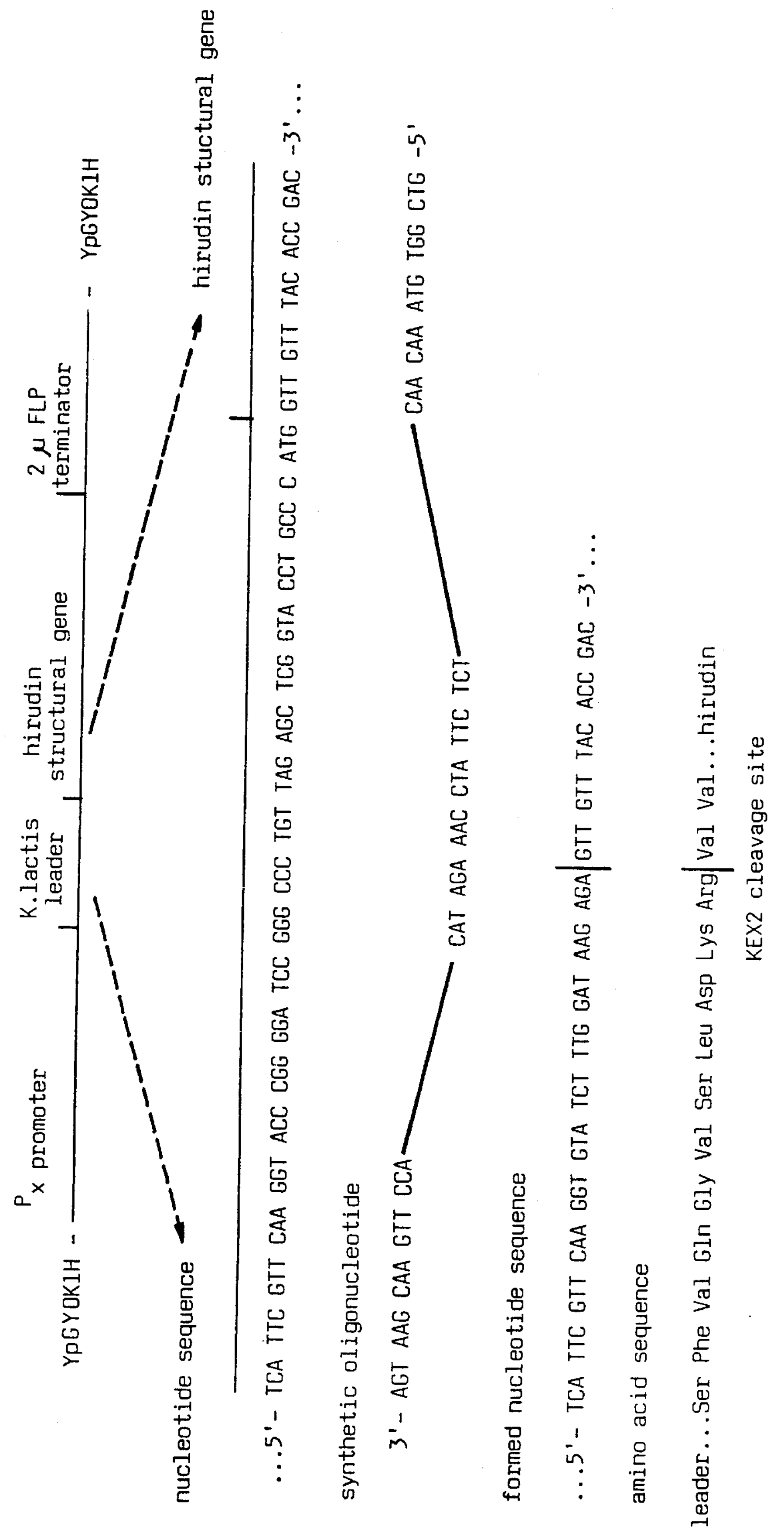
FIG. 14 is a schematic representation of a process applied for oligonucleotide-mediated mutagenesis.

The Saccharomyces vectors containing hirudin gene encoding aspartic acid or asparagine at the 33 position, which have also been controlled by restriction mapping, are designated YpGYOK1HP and YpGYOK1HN, respectively. FIGS. 13 and 14 give the schematic representation of the procedures used for producing the aforesaid plasmids.

6.A.c) Construction of YEpGYOK1H and YEpGYOK1HP

The hirudin gene is not in frame with the nucleotide sequence encoding signal peptide, furthermore, the exact cleavage site for hirudin from the signal peptide can not be foretold. In vitro oligonucleotide-mediated mutagenesis can be used to adjust the proper reading frame and to form the cleavage site for signal peptidase upstream of the hirudin N-terminal. To the mutagenesis, Bio-Rad (Richmond, Calif., USA) MUTA-GENE kit was applied following the instructions of the manufacturer, 6.A.ca) Preparation of single stranded DNA of YpGYOK1H comprising uracil instead of thymine

*E. coli* CJ236 cells (see the kit) were transformed with YpGYOK1HN and YpGYOK1HP vector DNAs (see Example 6Ab) according to the procedure given above. The mutant cells of the said strain incorporate uracil with great frequency, instead of thymine, into the DNA. Single-stranded DNA comprising uracil instead of thymine was isolated from *E. coli* CJ236 (YpGYOK1H) strain using the following method.

*E. coli* K12 CJ236 (YpGYOK1H) culture grown overnight was inoculated into 20 ml of LB medium containing 30 μg/ml of chloramphenicol and 100 μg/ml of ampicillin. After incubating for 6 hours in a 37° C. shaker it was transfected with 1–3×$10^6$ pfu (50 μl) of M13R408 helper phage, finally it was incubated for a night in a shaker at 37° C. In the supernatant of the culture the phage particles contain the single-stranded YpGYOK1H DNA, instead of the genome of M13 phage.

After removing the cells from the culture broth by centrifugation the phages were precipitated from the supernatant by using ammonium acetate (at 0.7M final concentration) and polyethylene glycol 8000 (at 4% final concentration). The phage precipitate was suspended in TE buffer, then it was extracted with phenol. In the presence of ethylenediamine-tetraacetic acid the protein coat of phages can open, therefore it is suitable to remove it by phenol extraction. The single-stranded DNA of YpGYOK1H containing uracil instead of thymine was precipitated with ethanol (in 2.5-fold volume) and redissolved in TE buffer.

6.A.cb) The mutagenic oligonucleotide

The following 48-mer synthetic oligonucleotide was employed to the in vitro mutagenesis. The oligonucleotide was produced by using the method described above.

5'-GTC GGT GTA AAC AAC TCT CTT ATC CAA AGA TAC ACC TTG AAC GAA TGA-3' (SEQ ID NO:6)

The underlined segments correspond to the first 5 amino-acid residues of hirudin in YpGYOK1H vector and to the last 5 amino-acid residues of *Kluyveromyces lactis* secretion signal peptide (see also FIG. 14).

In the resulted vector DNA reconstructed by oligonucleotide-mediated mutagenesis the following elements can be found one after the other: the segment coding for the *Kluyveromyces lactis* signal peptide, the DNA sequence encoding the last 4 amino-acid residues of the α-factor prepro-leader in α-mating type yeasts and the nucleotide sequence of the cleavage site of KEX2 endopeptidase coding for lysine and arginine. The mutagenic oligonucleotide is suitable both to adjust the translational reading frame between the hirudin gene and signal peptide sequence and to form the signal peptidase cleavage site at the N-terminal part of hirudin.

6.A.cc) Creating the double-stranded form of YpGYOK1H vector, lacking uracil residues in its copy strand, from the single-stranded form of the said vector DNA containing uracil instead of thymine, using the mutagenic oligonucleotide 200 pM of mutagenic oligonucleotide (see Example 6Acb), 3 μl of 1M Tris.Cl (pH 8.0), 1.5 μl of 0.2M magnesium chloride, 1.5 μl of 0.1M DTT and 13 μl of 1 mM ATP were adjusted to 30 μl with distilled water. After mixing them 4.5 units of T4 polynucleotide kinase enzyme (see above) were added and the reaction mixture was incubated for 45 min. at 37° C. The reaction was blocked by heat inactivation at 65° C. for 10 min.

0.1 pM of the foregoing phosphorylated mutagenic oligonucleotide, 100 ng of single-stranded YpGYOK1H vector DNA containing uracil instead of thymine, 20 mM of magnesium chloride and 50 mM of NaCl were added to 9 μl of the mixture and after mixing it was incubated at 65° C. for 5 min. The mixture was then continuously cooled to room temperature for about 40 min.

The complementer strand of YpGYOK1H vector DNA was in vitro synthesized using the annealed mutagenic oligonucleotide as a primer on the single-stranded form of the foregoing vector.

Since uracil was not added to the extension reaction (only thymine), therefore the complimentary strand synthesized in vitro could not contain uracil residues. 9 μl of single-stranded vector DNA containing annealed oligonucleotide; 3 μl of a solution containing all four dNTPs, each at a concentration of 2.5mM; 0.5 μl of a solution comprising 10 mM ATP, 0.1M Tris.Cl (pH 7.4), 0.05M magnesium chloride and 0.02M DTT; 2 units of T4 DNA ligase (see above) and 1.5 μl (2 units) of T4 DNA polymerase were added. This reaction mixture was incubated first for 5 min. in ice water bath, then for 120 min. at 37° C. After adding 40 μl of TE buffer the mixture was frozen. In the resulting reaction mixture there are hybrid double-stranded DNAs, in which one strand contains uracil residues instead of thymine and the joining part of the secretion signal sequence and the hirudin corresponds to the description of Example 6Acb, while in the other strand the sequence of the joining segment between secretion signal and hirudin corresponds to the sequence of the mutagenic oligonucleotide.

6.A.cd) Final steps for producing YEpGYOK1HN and YEpGYOK1HP DNA vectors suitable for the expression and secretion of hirudin The hybrid, double-stranded DNA vector produced according to the method of Example 6Acc was transformed into *E. coli* K12 MV1190 (see the kit) competent cells (see above). In the cells of this strain the replication frequency of DNA containing uracil residues is low, therefore the transformants carry the mutation coded by the oligonucleotide with 50% probability. It was determined by the restriction analysis of the plasmids derived from the AmpR transformants that 2 from 5 carried the desired mutation, namely the YEpGYOK1HN plasmid, while 4 from 6 contained the YEpGYOK1HP plasmid in the other reaction mixture.

FIG. 14 is the schematic representation of the in vitro mutagenesis used for producing the foregoing plasmids.

6.A.ce) Analysis of the nucleotide sequence of YEpGYOK1H DNA vectors suitable for the expression and secretion of hirudin The joining region of the secretion signal and hirudin sequences was determined in order to control the YEpGYOK1H vector DNA obtained by in vitro oligonucleotide-mediated mutagenesis, The YEpGYOK1H vector was digested by SacI and HindIII restriction endonucleases (see above) and the 280 kb long fragment encoding hirudin was separated by gel electrophoresis, then it was isolated from the gel according to the method described above.

The M13mp19 phage vector (Stratagene) was digested with SacI and HindIII enzymes, then it was ligated with the aforesaid gene fragment. The ligation mixture was transformed into competent *E. coli* cells. The recombinant phage was selected from the transformants. The strain carrying the secretion signal-hirudin gene construction in M13mp19 was cultivated in LB medium. Single-stranded phage DNA was prepared from the supernatant of the culture using essentially the same method as described in Example 6Aca.

The nucleotide sequence of the thus-obtained single-stranded DNA was determined by Sanger dideoxy-mediated chain-termination method. According to the sequenation experiment the sequence of channel A and the readable part of channels C and D fit to the expectations. 6.A.d) Production of YEpGYOK1eb1

The YEpGYOK1HN and YEpGYOK1HP plasmids (see Example 6Ac) were digested by HindIII restriction enzyme, then they were treated with Mung Bean endonuclease (Pharmacia) (see above), subsequently the following XhoI restriction cleavage site was created by using the following adapter (product of New England Biolabs.):

5'-CCGCTCGAGCGG-3' (SEQ ID NO:7)

To form the XhoI cleavage site, the reaction mixture containing the blunt-ended DNA and the adapter was ligated by T4 DNA ligase (Boehringer Mannheim GmbH., Germany) according to the instruction of the manufacturer.

6.A.e) Production of YEpGYOK1eb2

20 μl of YEpGYOK2eb2 plasmid DNA (produced by the method described in Example 6Ai), 10 μl of E1 buffer and 68 μl of distilled water were mixed. To produce E1 buffer 500 μl of 2M Tris.Cl (pH 7.4), 1660 μl of 3M NaCl, 1000 μl of 1M magnesium chloride, 50 μl of mercaptoethanol and 6790 μl of distilled water were mixed. To the reaction mixture containing plasmid DNA 20 units of SacI and 20 units of BamHI restriction endonucleases (Amersham, England) were added, then the mixture was incubated for 16 hours at 37° C. The SacI-BamHI DNA fragment containing signal sequence, hirudin structural gene and GAPDH terminator was prepared by the method described above using gel electrophoresis and electroelution.

10 μl of E3 buffer and 61 μl of distilled water were added to 25 μl of YpGYOKI plasmid DNA (according to Example 6Aa). After adding 20 units of SacI and 20 units of BamHI restriction enzymes (Amersham, England) the reaction mixture was incubated for 16 hours at 37° C.

The resulting linear DNA molecules were extracted with phenol to remove proteins and precipitated. After the DNA molecules were desiccated in vacuo the precipitate was redissolved in 10 μl of distilled water.

3 μl of ligation buffer L, 1 μl of DTT solution, 1 μl of ATP solution and 1 μl of distilled water were added to 4 μl of each of linear DNA samples prepared by the above methods. To join the linear DNA molecules the reaction mixture was supplemented with 1 μl (2.5 units) of T4 DNA ligase (Amersham, England) and it was incubated for 16 hours at 15° C.

Figure 15:
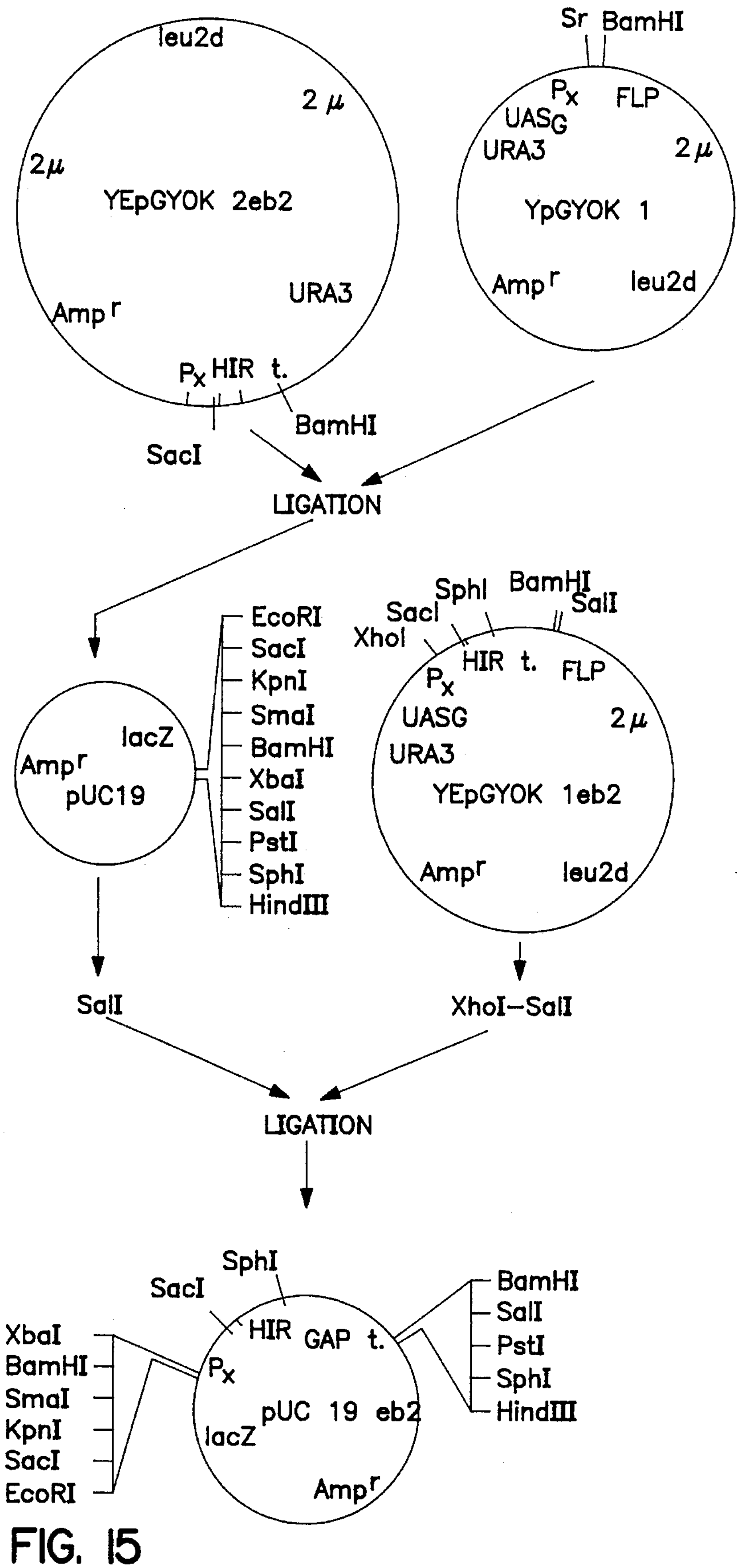
FIG. 15 represents the process used for the production of YEpGYOK1eb2 and pUC19eb2 vector DNAs.

Here YEpGYOK1eb2 circular molecule appeared in the reaction mixture and it was isolated by methods given above. FIG. 15 shows the scheme of process and the plasmids.

Figure 16:
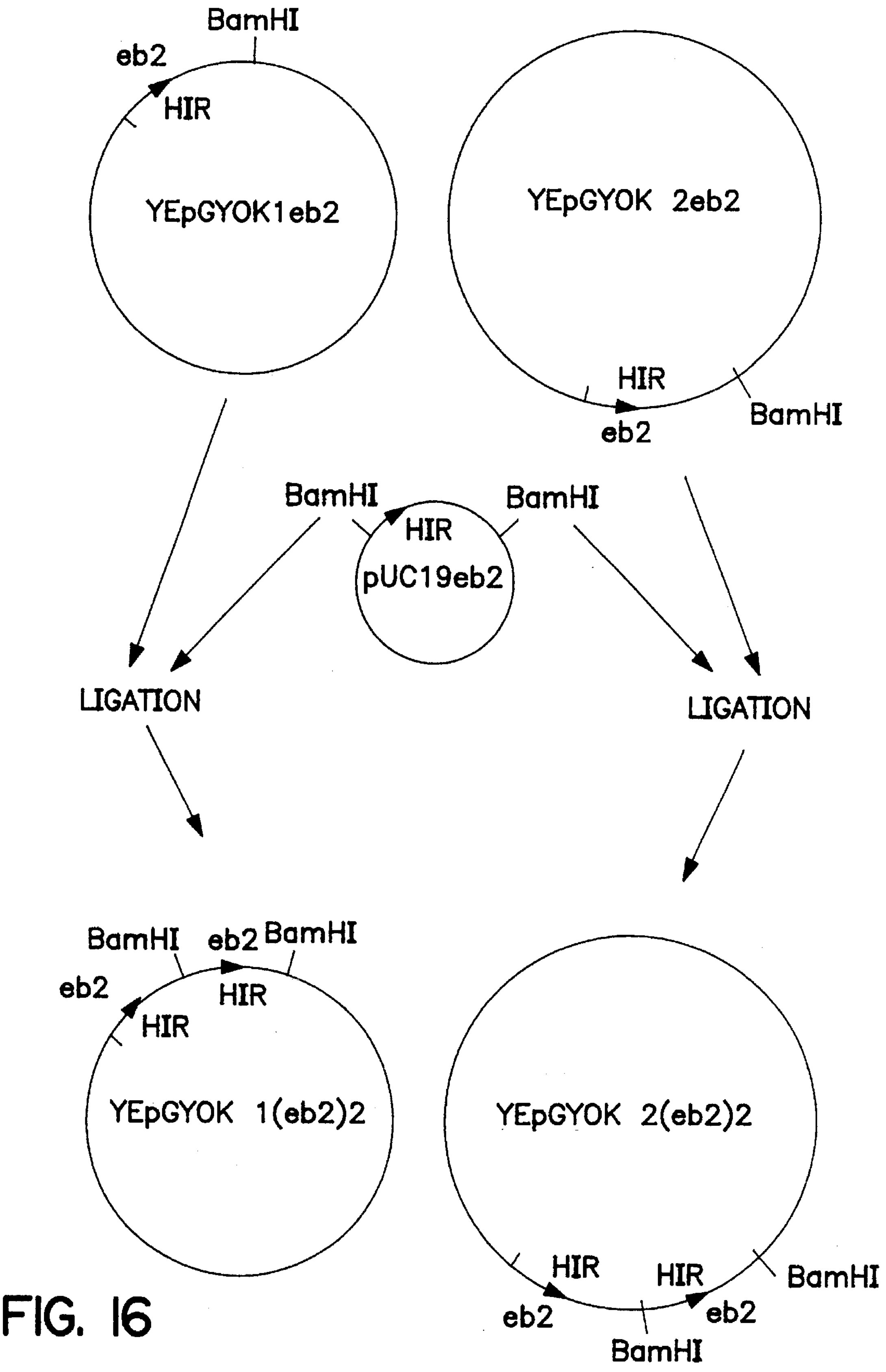
FIG. 16 represents the process used for the production of YEpGYOK1(eb2)2 and YEpGYOK2(eb2)2 vector DNAs.

6.A.f) Construction of YEpGYOK1(eb2)2 (see also FIG. 16)

6.A.fa) Production of pUC19eb2 plasmid

20 μl of YEpGYOK1eb2 plasmid DNA produced according to Example 6Ae, 10 μl of E4 buffer and 66 μl of distilled water were mixed. 20 units each of XhoI and of SalI restriction endonucleases were added to the mixture containing plasmid DNA, then it was incubated for 16 hours at 37° C. The DNA fragment containing eb2 expression cassette was isolated by agarose gel electrophoresis and electroelution using the method as above.

The pUC19 circular plasmid was linearized by SalI restriction enzyme and it was isolated by gel electrophoresis and electroelution. The linear pUC19 plasmid DNA and the DNA fragment containing the eb2 expression cassette were ligated by T4 ligase (see above). The pUC19eb2 circular DNA molecule appearing in the reaction mixture was isolated using the method described above.

6.A.fb) Production of YEpGYOK1(eb2)2

The YEpGYOK 1eb2 plasmid was linearized by BamHI restriction enzyme under the circumstances described above. The DNA fragment containing eb2 expression cassette was isolated from pUC19eb2 plasmid (see Example 6Afa) by means of BamHI restriction enzyme using the above method. The linear fragments were joined by ligation (see above).

The YEpGYOK1(eb2)2 circular DNA molecule appeared (see also FIG. 16) in the reaction mixture containing the linear fragments of YEpGYOK1eb2 DNA and the fragment carrying the eb2 expression cassette.

6.A.g) Production of YEpGYOK1eb6 (see also FIG. 18)

6.A.ga) Production of pUC19eb6 plasmid

After digesting the pUC19::H16 plasmid DNA (Example 4A) by BamHI and SphI restriction enzymes using the former method, the DNA fragment containing the promoter and signal sequence of *Bacillus circulans* α-amylase and the hirudin structural gene was isolated from the aforesaid plasmid. The DNA fragment containing no eb2 cassette was then isolated from pUC19eb2 plasmid DNA (Example 6Afa) by using BamHI and SphI enzymes to the digestion. Finally, the DNA fragment containing the GAPDH terminator was produced and isolated from pUC19eb2 plasmid DNA by SphI restriction endonuclease. The produced DNA fragments were ligated using the aforesaid methods. The pUC19eb6 circular plasmid appeared in the reaction mixture containing the three fragments.

6.A.gb) Production of YEpGYOK1eb6

Figure 17:
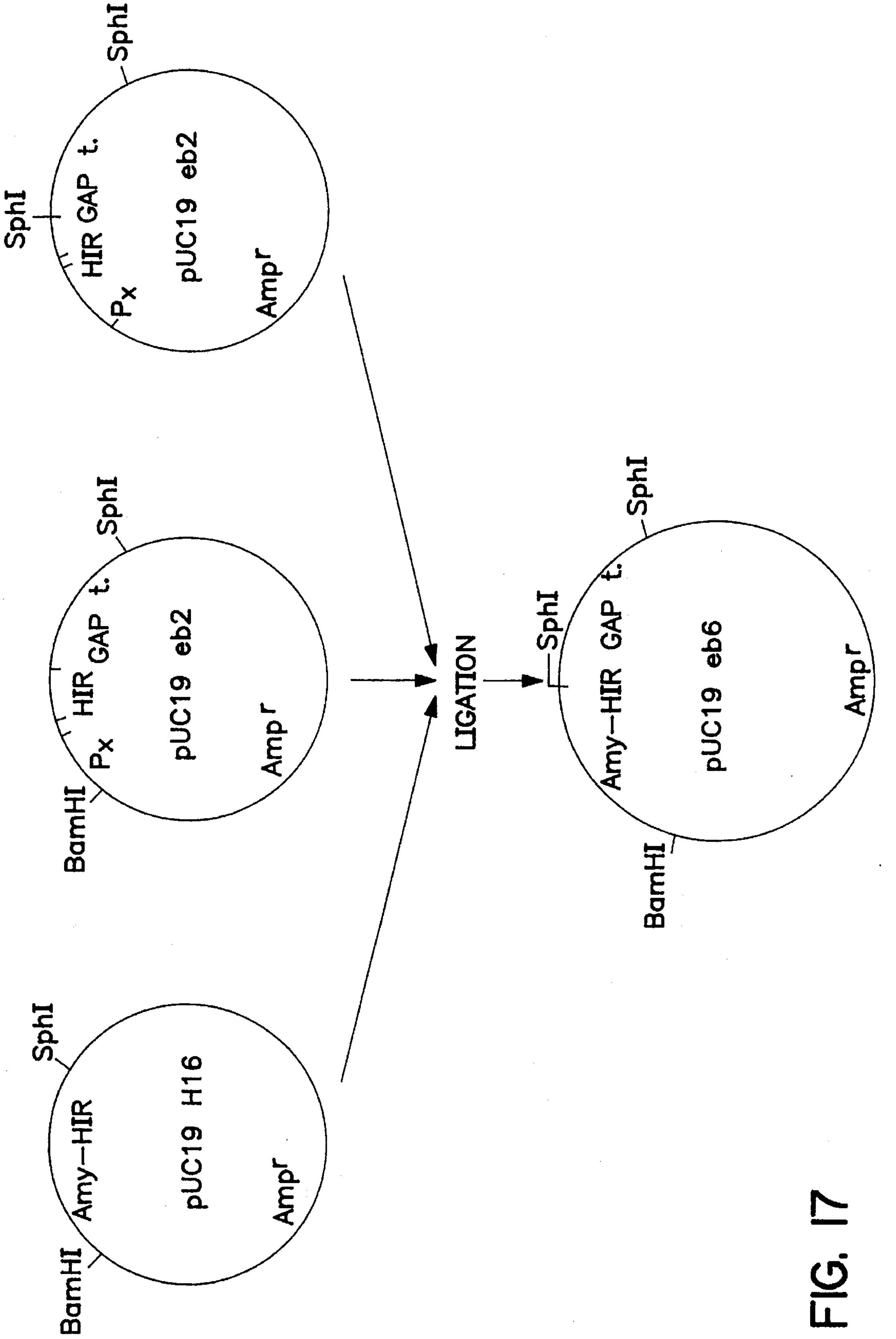
FIG. 17 represents the process used for the production of pUC19eb6 vector DNAs.

The YpGYOK1 plasmid was linearized by BamHI restriction enzyme using the described method. After that the DNA fragment containing the eb6 expression cassette was isolated from pUC19eb6 plasmid using BamHI digestion (see above). The linear DNA fragments were ligated by using the method described above. The YEpGYOK1eb6 circular DNA molecule containing the eb6 expression cassette appeared in the reaction mixture (see FIGS. 17 and 18).

Figure 19:
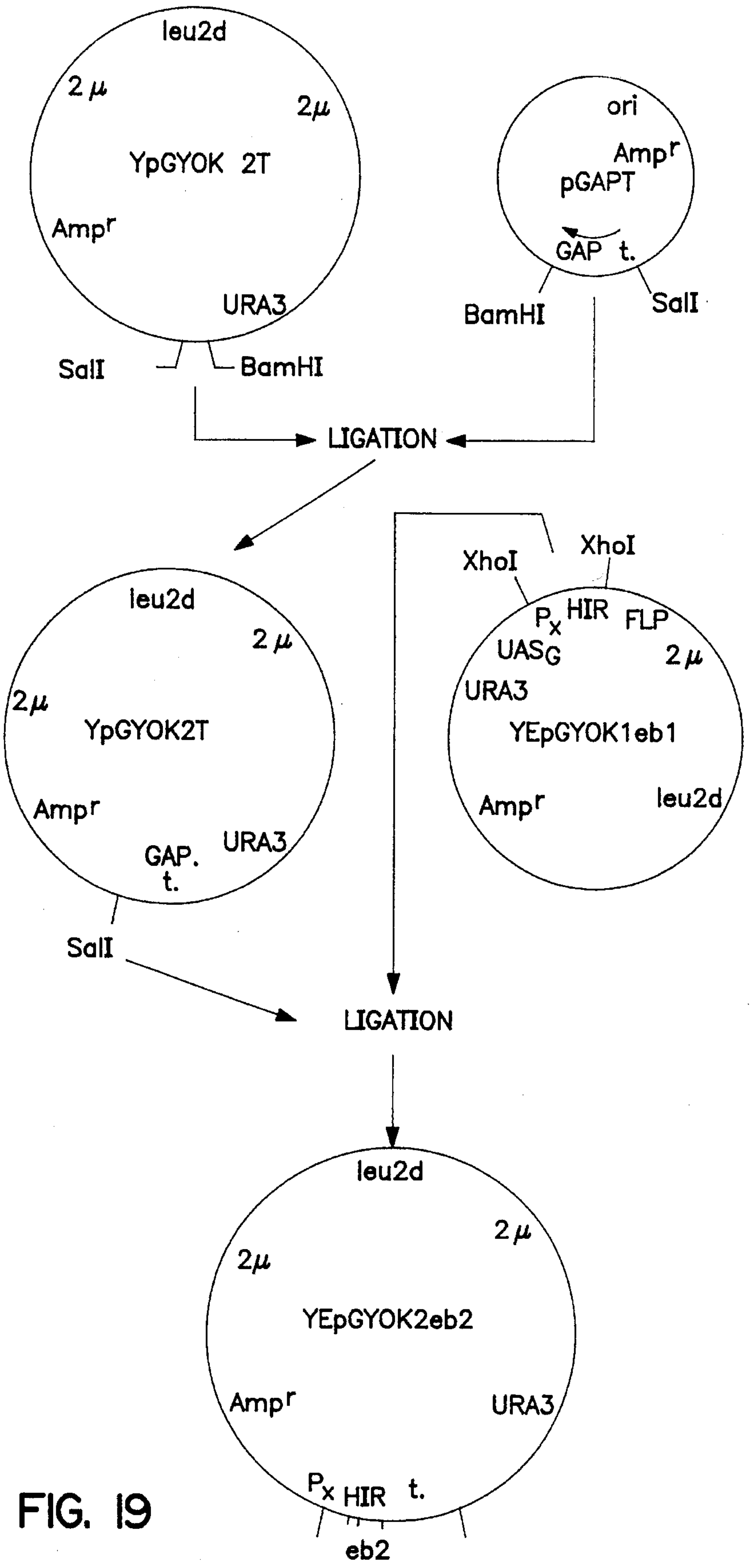
FIG. 19 represents the process used for the production of YpGYOK2T and YEpGYOK2eb2 vector DNAs.

6.A.h) Production of YpGYOK2T (see also FIG. 19)

20 μl of YpGYOK2 plasmid DNA (Example 6A), 20 μl of E4 buffer, and 156 μl of distilled water were admixed. To prepare E4 buffer 500 μ of 2M Tris.Cl (pH 7.9), 5000 μl of 3M NaCl, 1000 μl of 1M magnesium chloride, 50 μl of mercaptoethanol and 3450 μl of distilled water were mixed. 20 units each of SalI and BamHI restriction endonucleases (Amersham, England) were added to the reaction mixture containing plasmid DNA, then it was incubated for 16 hours at 37° C.

The fragments of YpGYOK2 DNA produced by using restriction endonucleases were separated by agarose gel electrophoresis. The larger DNA fragment was isolated from the agarose gel by using electroelution, then it was purified. In this way 13.2 kb long SalI-BamHI linear DNA molecule was obtained. 25 μl of pGAPT plasmid DNA [NCAIM (P)B 1164], 10 μl of E4 buffer and 61 μl of distilled water were mixed. 20 units each of SalI and BamHI restriction endonucleases (Amersham, England) were added to the reaction mixture containing the plasmid DNA, then it was incubated for 16 hours at 37° C. The linear DNA fragment containing the GAPDH terminator region, having SalI and BamHI sticky ends, was prepared from the fragments of pGAPT plasmid treated with endonucleases. To the ligation of linear DNA molecules the following solutions were utilized.

L solution: 2.5 ml of 1M Tris.Cl (pH 7.6), 2.5 ml of 0.2M magnesium chloride, and 5 ml of 50% polyethylene glycol 6000 (Fluka A. G.) are admixed and 2.5 mg of bovine serum albumin (Sigma, USA) are dissolved therein.

DTT solution: 3.09 g dithiothreitol are dissolved in 20 ml of 0.01M sodium acetate (pH 5.2) solution.

ATP solution: 60 mg of adenosine triphosphate are dissolved in 800 μl of water, the pH is adjusted to 7.0 with 0.1M sodium hydroxide solution,then it is filled up to 1000 μl with distilled water. The solution is prepared at 4° C.

The following solutions were added to 4 μl each of the solutions containing DNA fragments: 3 μl of L solution, 1 μl of DTT solution, 1 μl of ATP solution and 1 μl of distilled water. To join the linear DNA molecules the reaction mixture was supplemented with 1 μl of a solution containing 2.5 units of T4 DNA ligase (Amersham, England) and then it was incubated for 16 hours at 15° C.

After this treatment the YpGYOK2T DNA molecule containing the GAPDH terminator appeared in the reaction mixture.

6.A.i) Production of YEpGYOK2eb2 (see also FIG. 19)

20 μl of YpGYOK2T plasmid, 10 μl of E4 buffer and 69 μl of distilled water were mixed. 20 units of SalI restriction endonuclease (Amersham, England) were added to the reaction mixture and it was incubated for 16 hours at 37° C. After protein extraction (see above) the linear DNA molecules were precipitated and redissolved in 10 μl of TE (see Example 1B).

20 μl of YEpGYOL1eb1 plasmid DNA (Example 6Ad), 10 μl of E3 buffer and 68 μl of distilled water were mixed. To prepare E3 buffer 5000 μl of 2M Tris.Cl (pH 7.5), 3300 μl of 3M NaCl, 1000 μl of 1M magnesium chloride, 50 μl of mercaptoethanol and 650 μl of distilled water were admixed. 20 units of XhoI restriction enzyme (Amersham, England) were added to the reaction mixture containing the plasmid DNA and it was incubated for 16 hours at 37° C. The fragments of YEpGYOL1eb1 DNA, which were digested by the said restriction enzyme, were separated by electrophoresis and isolated. XhoI sticky ends can be found at the ends of the produced smaller fragment containing pX promoter, signal sequence and hirudin structural gene.

The above-produced linear DNA molecules of YpGYOK2T plasmid having SalI sticky ends and the fragment derived from YEpGYOL1eb1 plasmid DNA (containing the pX promoter, signal sequence, hirudin structural gene and having XhoI sticky ends) can be ligated. This can be achieved because the single-stranded part of the XhoI and SalI cleavage sites are complimentary. After ligation, however, the formed double-stranded DNA can be cleaved neither by SalI nor by XhoI enzymes.

3 μl each of the foregoing linear fragments were added to 3 μl of L solution, 1 μl of DTT solution, 1 μl of ATP solution (see above) and 3 μl of distilled water. To join the linear DNA molecules 1 μl of a solution containing 2.5 units of T4 DNA ligase (Amersham, England) was added to the reaction mixture and it was incubated for 16 hours at 15° C. The circular YEpGYOK2eb2 DNA molecule appeared in the mixture, which was then isolated by the method described above. FIG. 19 shows the scheme of production of the aforesaid plasmid and its partial restriction and functional map.

6.A.j) Production of YEpGYOK2(eb2)2 (see also FIG. 16)

The process of Example 6Afb was used with the difference that the foregoing YEpGYOK2eb2 plasmid was employed, instead of YEpGYOK1eb2.

6.A.k) Production of YEpGYOK2eb6 (see also FIG. 18)

The process of Example 6Ag was used with the difference that the YpGYOK2 plasmid DNA (see Example 6Aa) was utilized instead of YpGYOK1. In this way the YEpGYOK2eb6 plasmid DNA was obtained.

The hirudin HV-1 production by transformants containing expression and secretion cassettes are described in Example 8. The isolated (using the method given in Example 10) and identified (applying the method described in Example 11) product proved to be desulphatohirudin HV-1.

The following strains were deposited: *Saccharomyces cerevisiae* K25/2 (YEpGYOK1eb2) [accession number: NCAIM (P)Y 1172], *Saccharomyces cerevisiae* K25/4 (YEpGYOK2eb2) [NCAIM (P)Y 1174] and *Saccharomyces bayanus* K9 (YEpGYOK2eb2) [NCAIM (P)Y 1173].

6.B. Transformation of expression/secretion vector DNAs into Saccharomyces species The plasmid DNAs were introduced into *Saccharomyces cerevisiae* and *Saccharomyces bayanus* cells using the following process. The strains were maintained on YPDa medium containing the following ingredients: 1% of yeast extract (Difco), 2% of peptone (Difco), 2% of glucose and 2% of agar (Bacto). The medium was adjusted to pH 7.0 with 10% sodium hydroxide solution. 100 ml of sterilized YPD medium in a 500 ml total volume Erlenmeyer flask were inoculated by cell suspension derived from a slant culture. The composition of YPD medium was the same as that of YPDa, with the difference that the former contains no agar. The cultures were incubated for 16–18 hours at 28° C. by rotary shaker. The culture broth containing 1–1.5×$10^8$ of cells/ml was centrifuged (5000 rpm, 10 min.), the cells were then washed once with water. The pellet was suspended in a solution containing 1.2M of sorbitol, 25 mM of EDTA and 5 mM of dithiothreitol (pH 8.0) and it was gently agitated for 10 min at 28° C.

The pretreated cells were harvested by centrifugation (3000 rpm, 10 min.), and after washing twice with 1.2M sorbitol they were resuspended in a mixture containing the following ingredients; 0.5% of Novozym 234 (Calbiochem) enzyme dissolved in ECS solution of pH 5.8 (1M of sorbitol, 10 mM of EDTA and 100 mM of citric acid). The cells, which were forming spheroplasts, were carefully agitated and incubated at 28° C. while controlling the development of the process in every 10–15 min. by microscope. From 25 to 45 min. are necessary to the proper spheroplast formation, depending upon the strain applied. The spheroplasts were centrifuged and washed twice with 0.8M sorbitol solution, then the pellet was washed again in STC mixture containing 0.8M of sorbitol, 10 mM of Tris.Cl and 10 mM of calcium chloride.

To transform spheroplasts the desired DNA was mixed with equal volume of 2M sorbitol solution and added to 0.5 ml of STC mixture produced according to the method described above. The transformation mixture was carefully agitated and incubated at 28° C. for 10 min., subsequently 0.9 ml of PEG-TC solution of pH 7.4 (containing the following ingredients: 22% of polyethylene glycol 4000, 10 mM of calcium chloride and 10 mM of Tris. Cl) was added. After careful shaking for 25 min. at 28° C. the transformation mixture was centrifuged (12,000 rpm, 2 sec.) and the pellet was suspended in 0.3 ml of sorbitol-YPD medium (YPD medium was mixed with 2M of sorbitol in a ratio of 1:1). To regenerate the cell walls the cells were plated onto MMWS-YNB agar containing the following components: 0.67% of yeast nitrogen base (without amino acids), 2.0% of glucose, 18.22% of sorbitol, 2.0% of agar (Bacto) and it was supplemented with the required amino acids or nucleotide bases (50 μg/ml). 0.1 ml of transformation mixture was plated onto 20 ml of regeneration agar and it was overlayered with 7 ml of top agar having the same composition as MMWS-YNB, with the difference that it contained 3 agar, instead of 2%. The cultures were incubated at 28° C. till the appearance of colonies.

The following strains were transformed with the expression/secretion plasmid DNAs by the method described in Example 6A:

*Saccharomyces cerevisiae* GYOKI (M) 1 (NCAIM/P/Y 1156),

*Saccharomyces cerevisiae* GYOKI (M)5 (NCAIM/P/Y 1157),

*Saccharomyces bayanus* BO-74 (NCAIM/P/Y 1158).

First the hirudin production of transformants growing under selective fermentation circumstances described in Example 8 was monitored, then the hirudin concentration of cultures was determined by using the method described in Example 9, finally the hirudins were prepared as described in Example 10 and identified according to Example 11.

EXAMPLE 7

Expression of Hirudin in Streptomyces Cells

7.A. Production of expression/secretion vector DNAs

7.A.a) Production of pMI1.3 plasmid

Total DNA was isolated from *Streptomyces tenebrarius* [NCAIM (P)B 169] strain using the method of Example 2B, but the duration of lysozyme treatment was only 15 min., instead of 1.5 hours.

Figure 20:
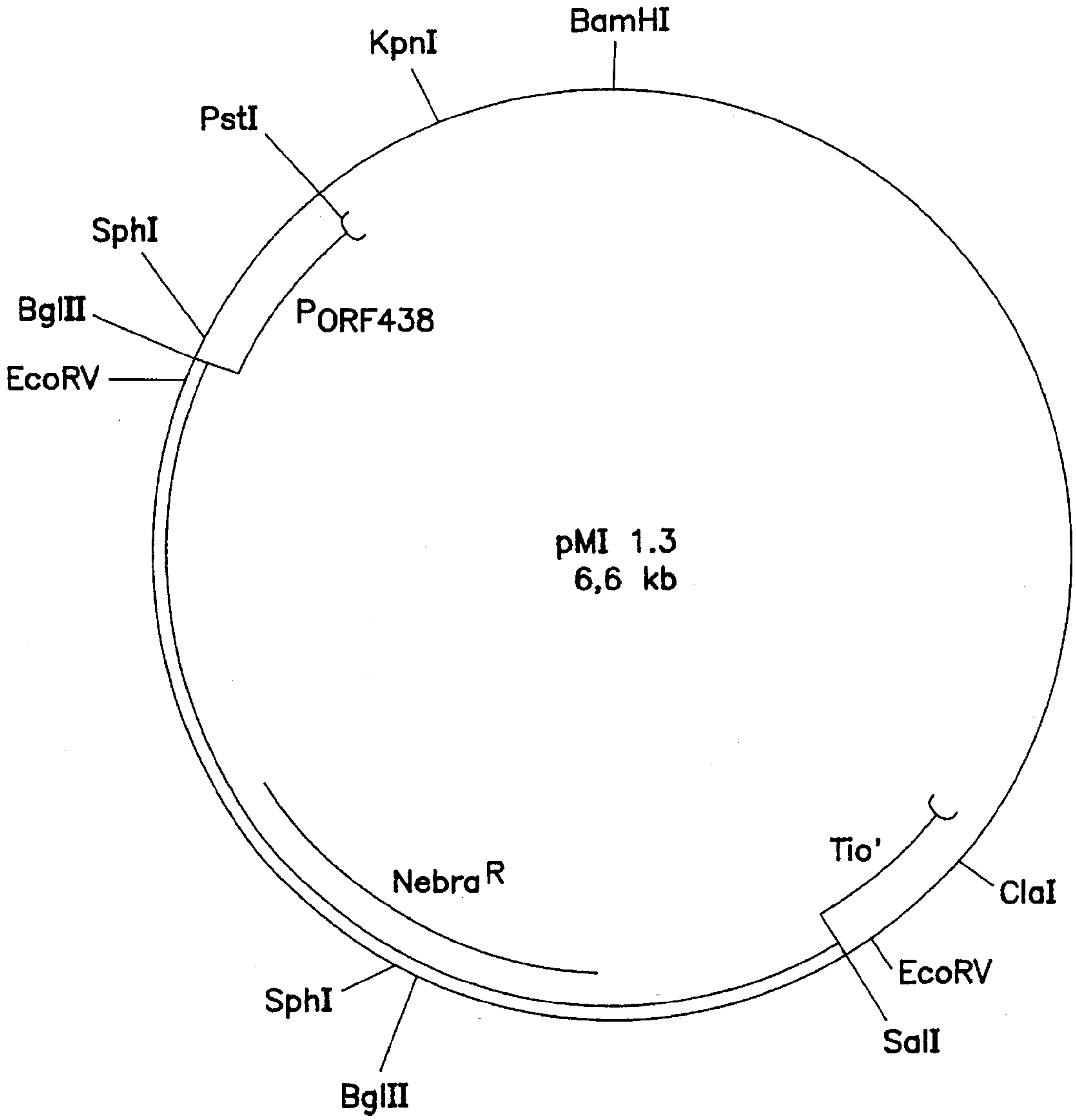
FIG. 20 shows the partial restriction map of pMI1.3 vector DNA.

The prepared total DNA was partially digested with MboI restriction endonuclease (BRL) applying the instructions of the manufacturer. DNA fragments ranging from 2 to 10 kb were isolated by agarose gel electrophoresis and electroelution, then the MboI fragments (suitable for inserting into BglII cleavage sites) were ligated into pIJ702 vector DNA [*Streptomyces lividans* pIJ702, NCAIM (P)B 1185] linearized with BglII endonuclease. *Streptomyces lividans* [NCAIM (P)B 257] cells were transformed according to Example 7C. by the pMI1 plasmid population received after ligation. The transformants were selected on a medium containing apramycin and tobramycin. One of the resistant *Streptomyces lividans* transformants was designated pMI1.3. FIG. 20 shows the partial restriction and functional map of this plasmid.

7.A.b) Production of pMIAMHIR3/A plasmid

The KpnI fragment of pUC19::H16 plasmid DNA produced in the way described earlier was ligated into pMI1.3 plasmid DNA cleaved by KpnI restriction enzyme. The ligation mixture was transformed into *Streptomyces lividans* [NCAIM (P)B 257] cells using the following method.

Figure 21:
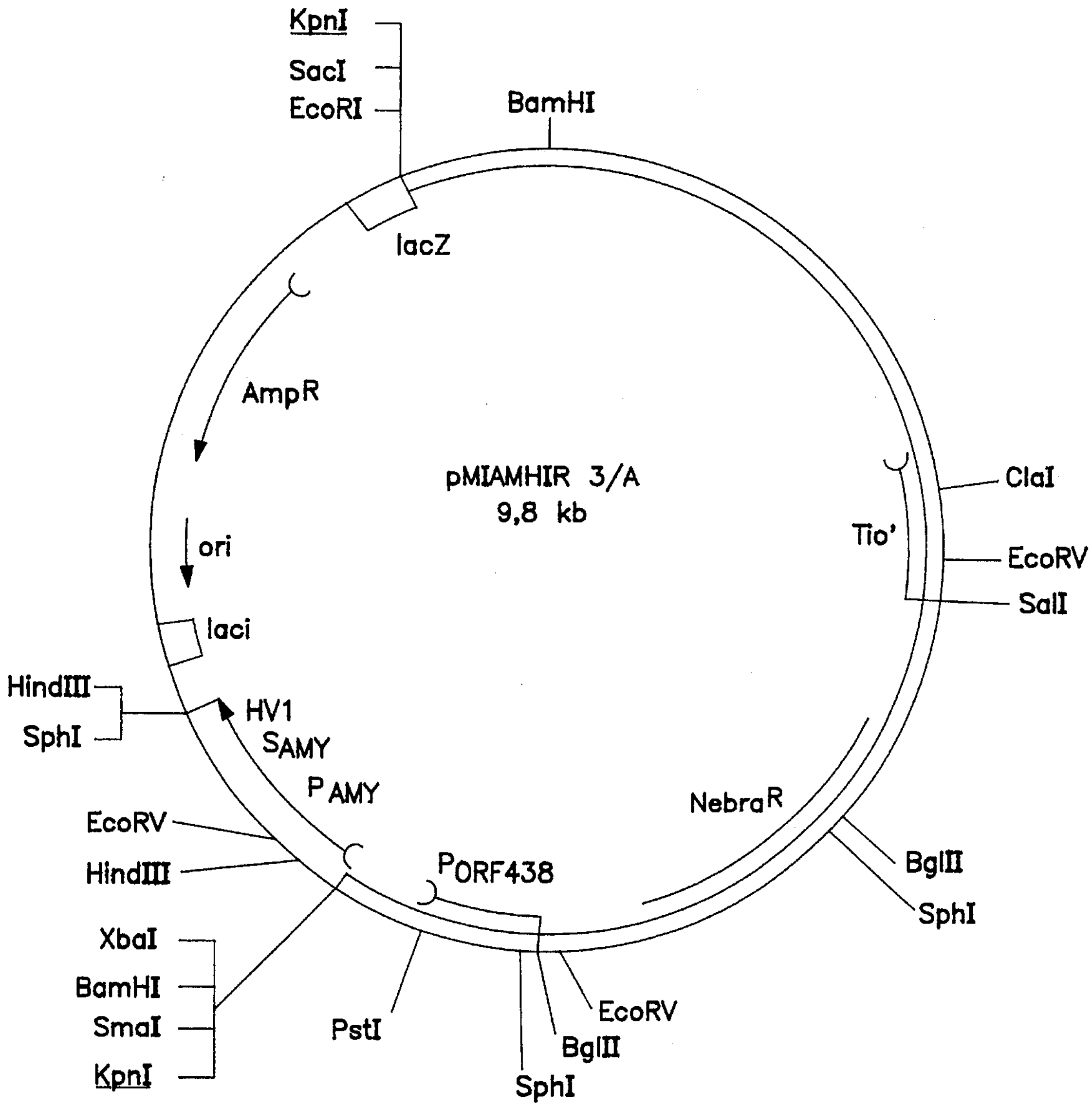
FIG. 21 shows the partial restriction map of pMIAMHIR3/A vector DNA.

The transformants were selected on R2YE medium (see below) containing 50 μg/ml of apramycin and/or tobramycin (BIOGAL) at 28 ° C. The hirudin production of transformants was screened by using the methods given in Examples 8 and 9, and one of the resistant and hirudin-producer strains was called *Streptomyces lividans* pMIAMHIR3/A. The plasmid was deposited under accession number NCAIM (P)B 1181. FIG. 21 shows its partial restriction and functional map.

7.A.c) Production of pMI-K2deltaNeo plasmid

Figure 22:
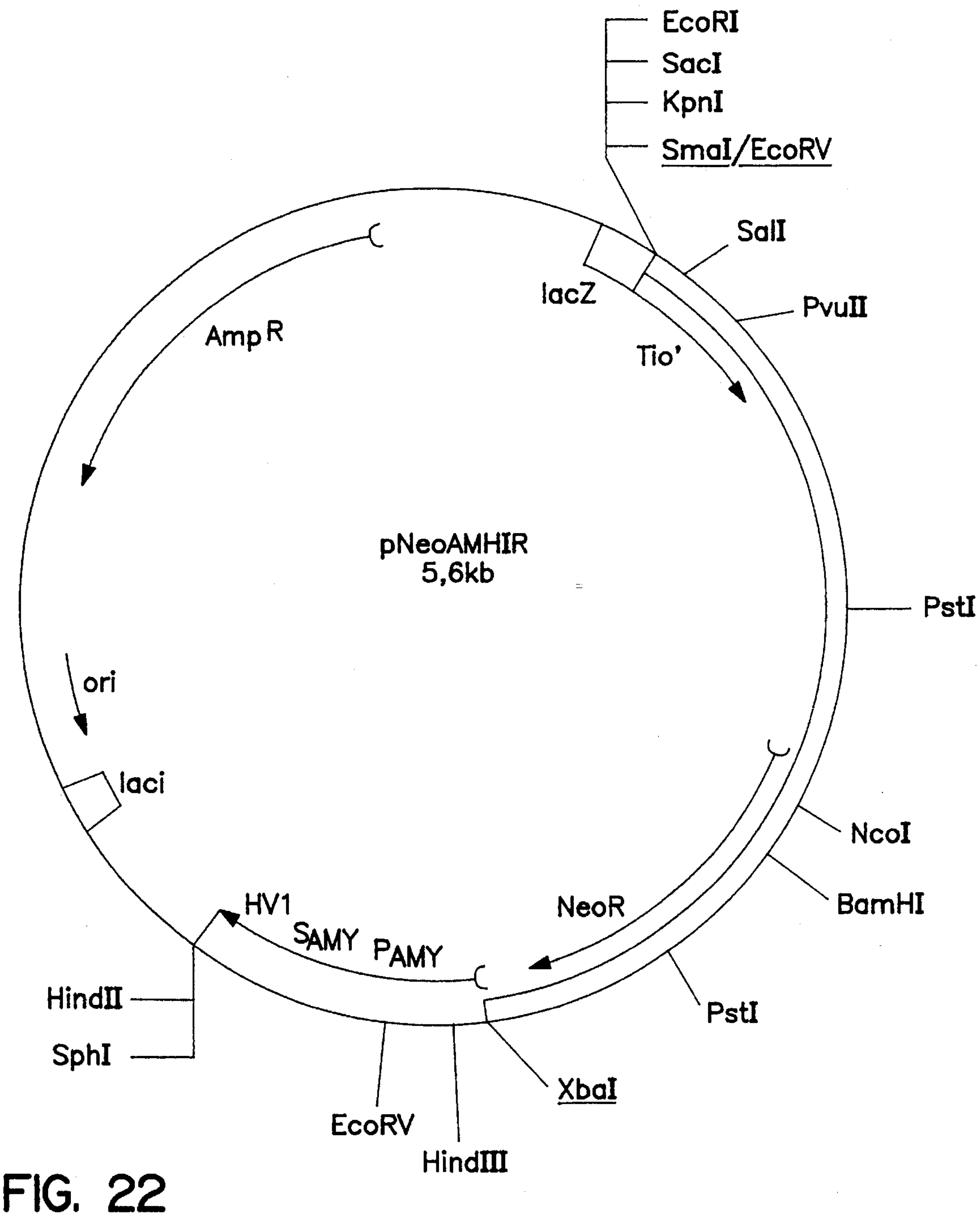
FIG. 22 shows the partial restriction map of pNeoAMHIR vector DNA.

To produce the pNeoAMHIR plasmid containing the neomycin phosphotransferase gene of pGYOKI½ plasmid [see Hungarian patent specification No. 197,045, accession number NCAIM (P)B 1009], the foregoing gene was isolated on an EcoRV-XbaI fragment and it was inserted into the SmaI-XbaI site of pUC19::H16 [NCAIM (P)B 1170] plasmid (having an expression cassette containing the promoter and signal sequence of *Bacillus circulans* α-amylase and the hirudin structural gene), the digestions and ligations were accomplished according to the instruction of the manufacturer. The transformation and the selection of transformed cells were accomplished as mentioned above. The produced plasmid was designated pNeOAMHIR. FIG. 22 shows its partial functional and restriction map. After isolating the pNeoAMHIR plasmid by the miniprep method (see above) the DNA was cleaved by NcoI restriction enzyme and the sticky ends were treated by Mung Bean nuclease (Amersham). After treatment with EcoRV the 4.6 kb long EcoRV-NeoI fragment was recircularized by ligation. The restriction digestions and the ligation were carried out according to the instructions of the manufacturer.

The ligation mixture was transformed into *Streptomyces lividans* cells, the transformation and the selection of transformants were accomplished using the method given above.

Figure 23:
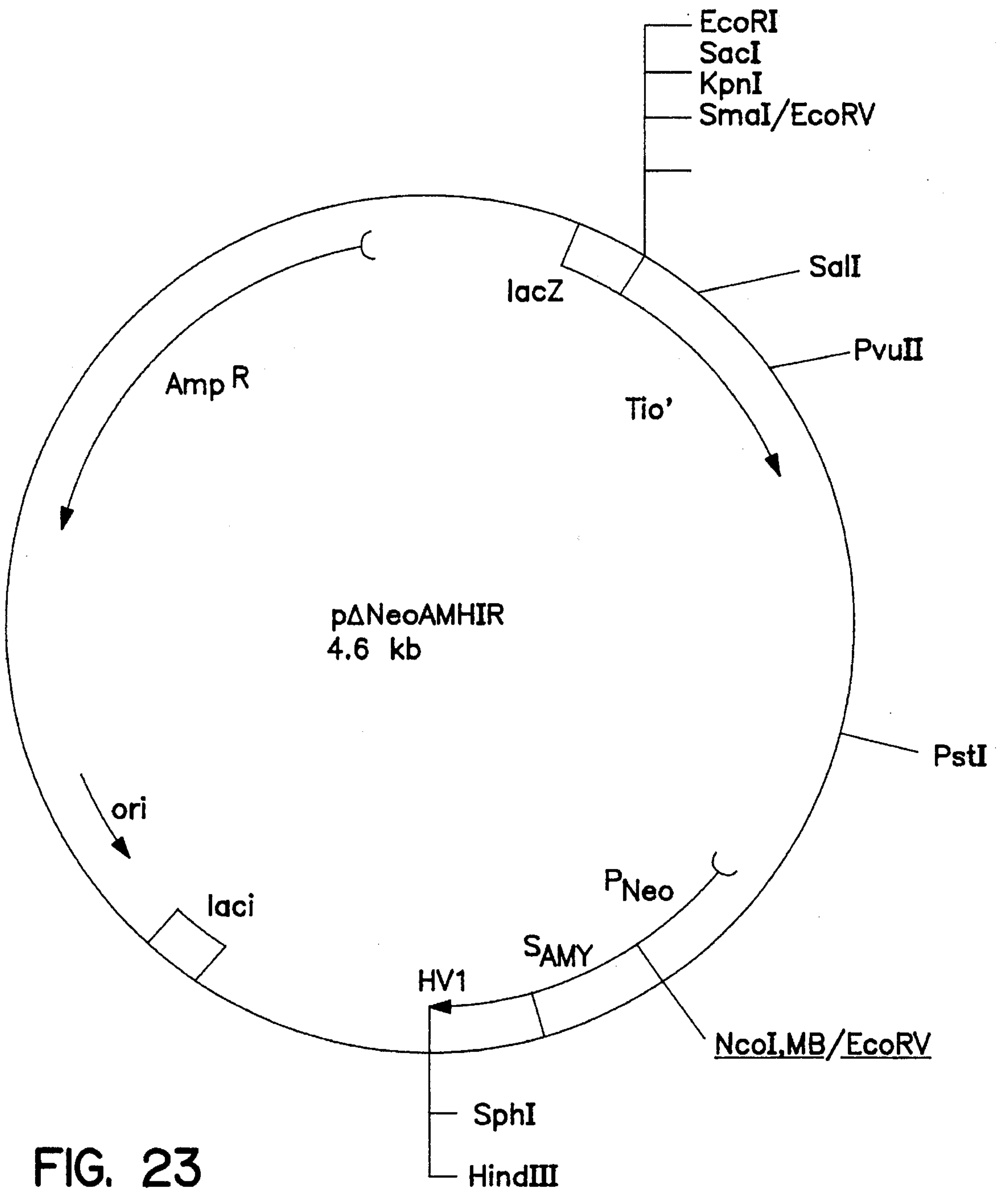
FIG. 23 shows the partial restriction map of pdelta-NeoAMHIR vector DNA.

The promoter derived from the Bacillus and the structural gene of neomycin phosphotransferase are lacking from the obtained pdeltaNeoAMHIR plasmid, whereas the promoter of neomycin phosphotransferase can be found upstream of the secretion signal of *Bacillus circulans* α-amylase. FIG. 23 shows the partial functional and restriction map of the said plasmid.

Figure 24:
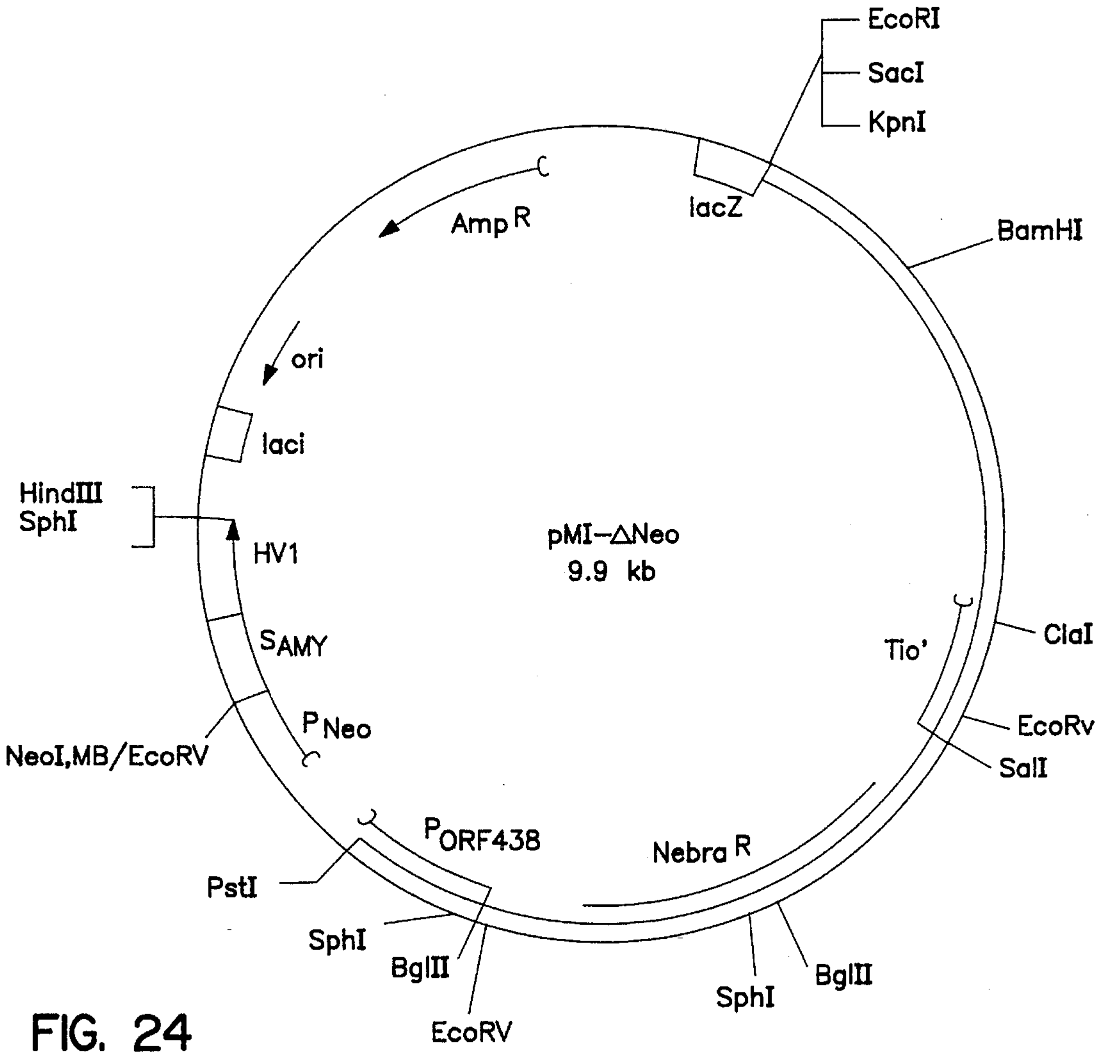
FIG. 24 shows the partial restriction map of pMI-delta-Neo vector DNA.

To produce pMI-deltaNeo (see FIG. 24) *E. coli*—Streptomyces bifunctional plasmid the 3.6 kb long PstI-KpnI fragment of pdeltaNeoAMHIR plasmid was ligated to the PstI-KpnI fragment of pMI1.3 plasmid. The restriction digestions and the ligation were made using the instructions of the manufacturer. The plasmid contains among others *E. coli* and Streptomyces replication origins, genes conferring resistance against nebramycin antibiotics, promoter derived from Streptomyces, signal sequence and hirudin structural gene. The strain containing the foregoing plasmid was deposited [*E. coli* MC1061 (pMI-deltaNeo)] under accession number NCAIM (P)B 1180.

The pMI-deltaNeo plasmid was transformed into *Streptomyces lividans* cells. The transformation and the selection of transformants were accomplished according to methods described above.

Figure 25:
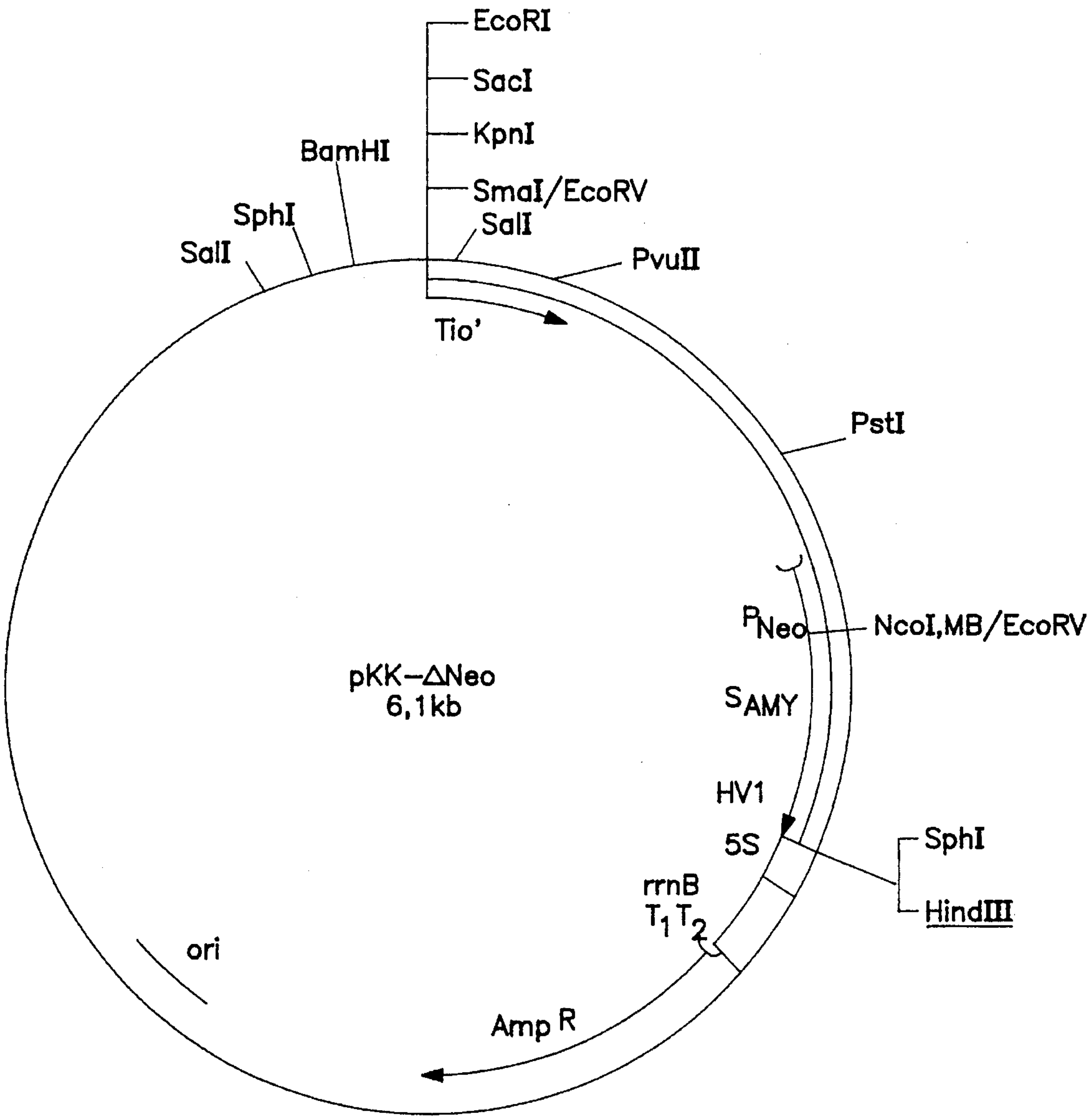
FIG. 25 shows the partial restriction map of pKK-delta-Neo vector DNA.

To the expression cassette of the foregoing plasmid, transcription terminator was joined corresponding to the reading direction thereof. The EcoRI-HindIII fragments containing expression cassette was cut out from the pdeltaNeoAMHIR plasmid, then it was inserted into the EcoRI and HindIII sites of pKK233-2 plasmid (Pharmacia). The restriction digestions and the ligation were achieved according to the instructions of the manufacturer (Amersham). In this way the Ptrc promoter of pKK233-2 vector was replaced by the expression cassette upstream to the transcription terminator. FIG. 25 shows the partial restriction and the functional map of the aforesaid pKK-deltaNeo plasmid.

Figure 26:
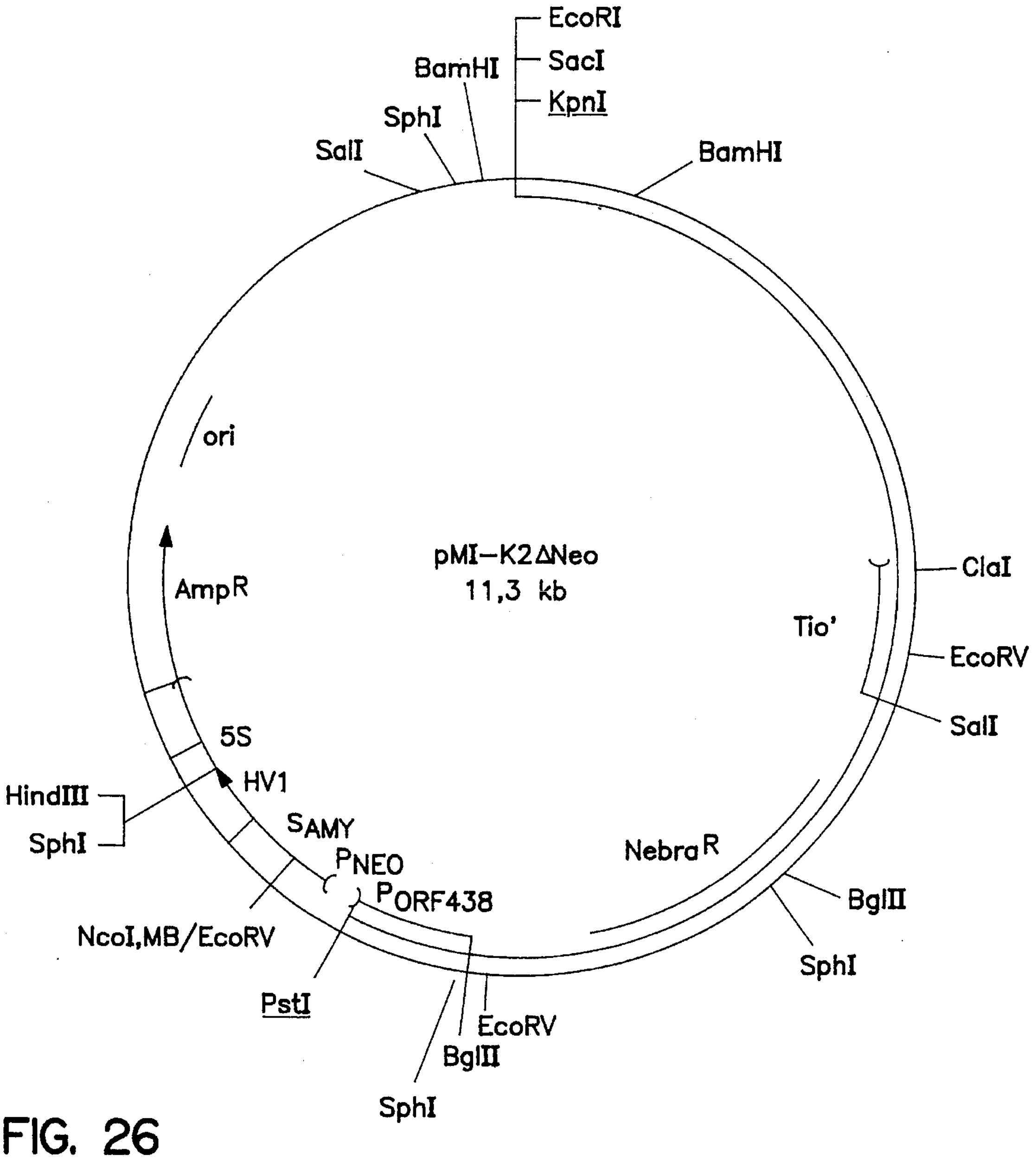
FIG. 26 shows the partial restriction map of pMI-K2deltaNeo vector DNA.

The 5.1 kb KpnI-PstI fragment of the pKK-deltaNeo plasmid was inserted into the KpnI and PstI sites of pMI1.3 Streptomyces vector to produce *E. coli*—Streptomyces bifunctional DNA vectors suitable for expressing and secreting hirudin. The restriction digestions and the ligation were carried out using the instruction of the manufacturer. FIG. 26 shows the partial restriction and functional map of the obtained pMI-K2deltaNeo plasmid. This plasmid contains replication origins for *E. coli* and for Streptomyces, marker genes to ensure the selective cultivation both of microorganisms and the expression/secretion cassettes of pKK-deltaNeo plasmid for hirudin production.

The expression/secretion cassette comprises Neo promoter derived from Streptomyces, secretion signal region of *Bacillus circulans* α-amylase gene, synthetic hirudin gene and the transcription terminator of *E. coli* rrnBT1T2.

The *E. coli* MC1061 (pMI-K2deltaNeo) strain containing the foregoing plasmid was deposited under accession number NCAIM P(B) 178.

7.A.d. Synthesis of a new gene designed on the basis of Streptomyces codon usage New signal sequence and structural gene were designed considering the codon usage of Streptomyces species. FIG. 1*b* is the nucleotide sequence of oligomers showing the joining points thereof. The oligomers were synthesized using the method described in Example 1A, with the difference that the recipient vectors were the M13mp18 and M13mp19 phages (New England Biolabs, Inc.). The signal sequence (denoted: ss) was cloned between HindIII and PstI while the structural gene (denoted: sg) was cloned between PstI and BamHI cleavage sites (see Example 4C). The desired clones were chosen after sequencing the received phages (Sequenase version 2.0 kit, United States Biochemical, USA) according to the instruction of the manufacturer. Double-stranded phage DNAs were isolated from M13mp18::ss and M13mp19::sg recombinant phages by the maxiprep method (Example 1B). Both samples were digested with PstI and BamHI enzymes (New England Biolabs., USA) according to the instructions of the manufacturer, furthermore the M13mp19::sg was digested with ClaI enzyme, too. The two reaction mixtures were admixed, precipitated, ligated and after transformation the transformed cells were plated as in Example 4C except that the X-gal and the IPTG were omitted. Using the method of Example 4C, after EcoRI and HindIII digestions the proper orientation and location of ss and sg oligonucleotides were determined by using gel electrophoresis. Double-stranded phage DNA was isolated from M13mp18::ss-sg phage by the method described in Example 1B. After digestion by PstI enzyme (New England Biolabs., USA) according to the instruction of the manufacturer it was treated by Mung Bean exonuclease (Pharmacia) according to the instruction of the manufacturer. Thereafter it was precipitated, ligated, transformed and plated according to Example 4C with the difference that X-gal and IPTG were not used during plating. The desired clones were selected after sequencing the obtained phages (Sequenase version 2.0 kit; United States Biochemical, USA) according to the instructions of the manufacturer. The foregoing clone was designated M13mp18::SH16. The SH16 cassette was subcloned into pUC19 plasmid using the methods of Example 1B. The strain was deposited under accession number NCAIM (P)B 1182.

7.A.e. Production of *E. coli*—Streptomyces bifunctional vector carrying "SH16"

7.A.ea) Double-stranded phage DNA was prepared from M13mp18:SH16 recombinant phage using the method of Example 1B, then it was digested with BamHI, ClaI and HindIII enzymes (New England Biolabs, USA) according to the instructions of the manufacturer. After production of Phagescript double-stranded DNA (Stratagene) using the same methods as described for the preparation of M13mp18 double-stranded DNA in Example 7Ac), the DNA was digested with BamHI and HindIII enzymes (New England Biolabs, USA) according to the instructions of the manufacturer. The strain containing Phagescript phage was bought from Stratagene (USA) and it was maintained and propagated by the same method as used in the case of M13mp18. The two DNA samples were mixed, precipitated, ligated, transformed, and the transformants were plated by using the method described in Example 4C. The desired construction was chosen after sequencing the DNA (Sequenase version 2.0 kit; United States Biochemical, USA; according to the instruction of the manufacturer) derived from the white plaques, and it was called Phagescript::SH16. The GY1095 (pGYOKI½) [NCAIM (P)B 1009] strain was maintained according to the process described in Example 1B, and after propagation the plasmid DNA was isolated therefrom by the maxiprep method, with the difference that during the propagation of cells the medium contained 30 μg/ml of chloramphenicol.

The pGYOK½ plasmid DNA was digested with BglII and XbaI enzymes (New England Biolabs, USA) according to the instructions of the manufacturer.

After cultivation the strain containing pUC18 plasmid (Pharmacia, LKB; this strain was similarly maintained and cultivated as the strain containing pUC19 plasmid) the DNA was digested with BamHI and XbaI enzymes (New England Biolabs, USA) according to the instructions of the manufacturer. The two DNA samples were mixed, precipitated, ligated, transformed and plated according to Example 1B. Twelve from the obtained white colonies were cultivated and plasmid DNAs were isolated therefrom by the miniprep method, and the derivative containing the 2.6 kb long BglII-XbaI fragment of pGYOKI½ plasmid in pUC18 plasmid was chosen by digesting the prepared DNA with EcoRI and HindIII and by applying gel electrophoresis. It was designated JM109 (pUC18BamHI/XbaI::pGYOKI½ BglII/

XbaI) and DNA was isolated therefrom by the maxiprep method (Example 1B). The DNA was digested with NcoI and XbaI enzymes (New England Biolabs, USA) according to the methods of the manufacturer. Double-stranded DNA was isolated from Phagescript::SH16 by the maxiprep method (Example 1B) and it was digested with BspHI and XbaI enzymes (New England Biolabs., USA) according to the instructions of the manufacturer. The two digested DNAs were mixed and ligated, and after transformation the cells were plated onto LB plates containing 50 μg/ml of ampicillin (see Example 1B). Twelve transformants were cultivated and plasmid DNAs were isolated therefrom by the miniprep method, to ascertain the presence of a 850 kb long PstI fragment. The digested DNA fragments were separated by gel electrophoresis. The *E. coli* strain containing this plasmid derivative was called JM (pUC18::NSH16).

During the construction of the aforesaid plasmid the NcoI digestion was made immediately before the ATG codon of neomycin sequence of pGYOKI½ plasmid, while the SH16 gene designed on the basis of Streptomyces codon usage was digested with BspHI endonuclease immediately before the ATG codon. Due to these digestions, after ligation the promoter of neomycin joins precisely to the SH16 replacing the neomycin gene. 7.A.eb) Plasmid DNA was isolated from JM109 (pUC18::NSH16) by the maxiprep method (see Example 1B) and it was digested with PstI and XbaI enzymes (New England Biolabs, USA) according to the instructions of the manufacturer. To the digestion of DNA the same method was used as in case of pGYOKI½ plasmid. The two digests were mixed and ligated, the ligate was transformed into JM109 competent cells (see Example 1B), and the transformed cells were plated on LBa medium containing 30 μg/ml of chloramphenicol.

The developed colonies were propagated using the method described in Example 1B, plasmid DNA was isolated therefrom, the DNA was digested with PstI and XbaI enzymes and the fragments were separated by using gel electrophoresis. After evaluation, one of the clones containing SH16 in pGYOKI½ plasmid was chosen and called MC1061 (pGYOKI::NSH16). The strain was deposited under accession number NCAIM (P)B 1179. Plasmid DNA was isolated from this strain by the maxiprep method.

7.A.ec) The GY1095 (pGYOKI-1) strain was maintained by using the method described in Example 1B, and after propagation plasmid DNA was prepared by the maxiprep method, with the difference that 30 μg/ml of chloramphenicol were used in the medium. The pGYOKI-1 plasmid DNA was digested by PstI and partially by XbaI enzymes (New England Biolabs., USA) according to the instructions of the manufacturer.

Double-stranded DNA was isolated from pUC18::NSH16 also by the maxiprep method (Example 1B) and the DNA was digested with PstI and XbaI enzymes (New England Biolabs, USA) according to the instructions of the manufacturer. After mixing the two samples they were ligated, transformed and plated onto LBa medium containing 30 μg/ml of chloramphenicol using the method given in Example 1B. Twelve transformants were cultivated and plasmid DNA was isolated therefrom by the miniprep method, to ascertain the presence of a 850 kb long PstI XbaI fragment. The DNA was digested with PstI and XbaI enzymes and the digested DNA fragments were separated by gel electrophoresis. The desired strain was designated JM109 (pGYOKI-1::XNSH16). Plasmid DNA was isolated from the aforesaid strain by the maxiprep method (see Example 1B).

7.A.ed) The GYOK1095 (pGYOKI-1) strain was maintained by using the method described in Example 1B. After cultivation plasmid DNA was digested with PstI enzyme (New England Biolabs, USA) according to the instructions of the manufacturer.

Double-stranded DNA was isolated from the pUC18::NSH16 and the DNA was digested with PstI enzyme (New England Biolabs., USA) using the instructions of the manufacturer. The two samples were admixed, ligated, transformed and the transformants then plated onto LBa medium containing 30 μg/ml of chloramphenicol, applying the method described in Example 1B. Twelve transformants were cultivated and plasmid DNA was isolated therefrom. After PstI digestion the desired construction containing the 850 kb long fragment was chosen by using gel electrophoresis. In this case the insert can orientate in two directions which can be separated from one another by HindIII digestion. Constructions obtained in this way were called JM109 (pGYOKI-1::PNSH16A) and JM109 (pGYOKI-1::PNSH-16B). Plasmid DNAs were isolated from these strains by the maxiprep method (see Example 1B).

7.B. Transformation of *Streptomyces lividans* cells

The spore suspension of *Streptomyces lividans* strains was streaked onto the slant of R2YE medium containing the following components:

sucrose 10.3% potassium sulphate 0.025% magnesium chloride hexahydrate 1.012% glucose 1.0% casein hydrolysate (acid) (Difco) 0.01% trace element solution 0.1%

TES buffer (pH 7.2 ) 0.573% sodium hydroxide 0.075% agar (Bacto) 2.2%

The composition of the trace element solution is as follows:

zinc chloride 40 mg cupric chloride dihydrate 10 mg disodium borate decahydrate 10 mg ammonium molybdate tetrahydrate 10 mg ferric chloride hexahydrate 200 mg manganese chloride tetrahydrate 10 mg distilled water 1000 mg The TES buffer contains 10 mM of Tris.Cl (pH 8.0), 1 mM of EDTA and 50 mM of NaCl.

The medium was sterilized at 121° C. for 20 min., then 1% v/v of a sterile 0.5% potassium dihydrogen phosphate solution, 8.0% v/v of a sterile 3.7% calcium chloride solution and 1.5% v/v of a sterile 20% proline solution were added (pH 7.2). After 4 days incubation at 28° C. the cultures were washed with distilled water to collect the spores. The spore suspension was inoculated into 100 ml of BIBB 10 medium. The medium was sterilized in a 500 ml Erlenmeyer flask. The composition of the BIBB 10 medium is as follows:

sucrose 10.0% yeast extract (Difco) 0.3% peptone 0.5% 0.5% malt extract (Bacto) 0.3% magnesium chloride hexahydrate 0.1% glucose 1.0%

The BIBB 10 medium was adjusted to pH 7.0 with 10% sodium hydroxide solution before sterilization. The culture medium was shaken on a rotary shaker at 260 rpm for 24 hours at 28° C., then 3 ml of same were inoculated into 100 ml of fresh BIBB 10 medium supplemented with 0.5% of glycine before inoculation. These cultures were cultivated for 18 hours under the above cultural environment, and after checking the cells were collected by centrifugation (3500 rpm, 10 min.). The mycelium derived from 100 ml of the culture broth was suspended in 4 ml of PH mixture (pH 7.0) containing the following components:

sucrose 11.3% potassium sulphate 0.025% magnesium chloride hexahydrate 0.2% trace element solution (see above) 0.2 v/v % potassium dihydrogen phosphate 0.005% calcium chloride dihydrate 0.37%

TES buffer (pH 7.2, see above) 10.0 v/v %

1 mg/ml of lysozyme was added to the above suspension and it was incubated at 28° C. while the protoplast formation was checked at every 15 min. 30 to 60 minutes are necessary to the complete protoplast formation. 5 ml of PH buffer were mixed to the protoplast suspension, then it was let to settle for 10 min. The unsettled part of the suspension was filtered through a column containing cotton-wool in a height of 2 cm. The filtered protoplasts were centrifuged (see above) and the pellet was washed twice and used for transformation.

Plasmid DNA (generally 10 μl DNA to $10^9$ protoplasts) was added to the loosened pellet of protoplasts and it was supplemented with 0.5 ml of 40% polyethylene glycol 6000 dissolved in PH buffer. After gently mixing for 1 min. the tube containing the above suspension was centrifuged for 10 min. at 3500 rpm. The protoplast mixture was poured onto the surface of R2YE agar plates (their composition is described above). After incubating the plates at 28° C. for 24 hours, top agar containing the necessary antibiotics was overlayered thereon. The composition of the top agar is the following:

"Lab Lemco" powder (meat extract) 0.06% yeast extract (Oxoid) 0.12% peptone (Difco) 0.3% agar (Bacto) 0.6%

It is denoted SNA (pH 7.2).

The cultures were incubated at 28° C. till the appearance of transformed colonies.

To produce Streptomyces strains with a capability to express the two variants of hirudin HV-1 under the transcriptional control of α-amylase or neomycin promoter and to secrete the hirudins into the culture broth using the nucleotide sequence of α-amylase gene or a synthetic nucleotide sequence encoding secretion signal peptide, the *E. coli*—Streptomyces bifunctional plasmids (Example 7A) were transformed into Streptomyces cells using the method described in Example 7B. In the case of *Streptomyces lividans* (NCAIM/P/B 257) strain, the transformation efficiency was 1000–5000 transformed colonies/1 μg of DNA using $1\times10^6$ cells and the aforesaid plasmids. Employing selective culture conditions, some transformants were screened to determine the concentration of the produced hirudin applying the method described in Example 9, then the product was isolated according to Example 10 and it was finally identified as described in Example 11. The results are fully detailed in Example 8.

The following strains were deposited under accession number: *E. coli* JM109 (pUC19::SH16) [NCAIM (P)B 1182], *E. coli* MC1061 (pGYOKI::NSH16) [NCAIM (P)B 1179], *Streptomyces lividans* pIJ702 [NCAIM (P)B 1185] and *Streptomyces lividans* (pGYOKI1::NSH16) [NCAIM (P) B 1186].

EXAMPLE 8

Production of Fermentation Broth Containing Hirudin in Shake Flasks and in Laboratory-Scale Fermentor 8.A. Production of *E. coli* cultures containing hirudin Cells containing the expression/secretion cassettes determining the biosynthesis of hirudins are maintained on solid TAg medium (with 2% of Bacto agar).

The media were supplemented with antibiotics (detailed below). The strains containing heat-sensitive cI gene product were cultivated at a temperature of 28° C. The culture broth of NCAIM (P)B 1165 and NCAIM (P)B 1170 was supplemented with 50 μg/ml of ampicillin, while in the case of NCAIM (P)B 1176 strain 30 μg/ml oxytetracycline were employed. 100 ml of a sterile medium prepared in a 500 ml Erlenmeyer flask were inoculated with the developed cultures. The sterilization of the media was carried out at 121° C. for 10 min. The inoculated flask was shaken on a rotary shaker at 260 cycles/minute. At every 24 hours samples were taken to determine the cell count and the hirudin activity of cultures, using the method described in Example 9.

TABLE 1

| | Results based on the average of minimum five experiments in shake flasks | | | |
|---|---|---|---|---|
| Strain | Fermentation time (hour) | Cell count/ /ml | pH | Hirudin HV-1 μg/ml |
| NCAIM (P)B 1165 | 24 | $6\times10^8$ | 7.5 | 43 |
| | 48 | $8\times10^8$ | 7.9 | 35 |
| NCAIM (P)B 1170 | 24 | $7\times10^8$ | 7.7 | 35 |
| | 48 | $7\times10^8$ | 7.9 | 39 |
| NCAIM (P)B 1176 | 24 | $5\times10^8$ | 7.6 | 38 |
| | 48 | $2\times10^9$ | 8.1 | 42 |

The hirudins were isolated from the cultures using the method described in Example 10 and the product was identified according to Example 11.

8.B. Production of fusion protein by means of *E. coli* cells

The *E. coli* pop2136 (pEX1::BH207 Aspfp) [NCAIM (P)B 1169], the *E. coli* pop2136 (pEX1::BH221 AsndeltaEcoRV-SmaI) [NCAIM (P)B 1177] and the control strains pop2136 and pop2136 pEX1 were maintained on TAg medium (see above). The cultivation was carried out at 28° C.

100 ml each of media prepared in 500 ml Erlenmeyer flasks were inoculated from slant agar cultures. The sterilization of the media was achieved at 121° C. for 20 min. After sterilization 60 μg/ml of filter-sterilized ampicillin solution was added thereto. The flasks were shaken on a rotary shaker at 260 rpm for 16 hours, then fresh media containing the same components were inoculated with the aforesaid culture in the ratio of 1:100. The cells were grown to an OD 550 of 0.5 to 0.6. Reaching this range the incubation temperature was adjusted to 42° C. and the cells were allowed to grow for additional 2 hours. After chilling to 2° C. the cells were separated by centrifugation and disintegrated by sonication. The β-galactosidase—hirudin protein was separated by centrifugation and the hirudin was cleaved from the fusion protein with formic acid at the methionine residue.

After sonication of the cells, which were separated from 5 l culture, the wet weight of the centrifuged product, containing mainly fusion protein, was 2.6 g and 1.7 g, derived from *E. coli* pop2136 (pEX1: :BH207 Aspfp) [NCAIM (P)B 1169] and *E. coli* pop2136 (pEX1:: BH22 1 AsndeltaEcoRV-SmaI ) [NCAIM (P) B 1177 ] strains, respectively.

Figure 27:
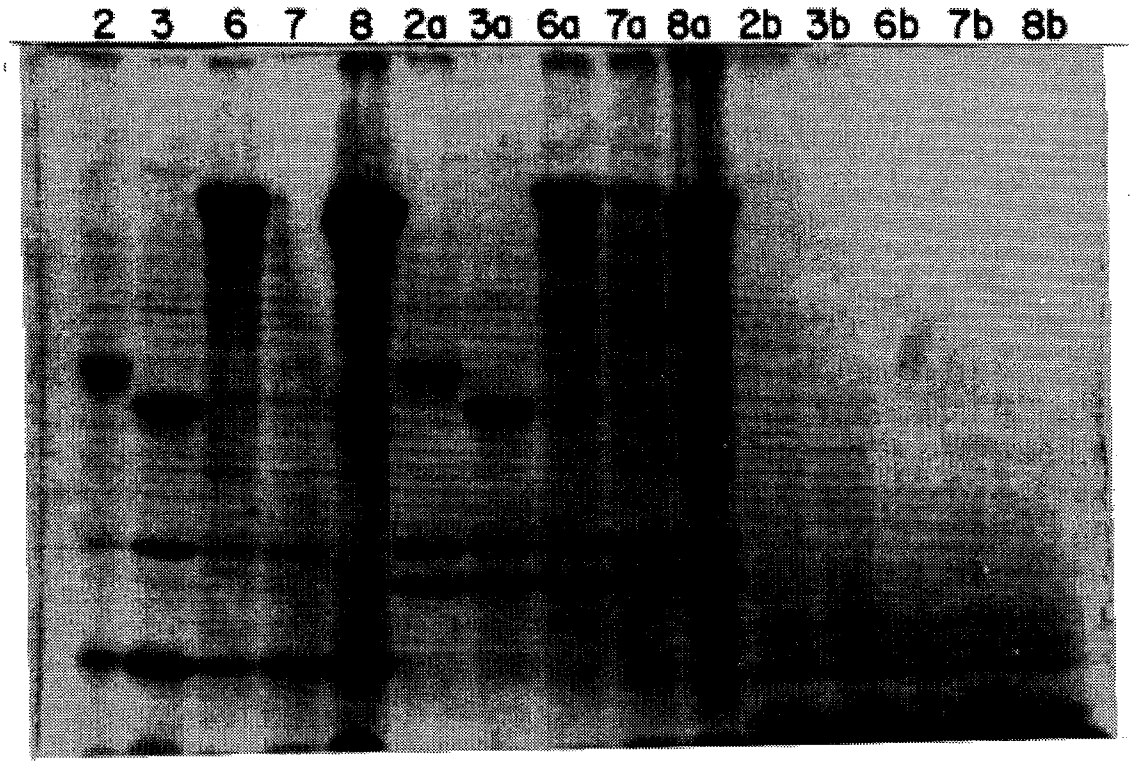
FIG. 27 is an SDS-PAGE gel showing the analysis of β-galactosidase-hirudin fusion protein.

FIG. 27 shows the picture of polyacrylamide (6%) gel electrophoresis representing the results of fermentation and isolation processes. The samples were loaded to gel in a mixture containing 60 mM of Tris.Cl (pH 6.8), 100 mM of dithiothreitol, 4% of SDS, 0.2% of bromophenol blue and 20% of glycerol, then they were electrophoresed for 6 hours (500 V, 400 mA). In FIG. 27 lane 8 represents the β-galactosidase (pEX1), lanes 6, 6a, 7a and 8 represent the β-galactosidase-hirudin complete fusion protein [*E. coli* pop2136 (pEX1::BH207 Aspfp) [NCAIM (P)B 1169], and lanes 2, 3, 2a and 3a correspond to the deleted derivatives [*E. coli* pop2136 (pEX1: :BH221AsndeltaEcoRV-SmaI) [NCAIM (P) B 1177]. Lane 8b shows the control pop2136 containing no plasmid.

8.C. Production of hirudin by means of Saccharomyces cells

The *Saccharomyces cerevisiae* and the *Saccharomyces bayanus* strains were inoculated onto MMWS-A medium containing the following ingredients:

ammonium sulphate 0.5% potassium dihydrogen phosphate 0.1% magnesium sulphate heptahydrate 0.05% glucose (separately sterilized) 2.0% sorbitol 3.0%

Wickerham vitamin solution* 0.1% agar (Bacto) 1.5%

*It was sterilized by filtration.

The composition of Wickerham solution is as follows:

folic acid 0.2 mg biotin 0.2 mg calcium pantothenate 40.0 mg inositol 200.0 mg nicotinic acid 40.0 mg p-aminobenzoic acid 20.0 mg pyridoxine hydrochloride 40.0 mg thiamine hydrochloride 40.0 mg riboflavin 20.0 mg distilled water 100.0 mg The pH of the MMWS-A medium was adjusted to 7.2 with 10% sodium hydroxide solution before sterilization.

The medium was sterilized at 121° C. for 25 min. The media of the *Saccharomyces cerevisiae* K25/2 [NCAIM (P)B 1172] land the *Saccharomyces bayanus* K9 [NCAIM (P)B 1173] strains were not supplemented, while the medium of *Saccharomyces cerevisiae* K25/4 [NCAIM (P)B 1174] was supplemented with 50 μg/ml of L-leucine.

The inoculum preculture fermentation broth was MMWS-Gal having the following composition:

ammonium sulphate 0.5% potassium dihydrogen phosphate 0.1% magnesium sulphate heptahydrate 0.05% galactose* 2.0%

Wickerham vitamin solution** 0.1%

*It was separately sterilized.

**It was sterilized by filtration (see above).

The pH of the medium was adjusted to 7.2 with 10% sodium hydroxide solution. The sterilization was carried out at a temperature of 121° C. for 30 min.

The inoculum preculture fermentation broth was supplemented with 50 μg/ml of uracil or leucine.

To cultivate the *Saccharomyces cerevisiae* [NCAIM (P)B 1172] strain, MMWS-Glu-Gal medium was employed. This medium has the same components as MMWS-Gal but it contains 3.0% of glucose beside 0.5% of galactose. Media with the same composition were used for production (main culture). 100 ml of MMWS-Gal (or MMWS-Glu-Gal, depending on the strain used, see above) medium prepared in 500 ml Erlenmeyer flask were inoculated with the total cell mass of an agar slant (MMWS-A) and it was cultivated on an orbital shaker at 260 rpm with 3.5 cm diameter orbit size at 28° C. temperature. After 20–22 hours the culture broth contains 6–9×$10^7$ cells suitable for inoculating.

100 ml each of sterile MMWS media prepared in 500 ml Erlenmeyer flask were inoculated with 1 ml each of the aforesaid culture. The media were incubated on the same shaker (see above) for 144 hours at 28° C. 1 g (1%) of galactose dissolved in sterile water was added to the culture of *Saccharomyces bayanus* (NCAIM/P/B 1173) in the 72th hour of cultivation.

The cell count and the pH of the culture, furthermore the amount of the produced hirudin were daily determined from fresh samples. Table 2 shows the results of fermentation carried out with *Saccharomyces cerevisiae* [NCAIM (P)B 1172] and *Saccharomyces bayanus* [NCAIM (P)B 1173] strains which gave almost the same values. The cell count of the living cells was determined by plating the cells onto solid MMWS-A and complete media (MMWS-A was supplemented with 0.5% of peptone and 0.5% of yeast extract), whereas the hirudin activity was measured by using the method described in Example 9.

TABLE 2

| Fermentation time (hour) | Living cell count/ml | pH | Hirudin HV-1 μg/ml |
|---|---|---|---|
| 0 | $2.1 \times 10^6$ | 7.2 | 0 |
| 24 | $9.1 \times 10^6$ | 7.1 | 9 |
| 48 | $6.2 \times 10^7$ | 6.3 | 56 |
| 72 | $1.1 \times 10^8$ | 5.1 | 86 |
| 96 | $3.3 \times 10^8$ | 4.3 | 95 |
| 120 | $4.6 \times 10^8$ | 3.1 | 110 |

Depending on the employed strain 5 liters of MMWS-Gal or MMWS-Glu-Gal medium were sterilized for 30 min. at 121° C. in a 10-liter vessel of a laboratory-scale fermentor equipped with a flat-blade-type impeller. The sterile medium was inoculated with 100 ml of the inoculum produced and checked as described above. When it was necessary, palm oil was added as antifoam agent. The cultivation was accomplished at a temperature of 28° C., at an aeration of 5 liters per minute. The agitation rate was set to 24 rpm. 45 g of sterile galactose dissolved in 100 ml of water were added to the culture of *Saccharomyces bayanus* [NCAIM (P)B 1173] strain in the 72th hour of fermentation.

During fermentation the following data were measured: cell count in minimal and complete media, the value of OD 600, the pH of the culture, and the activity of hirudin (occasionally the consumption of carbon source, the amount of dissolved oxygen and the carbon dioxide concentration of the outflow gas were determined, too).

Table 3 shows the results of characteristic fermentations carried out with *Saccharomyces cerevisiae* [NCAIM (P)B 1174] and *Saccharomyces bayanus* [NCAIM (P)B 1173] strains.

TABLE 3

| Strain and fermentation time (hour) | Cell count on minimal medium | Cell count on complete medium | OD at 600 nm | pH | Hir. HV-1 μg/ml |
|---|---|---|---|---|---|
| NCAIM (P)B 1173 | | | | | |
| 0 | $2 \times 10^6$ | $2 \times 10^6$ | 140 | 7.1 | 0 |
| 24 | $8 \times 10^6$ | $7 \times 19^6$ | 1040 | 6.5 | 8 |
| 48 | $4 \times 10^7$ | $5 \times 10^7$ | 1760 | 5.7 | 31 |
| 72 | $9 \times 10^7$ | $1 \times 10^8$ | 2890 | 4.3 | 57 |
| 96 | $3 \times 10^8$ | $3 \times 10^8$ | 3150 | 3.6 | 96 |
| 120 | $6 \times 10^8$ | $7 \times 10^8$ | 4240 | 2.8 | 132 |
| NCAIM (P)B 1174 | | | | | |
| 0 | $1 \times 10^6$ | $2 \times 10^6$ | 75 | 7.2 | 0 |
| 24 | $4 \times 10^6$ | $4 \times 10^6$ | 1140 | 6.7 | 5 |
| 48 | $1 \times 10^7$ | $2 \times 10^7$ | 1840 | 5.9 | 32 |
| 72 | $5 \times 10^7$ | $4 \times 10^7$ | 2900 | 4.6 | 66 |
| 96 | $1 \times 10^8$ | $3 \times 10^8$ | 3380 | 3.8 | 92 |
| 120 | $6 \times 10^8$ | $6 \times 10^8$ | 4240 | 2.9 | 125 |

If the strain maintenance and inoculation steps (see above) are achieved in a medium containing leucine and the second stage of fermentation is carried out in medium supplemented with 50 μg/ml of uracil, then hirudin activities exceeding the above values by 30–35% or in some cases by 60% will accumulate in the fermentation broth.

8.D. Production of fermentation broth containing hirudin by culturing *Streptomyces lividans*

The *Streptomyces lividans* strains, containing the following plasmids: pMIAMHIR3/A, pMIdeltaNeo, pMI-K2deltaNeo and pGYOKI1::NSH16, were cultivated on R2YE medium (see Example 7B) supplemented with 40 μg/ml of thiostrepton (Sigma) at 28° C. for 120 hours. The spore suspension deriving from the cultivated strain was inoculated into 100 ml of sterile (30 min. at 120° C) R2YE medium (without agar) prepared in a 500 ml Erlenmeyer flask, then it was grown on a rotary shaker at 260 rpm and 28° C. temperature for 120 hours. The hirudin contents of the cultures were determined from the samples taken at every 24 hours by using the methods of Example 9. The hirudin activities of the fermentation broths in the 120th hour were the following:

| | | |
|---|---|---|
| *Streptomyces lividans* | pMIAMHIR 3/4 | 14 μg/ml |
| | pMIdeltaNeo | 12 μg/ml |
| | pMI-K2deltaNeo | 18 μg/ml |
| | pGYOKI1::NSH16 | 27 μg/ml |

EXAMPLE 9

Determination of Hirudin Content

9.A. Rapid blood coagulation test 1 ml of 3.3% sodium citrate solution was mixed with 9 ml of human venous blood. 100 μl of the thus-preserved blood were mixed with 100 μl of bacterium culture, then 10 μl of 160 mM calcium chloride solution were added and the stop-watch was started at the same time. Under permanent agitation the time of appearing of the first detectable fibrin thread was measured. The culture is regarded as producer of hirudin-like substance only when it increases the blood-clotting time at least twice in relation to the control (a culture containing no expression/secretion plasmid DNA).

9.B. The Chromozym method

The necessary ingredients are the following: Chromozym TH (Boehringer Mannheim GmbH), Tris.Cl, NaCl, HCl, hirudin, triethanolamine and human thrombin (Sigma).

Principle of the method:

The thrombin, which is a protease, cleaves the Gly-Pro-Arg tripeptide from the synthetic substrate Chromozym (tosyl-glycil-prolyl-arginine-4-nitranilide acetate) resulting in yellow 4-nitraline, which changes the colour of the solution to yellow. The hirudin forms a stable complex with thrombin, blocking its activity, therefore it inhibits the aforesaid reaction. Solutions necessary to prepare the reaction mixture:

1. Buffer (pH 8.0, adjusted with HCl) contains 0.05M of Tris.Cl and 0.154M of NaCl.
2. 1.5 mM Chromozym solution This solution is prepared by mixing 500 μl of distilled water and 50 μl of triethanolamine. Dissolving of the substrate can be enhanced at 40–45° C. temperature. The substrate and its solution are kept at 4° C.
3. Hirudin solution containing 10 units/ml and its dilutions This solution is prepared by using buffer solution (1). It is stored at 0–4° C. The concentrated solution is preserved at −20° C.
4. Thrombin solution containing 2 units/ml and its dilutions This solution is prepared by using buffer (1). For a longer time it is stored at −20° C., for one week it is kept at 4° C.

The thrombin solution and the aliquots of hirudin dilutions are added into the wells of microplate for determining the standard curve. 100 μl of thrombin solution and 50 μl aliquots of hirudin dilutions, furthermore 50 μl of solutions with unknown activities are loaded into the wells of microplate and supplemented with 50 μl of Chromozym solution. The reaction starts at the moment of adding Chromozym at 37° C. The reaction is evaluated in visible light after 60 min. incubation. In the presence of appropriate amounts of hirudin the reaction mixture remains white, otherwise it becomes yellow.

After reading, the approximate hirudin concentration is calculated. Concentration of hirudin (μg/ml)=hirudin activity (unit): 12.

9.C. Method based on the inhibition of blood clotting

The principle of the method is based on the fact that the activity of hirudin can be quantitatively determined through its inhibitory action on thrombin standard having known clotting activity, therefore the hirudin activity of an unknown solution can be expressed in antithrombin units (AT-U). The clotting time of human plasma depends directly on the hirudin concentration.

Performance of measurement: to start the blood coagulation, 200 μl of citrated plasma are mixed with 100 μl aliquots of different hirudin contents and with 100 μl of standardized thrombin solution (corresponding to 1 NIH U) dissolved in 0.15M Tris.Cl (pH 7.4) buffer. The clotting time is measured in coagulometer (Schnitger-Gross). The concentrations of hirudin solutions are chosen in such a way that a 3–5-fold increase in the clotting time as compared to the hirudinless control be achieved.

Evaluation of the measurement:

Two calibration curves are taken to calculate the activity of hirudin samples. Trombin solutions containing 0.1 to 1.0 U thrombin/100 μl are used to obtain the calibration curve of thrombin and the corresponding clotting times are registered. The amount of thrombin (X) not blocked by hirudin and the corresponding 4-fold clotting time (the quotient of the measured and the control blood-clotting times) are read from the above curve.

The amount of hirudin (Y) corresponding to the 4-fold clotting time is read from the calibration curve of hirudin drawn by plotting hirudin concentrations against coagulation times. The hirudin amount belonging to 4-fold relative coagulation time (Y) is read from this curve. Based on the values read from the two calibration curves (considering that 1 U/100 µl of thrombin was permanently used in the reaction mixture) the specific hirudin activity in mg amounts can be calculated by the following equation:

$$\frac{1000 (1 - X)}{Y} = AT - U/mg$$

9.D. Analysis of fermentation broth by HPLC (semiquantitative method)

50 ml of fermentation broth are filtered and its pH is adjusted to 7.5 with NaOH. 50 ml of cooled acetone (15° C) are mixed to this solution. After one hour blending the fermentation broth is filtered. The filtrate is loaded onto a DEAE 32 (Servacel) anion exchanger column of 10 ml total volume, then the column is washed with 20 ml of 50% aqueous acetone. The column is eluted first with 5 ml, then with 30 ml of the buffer solution (20 mM of ammonium acetate, 1M of NaCl, pH 5.0). The eluted solution of a volume of about 30 ml is evaporated to a final volume of 5 ml in vacuo. This concentrated solution is analyzed by using reversed-phase HPLC system. The characteristics of the HPLC system are as follows:

column type: VYDAC C-18, 300 Å, 10 µm, 4 mm×250 mm (Bio Szeparációs Társaság, Budapest);

detection: at 220 nm and at 280 nm;

detection limit: −0.05–1.00 AUFS/10 mV final deflection;

injection: LKB Autosampler 2157;

solvents: solvent A: 0.1% of trifluoroacetic acid (TFA) in distilled water, solvent B: 0.1% TFA/acetonitrile;

elution: the following gradient profile is used for elution:

| Time (min.) | Flow rate (ml/min.) | Solvent A (%) | Solvent B (%) |
|---|---|---|---|
| 0–5 | 1.0 | 100 | 0 |
| 5–6 | 1.0 | 85 | 15 |
| 6–36 | 1.0 | 65 | 35 |
| 36–38 | 1.0 | 40 | 60 |

100 µl of concentrated sample was injected onto the column and the peak appearing at 21 min. 30 sec was compared to the peak of authentic desulphatohirudin HV-1.

EXAMPLE 10

Isolation of Recombinant Hirudin

10.A. Isolation of recombinant hirudin from the culture of E. coli cells 3 l of fermentation broth of E. coli JM109 (pUC19::H16) strain containing 45 µg/ml0f desulphatohirudin HV-1 were filtered through a Seitz filter, then the fermentation broth was adjusted to pH 7.5 with 1N NaOH solution. Subsequently, 3 l of 15° C. acetone were blended to the solution. The fermentation broth was mixed for 1 hour and filtered through a Seitz filter. The filtrate was loaded onto a DEAE 32 column (Servacel, 250 ml) at a flow rate of 350–500 ml/h, then the column was washed with 250 ml of 50% aqueous acetone and 250 ml of A-buffer (20 mM of ammonium acetate, 100mM of NaCl, pH 7.5). Thereafter the column was eluted with a linear salt gradient (stock solutions: 750 ml of A-buffer and 750 ml of B-buffer, the latter containing 20 mM of ammonium acetate and 4M of NaCl, pH 5.0) at a flow rate of 120–250 ml/h. The eluate was collected in 40 ml aliquots and the activity thereof was detected by the method of Example 9C. based on the inhibition of blood clotting. The active fractions (about 150 ml) were pooled and the pH of the thus-obtained solution was set to 7.5 with 1N NaOH solution, then it was concentrated to a final volume of 15 ml in circulation evaporator in vacuo on a water bath at 36°–38° C. The concentrated solution was loaded onto a Sephadex G-50 column (Pharmacia, 500 ml) (the ratio of the column diameter and the bed height was 1:25). The column was eluted with deionized water at a flow rate of 160 ml/h, and 50 ml fractions were taken. After the determination of blood-clotting activity of the fractions, the active fractions were collected (about 250 ml), concentrated in rotavap and finally lyophilized. Using this method 420 mg of crude product containing hirudin were obtained. The crude extract was dissolved in 3 ml of deionized water and the pH of the solution was adjusted to 7.5 with 0.2N NaOH solution. The obtained solution was loaded onto 14 ml of a Q-Sepharose fast flow anion-exchanger column (Pharmacia; ratio of column diameter and bed height was 1:15). The column was washed with 28 ml of deionized water, then it was eluted with 42 ml of 0.1M ammonium formiate solution (pH 3.9). During elution 1.5 ml fractions were taken and the hirudin activity of the fractions was checked by using the method based on blood coagulation. The active fractions were pooled (about 5 ml) and after adjusting the pH to 7.5 with 1N NaOH solution, the solution was concentrated in rotavap at 36°–38° C. The concentrated solution was brought to a Sephadex G-50 column (60 ml; Pharmacia; ratio of column diameter and bed height was 1:25). The column was eluted with distilled water and 5 ml fractions were taken. The blood-clotting activity of the fraction was determined, and the active fractions were collected (about 30 ml) and concentrated as above, finally they were lyophilized. In this way 210 mg of crude product were received. The crude extract was purified by RP-HPLC. For the purification an LKB apparatus was employed with the following characteristics:

column type: Delta Pak C-18 (300 Å), 19 mm×300 mm (Waters);

detection: at 220 and 280 nm;

detection limit: 0.01–2.0 AUFS/10 mV;

injector: Rheodyne 7125, sample loop 2000 µl;

fraction collection: manual.

Gradient elution was used during chromatography. The following solutions were used to prepare the eluents: solution A (0.1% of trifluoroacetic acid in tridistilled water) and solution B (0.1% of trifluoroacetic acid in acetonitrile).

30–60 mg of the crude product were dissolved in centrifuge tube in 1 ml of solution A. The solution was centrifuged at 4000 rpm for 5 min. The supernatant was injected using Hamilton syringe to a column equilibrated with solution A. The elution was carried out using the following gradient profile:

| Time (min.) | Flow rate (ml/min.) | Solvent A (%) | Solvent B (%) |
|---|---|---|---|
| 0–2 | 8.0 | 100 | 0 |
| 2–3 | 8.0 | 85 | 15 |
| 3–33 | 8.0 | 65 | 35 |
| 33–38 | 8.0 | 40 | 60 |

The desulphatohirudin HV-1 was eluted from the column between at 30 min. and at 30 min. 30 sec. in our preparative scale HPLC system. The fractions containing desulphatohirudin were pooled and lyophilized. In this way 42 mg of chromatographically uniform desulphatohirudin HV-1 (33 Asp) were obtained.

10.B. Production of desulphatohirudin HV-1 variants from fusion protein biosynthesized by means of E. coli 10 l culture broth of *E. coli* pop 2136 (pEX11::BM207 Aspfp) strain were cooled to 0° C. and the cells were separated by centrifugation at 3000 rpm for 15 min. at 4° C. The obtained wet pellet (14 g) was dissolved in a solution containing 60 mM of Tris.Cl (pH 8.0), 50 mM of NaCl and 1 mM of EDTA, then the bacterial cells were disintegrated by sonication (MSE; 5μ amplitude; 3 min.) in ice bath. 5 g of wet pellet containing β-galactosidase—hirudin fusion protein were obtained by centrifugation of the aforesaid suspension (15 min.; 10,000 g; 4° C.).

The fusion protein was dissolved in 180 ml of 70% formic acid under permanent stirring for 30 min., then the solution was mixed with 0.4 g of cyanogen bromide dissolved in 14 ml of 70% formic acid (1 mg dry protein/0.5 mg BrCN). The reaction mixture was kept out of light at room temperature, using nitrogen atmosphere for 15 hours, subsequently it was diluted ten-fold with deionized water. The aqueous solution was concentrated in vacuo and lyophilized. The obtained product (about 1 g) was redissolved in 10 ml of 6M guanidine hydrochloride and the solution was adjusted with β-mercaptoethanol to a final concentration of 0.1M. The pH of the solution was set to 8.2 with Tris-base and the solution was incubated for 3 hours at room temperature. Following that the solution was diluted 10-fold with a solution containing 6M guanidine hydrochloride, 50mM of Tris-base and 1 mM of EDTA, then it was dialyzed against 10-fold volume of 50 mM Tris-base for 18 hours. After centrifugation it was concentrated in vacuo and finally lyophilized. To obtain pure desulphatohirudin HV-1 (33 Asp) the lyophilizate was purified on preparative scale RP-HPLC using the method described in Example 10A.

10.C. Isolation of hirudin from the culture of *Saccharomyces cerevisiae*

Figure 28:
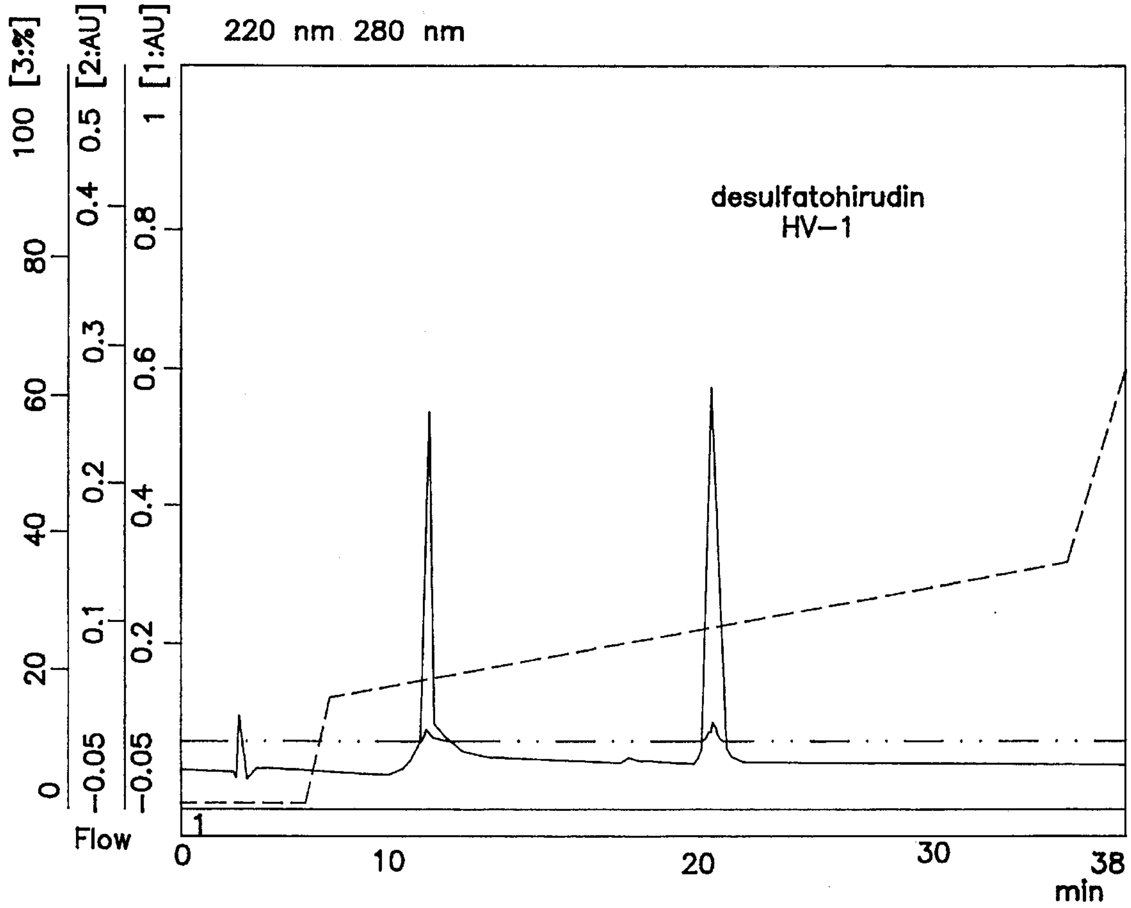
FIG. 28 shows the chromatographic profile of desulphatohirudin HV-1 made by HPLC. The desulphatohirudin HV-1 can be seen at 21 min. 30 sec.

5 l of fermentation broth, produced according to Example 8 by *Saccharomyces cerevisiae* K25/2 (YEpGYOK1eb2) strain containing 100 μg/ml of desulphatohirudin HV-1, were filtered through a Seitz filter, and the pH of the fermentation broth was adjusted to 7.5 with 1N NaOH solution. 5 l of 15 ° C. acetone were then admixed with the broth. After 1 hour of stirring the fermentation broth was filtered through a Seitz filter. The filtrate was loaded onto a DEAE32 (Servacel; 420 ml) anion-exchanger column at a flow rate of 600–800 ml/h (ratio of column diameter and bed height was 1:6), then it was washed with 450 ml of 50% aqueous acetone and 450 ml of A-buffer containing 20 mM of ammonium acetate and 100 mM of NaCl, pH 7.5). Subsequently, the elution was carried out by using linear salt gradient (stock solutions: 1260 ml of A-buffer and 1260 ml of B-buffer containing 20 mM of ammonium acetate, 4M of NaCl, pH 5.0) at a flow rate of 200–400 ml/h. The eluate was collected in 70 ml portions, the blood-clotting activity of which was determined by the method described in Example 9C. The active fractions were pooled (about 250 ml) and the pH of the obtained solution was adjusted to 7.5 with 1N NaOH solution. Finally it was concentrated to 25 ml in vacuo at 36°–38° C. The concentrated solution was loaded onto a Sephadex G-50 column (Pharmacia; 800 ml; the ratio of column diameter and bed height was 1:25). The column was eluted with deionized water at a flow rate of 260 ml/h. 80 ml fractions were collected. Fractions showing blood-clotting activity were pooled (about 400 ml) and after concentration the obtained solution was lyophilized. Applying this method 1.2 g of crude product containing desulphatohirudin were obtained. The crude extract was purified by using preparative scale RP-HPLC method described in Example 10A. Using this purification method 155 mg of pure desulphatohirudin HV-1 (33 Asp) were obtained. FIG. 28 shows the reversed-phase HPLC purification diagram of the product.

10.D. Isolation of recombinant hirudin from *Saccharomyces bayanus* cultures 5 l of fermentation broth produced by *Saccharomyces bayanus* K9 (YEpGYOK2eb2) strain were purified by using the method described in Example 10C. to produce chromatographically pure desulphatohirudin HV-1 (33 Asn).

10.E. Isolation of recombinant hirudin from the culture of *Streptomyces lividans*

5 l of fermentation broth produced by *Streptomyces lividans* (pGYOKI1::NSH16) were prepared by using the method of Example 10A resulting in chromatographically pure desulphatohirudin HV-1 ( 33 Asp) variant.

EXAMPLE 11

Confirmation of the Structure of Desulphatohirudin HV-1 (33 Asp) and HV-1 (33 Ash) Components The verification of the structure of hirudin components produced according to Examples 8 and 10 was carried out using the following methods.

11.A. Amino acid analysis

The amino acid composition was determined by using Waters PicoTag method. The hirudin was hydrolyzed with 6M of HCl solution in gas phase at 116° C. for 24 hours, the thus-formed amino acid residues were converted after neutralization to phenylthiocarbamoyl derivatives and the latter were separated by reversed-phase HPLC. The detection was carried out at 254 nm. The amino-acid composition of the product corresponds to the expected composition of hirudin HV-1. (The theoretical composition is the following: 3Lys, 1His, 6Cys, 9Asx, 4Thr, 4Ser, 13Glx, 3Pro, 9Gly, 4Val, 2Ile, 4Leu, 2Tyr, 1Phe). Asx denotes the total number of aspartic acid and asparagine, while Glx denotes the glutamic acid and glutamine.

11.B. Determination of N- and C-terminal amino acid sequence N-terminal analysis Determination of the chromatographically homogeneous desulphatohirudin HV-1 components was carried out in a Protein/Peptide Sequencer 471/A (Applied Biosystems). The N-terminal amino acid sequence of the investigated product was Val-Val-Tyr-Thr fitting to the expectations.

C-terminal analysis

Carboxypeptidase Y was employed to determine the C-terminal amino acid residues. The digestion was carried out in 10 mM phosphate buffer (pH 5.5) at a temperature of 37° C. The amino-acid composition was determined from the aliquots of digested samples which were taken at different times. The samples were injected into the amino acid analyzer in citrate buffer (pH 2.2). The result of the series measurement shows that the C-terminal amino-acid residue of our hirudin product is glutamine.

11. C. Total sequence analysis of desulphatohirudin HV-1 components

The hirudin, containing 65 amino-acid residues, comprises 3 disulphide bridges and the phenylthiohydantoin derivative of cysteine is instable, therefore it is necessary to convert the cysteine residues into stable derivatives. This was achieved in the following way: 1 nM of hirudin was dissolved in 50 μl of buffer (6M of guanidine hydrochloride, 0.25M of Tris.Cl, 2 mM of EDTA; pH 7.5), then 2 μl of freshly prepared 10% β-mercaptoethanol were added, then the mixture was incubated in argon atmosphere for 10 min. in dark and at room temperature. Thereafter 2 μl of a freshly prepared 1: 6 mixture of 4-vinylpyridine and ethanol were added to the mixture and it was incubated as above. The sample was adjusted to 2 ml with water and loaded onto a Seppak C-18 prepurification column (Millipore). The column was washed with 3 ml of water and it was finally eluted with 2 ml of 40% acetonitrile. The thus-formed pyridylethylated hirudin was purified on reversed-phase HPLC [Vydac C-18 10 μ; 4.6 mm×250 mm; at a flow rate of 1 ml/min.;

solution A (0.1% trifluoroacetic acid/TFA/in water); solution B (0.1% TFA in acetonitrile); from 0% B to 60% B during 30 min.]. The pyridylethylated derivative was eluted with almost the same retention time as hirudin.

The hirudin is too long to sequence it in one step to the C-terminal, therefore it seemed to be practical to make fragments thereof. The molecule contains 3 lysine residues at positions 27, 36 and 47. Therefore, after trypsin digestion 4 fragments can be theoretically obtained. However, the lysine at position 47 is followed by proline, therefore probably 3 fragments can appear.

The digestion by trypsin was carried out under the following circumstances. The alkylated hirudin was dissolved in 50 μl of 0.1M ammonium bicarbonate solution (pH 8.5). The trypsin was added to the solution in a ratio of 1:20 and the solution was then incubated for 3 hours at room temperature. The produced fragments were separated by RP-HPLC. The obtained four fragments proved to be the fragments of hirudin 1-27, 28-36, 37-65 and 28-65 using Applied Biosystems 471/A automatic sequencer. The appearance of the last fragment can be explained by the fact that the Lys-Asn bond at position 36–37 is not perfectly cleaved. As it was supposed, the 28-36 and 28-65 fragments of desulphatohirudin HV-1 (33 Asp) component contained aspartic acid at position 33 and in the case of desulphatohirudin HV-1 (33 Asn) asparagine was at this position.

11.D. Production of desulphatohirudin HV-1 (33 Asp) component from leech and its comparison with desulphatohirudin HV-1 33 Asp) component produced microbiologically 11.D.a. Isolation of hirudin HV-1 (33 Asp) component 130 g of leeches (*Hirudo medicinalis*) starved for one week were frozen to stone hard. The following day it was thawed at room temperature and chopped in 260 ml of 0.5M NaCl with a bladed propeller mixer, then it was homogenized in an Ultra-turrax apparatus. After stirring for 60 min. the pH of the mixture was adjusted to 2 with 20% hydrochloric acid. The acidic extract was warmed to 70° C. under permanent stirring for 15 min. After cooling to 0°–4° C it was centrifuged. The supernatant was precipitated with one and a half volume of absolute ethanol and the precipitate was collected by centrifugation. The obtained supernatant was adjusted to pH 2 with 20% hydrochloric acid. After diluting with a twofold volume of water, 20 g of fuller's earth were added. The suspension was filtered after 90 min. stirring. The hirudin was dissolved from the fuller's earth with 50% aqueous ethanol having a pH of 8.5 set with ammonia. After neutralization the eluate was concentrated in vacuo, then it was desalted by dialysis. The dialyzate was purified by gradient elution on an Ecteola cellulose column (bed height 23 cm; diameter 1.8 cm) equilibrated with 0.2M of ammonium-acetate buffer (pH 5.0; A-solution). 0.5M of NaCl dissolved in solution A was employed as solvent B to form the gradient. After elution the concentrated and lyophilized crude product showed a biological activity typical of hirudin.

An aliquot of the crude extract was loaded onto an RP-HPLC column (LKB Ultrapac TSK ODS-120T, 5 μm, 4.6×25 mm) equilibrated with 0.1% aqueous TFA solution (A-solution). Subsequently, the hirudin was eluted by linear gradient with solution B (0.1% of TFA in acetonitrile). The fractions which proved to be active were pooled and further purified on a Mono Q (Pharmacia) anion-exchanger column using gradient elutions. (Characteristics of the column: 5.0×50 mm; A-buffer: 20 mM of Tris.Cl (pH 7.5); B-buffer: 20 mM of Tris.Cl (pH 7.5) containing 1M of NaCl; gradient from 0% B to 70% B). To purify and desalt the fractions containing the active agent they were again loaded onto an LKB Ultrapac column, where the elution of hirudin was carried out in isochratic way at 23% of B-solution. In this way the hirudin HV-1 (33 Asp) component was produced in high purity.

11 .D.b. Hydrolysis of hirudin HV-1 (33 Asp) with trifluoroacetic acid 0.5 μg of isolated hirudin (see Example 11Da) was dissolved in 70 μl of distilled water. After adding 30 μl of TFA it was incubated for 25 min. at 57° C. The reaction mixture was diluted with 100 μl of distilled water and loaded onto an RP-HPLC column (LKB Ultrapac TSK ODS-120T) and eluted with a linear gradient from 0 to 60% of B-solution for 30 min. in the way as described in Example 11Da. Two peaks were monitored with the same height. One of the peaks was characteristic of hirudin isolated from leech and the other peak was eluted later. The retention time of the later peak corresponded to the retention time of recombinant desulphatohirudin HV-1 (Asp) produced microbiologically.

EXAMPLE 12

Preparation of a Pharmaceutical Product Containing Hirudin

Pharmaceutical products of high value were prepared from hirudin peptides produced by the process according to the invention. Pharmaceutically acceptable carriers were added to the product. The hirudin can be either dissolved or suspended in the appropriate carrier.

To produce intravenous or parenteral preparations, in 100 ml of pyrogen-free water 30 mg of hirudin HV-1 peptide and 0.9 g of analytically pure NaCl were dissolved. The solution was sterilized by filtration through a Millipore membrane and it was filled into an ampoule.

The thus-obtained pharmaceutical composition can be advantageously used in thromboembolical diseases for the blocking of arterial thrombosis and prevention of venous thrombosis.

What we claim is:

1. A process for producing desulphatohirudin HV-1 33 ASP and desulphatohirudin HV-1 33 ASN peptides, comprising the steps of biosynthesizing said desulphatohirudin HV-1 peptides by expressing the nucleotide sequences coding for said hirudin HV-1 peptides synthesized in vitro on the basis of the codon usage of microorganisms, under the control of pX promoter, UAS transcription activating sequence, initiation and termination codons, employing the synthetic nucleotide sequence [SEQ ID NO:30]:

. . . 5'-TCA TTC GTT CAA GGT GTA TCT TTG GAT AAG AGA-3' this sequence coding for signal peptide and an amino acid sequence to ensure the secretion and cleavage site for endopeptidase, using the URA3 and leu2-d genes to determine the level of expression and stability of plasmid vector DNAs, applying expression/secretion cassettes in the aforesaid plasmids, by means of cells of a yeast selected from the group consisting of *Saccharomyces bayanus* and *Saccharomyces cerevisiae,* by cultivating the foregoing microorganisms under proper fermentation conditions after transformation of plasmids comprising the aforesaid elements, then separating the hirudin accumulated extracellularly.

2. A process as defined in claim 1, in which the nucleotide sequence coding for the desulphatohirudin HV-1 variants, used in Saccharomyces cells, have the following formula (SEQ ID NO:21):

| | | | | | | | | | | | | | | |
|---|---|---|---|---|---|---|---|---|---|---|---|---|---|---|
| GTT | GTT | TAC | ACC | GAC | TGT | ACC | GAA | TCT | GGT | CAA | AAC | TTG | TGT | TTA |
| TGT | GAA | GGT | TCT | AAC | GTC | TGC | GGT | CAG | GGT | AAC | AAG | TGT | ATC | TTG |
| GGT | TCT | RAC | GGT | GAA | AAA | AAT | CAA | TGT | GTC | ACT | GGC | GAA | GGT | ACT |
| CCA | AAG | CCA | CAA | TCC | CAC | AAC | GAT | GGT | GAC | TTC | GAG | GAA | ATT | CCT |
| GAA | GAA | TAC | CTA | CAA. | | | | | | | | | | |

3. A process as defined in claim 1, in which the nucleotide sequence coding for the desulphatohirudin HV-1 variants having the formula (SEQ ID NO: 22):

GTG GTT TAT ACT GAC TGT ACC GAA AGC GGT CAG AAC CTC TGC CTG TGC GAG GGC TCG AAC GTC TGC GGA CAG GGG AAT AAG TGC ATC CTT GGA TCG GAG GGA GAG AAG AAT CAG TGC GTA ACC GGC GAG GGG ACA CCA AAG CCC CAA TCC CAC AAC GAC GGC GAT TTC GAG GAG ATA CCC GAG GAA TAC CTG CAA are produced and the used nucleotide sequence encoding secretion signal sequence has the following formula (SEQ ID NO: 23):

ATG ATC CTC AAG ACC TTC CCG AAG TTC CTG GCT GCG GTC CTT GCT CTC TCA CTG ACG GCG GCA CTC CCC CCA CTG TTC CCG GCC.

4. A process as defined in claim 2, in which the Saccharomyces vector DNA comprises a pX promoter, signal sequence, leader sequence, hirudin structural gene and termination region of FLP gene.

5. A process as claimed in claim 4 wherein the strains are *Saccharomyces cerevisiae* GYOKI (M)1 (NCAIM (P)Y 1156) and (M)5 (NCAIM (P)Y 1157) or *Saccaromyces bayanus* BO-74 (NCAIM (P)Y 1158).

6. A process as defined in claim 1, in which the Saccharomyces strains expressing desulphatohirudin HV-1 variants are maintained and precultivated in media containing leucine, and are cultivated in a fermentation broth which is supplemented with uracil.

7. A process as recited in claim 2, in which the Saccharomyces vector DNA comprises a pX promoter, signal sequence, leader sequence, hirudin structural gene and termination region of GAPDH gene.

8. A plasmid comprising the nucleotide sequence of an expression/secretion cassette comprising a pX promoter, signal sequence, leader sequence, hirudin structural gene and termination region of FLP gene.

9. A plasmid comprising the nucleotide sequence of an expression/secretion cassette comprising a pX promoter, signal sequence, leader sequence, hirudin structural gene and termination region of a GAPDH gene.

10. Saccharomyces cells transformed with the plasmid of claim 8.

11. Saccharomyces cells transformed with the plasmid of claim 9.

* * * * *

UNITED STATES PATENT AND TRADEMARK OFFICE

CERTIFICATE OF CORRECTION

PATENT NO.: 5,552,299

DATED: September 3, 1996

INVENTOR(S): OTT et al.

It is certified that error appears in the above-identified patent and that said Letters Patent is hereby corrected as shown below:

On the cover page, item [75], the twelfth listed inventor's first name "Kárnly" should read --Károly--.

Signed and Sealed this

Nineteenth Day of November, 1996

Attest:

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES: 31

( 2 ) INFORMATION FOR SEQ ID NO: 1:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear -continued ( x i ) SEQUENCE DESCRIPTION: SEQ ID NO: 1:

ATGAATATAT TTTACATATT TTTGTTTTTG CTGTCATTCG TTCAAGGTAC 50

CCGGGGA 57

( 2 ) INFORMATION FOR SEQ ID NO: 2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO: 2:

GATCCGGGCC CTGTTAGAGC T 21

( 2 ) INFORMATION FOR SEQ ID NO: 3:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( x i ) SEQUENCE DESCRIPTION: SEQ ID NO: 3:

GCCCGGGACA ATC 13

( 2 ) INFORMATION FOR SEQ ID NO: 4:

( i ) SEQUENCE CHARACTERISTICS:
( A ) LENGTH: 93 base pairs
( B ) TYPE: nucleic acid
( C ) STRANDEDNESS: single
( D ) TOPOLOGY: linear ( x i ) SEQUENCE DESCRIPTION: SEQ ID NO: 4:

```
ATG AAT ATA TTT TAC ATA TTT TTG TTT TTG CTG TCA TTC GTT CAA      45
Met Asn Ile Phe Thr Ile Phe Leu Phe Leu Leu Ser Phe Val Gln
 1               5                  10                  15

GGT ACC CGG GGA TCC GGG CCC TGT TAGAGCTCGG TACCTGGCCA TGGT       93
Gly Thr Arg Gly Ser Gly Pro Cys
                20
```

( 2 ) INFORMATION FOR SEQ ID NO: 5:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 5:

TAGTAAGCAT GCAAGCTT 18

( 2 ) INFORMATION FOR SEQ ID NO: 6:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO: 6:

GTCGGTGTAA ACAACTCTCT TATCCAAAGA TACACCTTGA ACGAATGA 48

( 2 ) INFORMATION FOR SEQ ID NO: 7:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO: 7:

```
CCGCTCGAGG GC                                                            12
```

( 2 ) INFORMATION FOR SEQ ID NO: 8:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO: 8:

```
CTGGCCATGG TTGTTTACAC CGACTCTACC GAATCTGGT                               39
```

( 2 ) INFORMATION FOR SEQ ID NO: 9:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( x i ) SEQUENCE DESCRIPTION: SEQ ID NO: 9:

```
ACC AGA TTC GGT ACA GTC GGT GTA AAC AAC CAT GGCCAGGTAC               43
Gly Ser Glu Thr Cys Asp Thr Tyr Val Val Met
 1              5                   10
```

( 2 ) INFORMATION FOR SEQ ID NO: 10:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 10:

```
CAA AAC TTG TGT TTA TGT GAA GGT TCT AAC GTC TGC GGT CAG GGT          45
Gln Asn Leu Cys Leu Cys Glu Gly Ser Asn Val Cys Gly Gln Gly
 1              5                   10                  15
```

( 2 ) INFORMATION FOR SEQ ID NO: 11:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 11:

```
ACC CTG ACC GCA GAC GTT AGA ACC TTC ACA TAA ACA CAA GTT TTG          45
Gly Gln Gly Cys Val Asn Ser Gly Glu Cys Leu Cys Leu Asn Gln
 1              5                   10                  15
```

( 2 ) INFORMATION FOR SEQ ID NO: 12:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 12:

```
AAC AAG TGT ATC TTG GGT TCT RAC GGT GAA AAA AAT CAA TGT GTC          45
```

-continued

Asn Lys Cys Ile Leu Gly Ser Asx Gly Glu Lys Asn Gln Cys Val
1 5 10 15

( 2 ) INFORMATION FOR SEQ ID NO: 13:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 13:

GAC ACA TTG ATT TTT TTC ACC CTG AGA ACC CAA GAT ACA CTT GTT 45
Val Cys Gln Asn Lys Glu Gly Asx Ser Gly Leu Ile Cys Lys Asn
1 5 10 15

( 2 ) INFORMATION FOR SEQ ID NO: 14:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 14:

ACT GGC GAA GGT ACT CCA AAG CCA CAA TCC CAC AAC GAT GGT GAC 45
Thr Gly Glu Gly Thr Pro Lys Pro Gln Ser His Asn Asp Gly Asp
1 5 10 15

( 2 ) INFORMATION FOR SEQ ID NO: 15:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 15:

GTC ACC ATC GTT GTG GGA TTG TGG CTT TGG AGT ACC TTC GCC AGT 45
Asp Gly Asp Asn His Ser Gln Pro Lys Pro Thr Gly Glu Gly Thr
1 5 10 15

( 2 ) INFORMATION FOR SEQ ID NO: 16:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO: 16:

TTC GAG GAA ATT CCT GAA GAA TAC CTA CAA TAGTAAGCAT G 41
Phe Glu Glu Ile Pro Glu Glu Tyr Leu Gln
1 5 10

( 2 ) INFORMATION FOR SEQ ID NO: 17:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO: 17:

CTTACTA TTG TAG GTA TTC TTC AGG AAT TTC CTC GAA 37
Gln Leu Tyr Glu Glu Pro Ile Glu Glu Phe
1 5 10

( 2 ) INFORMATION FOR SEQ ID NO: 18:

( i ) SEQUENCE CHARACTERISTICS:
( A ) LENGTH: 94 base pairs
( B ) TYPE: nucleic acid
( C ) STRANDEDNESS: single
( D ) TOPOLOGY: linear ( x i ) SEQUENCE DESCRIPTION: SEQ ID NO: 18:

```
AGCTTC ATG ATC CTC AAG ACC TTC CCG AAG TTC CTG GCT GCG GTC CTT    48
       Met Ile Leu Lys Thr Phe Pro Lys Phe Leu Ala Ala Val Leu
       1               5                   10

GCT CTC TCA CTG ACG GCG GCA CTC CCC CCA CTG TTC CCG GCC TGCA      94
Ala Leu Ser Leu Thr Ala Ala Leu Pro Pro Leu Phe Pro Ala
15                  20                  25
```

( 2 ) INFORMATION FOR SEQ ID NO: 19:

( i ) SEQUENCE CHARACTERISTICS:
( A ) LENGTH: 89 base pairs
( B ) TYPE: nucleic acid
( C ) STRANDEDNESS: single
( D ) TOPOLOGY: linear ( x i ) SEQUENCE DESCRIPTION: SEQ ID NO: 19:

```
GGC CGG GAA CAG TGG GGG GAG TGC CGC CGC CGT CAG TGA GAG AGC AAG   48
Ala Pro Phe Leu Pro Pro Leu Ala Ala Thr Leu Ser Leu Ser Ala Leu
1               5                   10                  15

GAC CGC AGC CAG GAA CTT CGG GAA GGT CTT GAG GAT CAT GA            89
Val Ala Ala Leu Phe Lys Pro Phe Thr Lys Leu Ile Met
            20                  25
```

( 2 ) INFORMATION FOR SEQ ID NO: 20:

( i ) SEQUENCE CHARACTERISTICS:
( A ) LENGTH: 202 base pairs
( B ) TYPE: nucleic acid
( C ) STRANDEDNESS: single
( D ) TOPOLOGY: linear ( x i ) SEQUENCE DESCRIPTION: SEQ ID NO: 20:

```
GTG GTT TAT ACG GAC TGT ACC GAA AGC GGT CAG AAC CTC TGC CTG TGC   48
Val Val Tyr Thr Asp Cys Thr Glu Ser Gly Gln Asn Leu Cys Leu Cys
1               5                   10                  15

GAG GGC TCG AAC CTC TGC GGA CAG GGG AAT AAG TGC ATC CTT GGA TCG   96
Glu Gly Ser Asn Val Cys Gly Gln Gly Asn Lys Cys Ile Leu Gly Ser
            20                  25                  30

GAC GGA GAG AAG AAT CAG TGC GTA ACC GGC GAG GGG ACA CCA AAG CCC  144
Asp Gly Glu Lys Asn Gln Cys Val Thr Gly Glu Gly Thr Pro Lys Pro
        35                  40                  45

CAA TCC CAC AAC GAC GGC GAT TTC GAG GAG ATA CCC GAG GAA TAC CTG  192
Gln Ser His Asn Asp Gly Asp Phe Glu Glu Ile Phe Glu Glu Tyr Leu
    50                  55                  60

CAA TGATGAG                                                      202
Gln
65
```

( 2 ) INFORMATION FOR SEQ ID NO: 21:

( i ) SEQUENCE CHARACTERISTICS:
( A ) LENGTH: 206 base pairs
( B ) TYPE: nucleic acid
( C ) STRANDEDNESS: single
( D ) TOPOLOGY: linear ( x i ) SEQUENCE DESCRIPTION: SEQ ID NO: 21:

```
GATCCTCATCA TTG CAG GTA TTC CTC GGG TAT CTC CTC GAA ATC GCC GTC   50
            Gln Leu Tyr Glu Glu Phe Ile Glu Glu Phe Asp Gly Asp
```

-continued

```
                    1                    5                         10

GTT  GTG  GGA  TTG  GGG  CTT  TGG  TGT  CCC  CTC  GCC  GGT  TAC  GCA  CTG  ATT     98
Asn  His  Ser  Gln  Pro  Lys  Pro  Thr  Gly  Glu  Gly  Thr  Val  Cys  Gln  Asn
      15                       20                        25

CTT  CTC  TCC  GTC  CGA  TCC  AAG  GAT  GCA  CTT  ATT  CCC  CTG  TCC  GCA  GAC    146
Lys  Glu  Gly  Asp  Ser  Gly  Leu  Ile  Cys  Lys  Asn  Gly  Gln  Gly  Cys  Val
 30                        35                        40                        45

GTT  CGA  GCC  CTC  GCA  CAG  GCA  GAG  GTT  CTG  ACC  GCT  TTC  GGT  ACA  GTC    194
Asn  Ser  Gly  Glu  Cys  Leu  Cys  Leu  Asn  Gln  Gly  Ser  Glu  Thr  Cys  Asp
                     50                        55                        60

CGT  ATA  AAC  CAC                                                                206
Thr  Tyr  Val  Val
                65
```

( 2 ) INFORMATION FOR SEQ ID NO: 22:

( i ) SEQUENCE CHARACTERISTICS:
( A ) LENGTH: 563 base pairs
( B ) TYPE: nucleic acid
( C ) STRANDEDNESS: single
( D ) TOPOLOGY: linear ( x i ) SEQUENCE DESCRIPTION: SEQ ID NO: 22:

```
AAGCTTCGCG  CCGCATGAGG  GGCTGAAGAA  AAAAATCTCT  CGATTGACAA                        50

ATTCATGCTC  GAATTTACAA  TGATCTTGTA  GAAAATCAAC  ATAAGGGCCA                       100

TGCATTTTTT  AGACCGATAT  CGTTATCGGT  TTGGAAAACA  ACCCCGGTAT                       150

CTCTTAGGAG  ACGCCGGGGT  TGTTCGCTTT  AAAGGGGGTG  ATCCATGGAA                       200

GCCGGATCAA  ACGACAAAAT  GTAAGCGTTT  CATTTTTTCA  CAGACACTTA                       250

GGAAGCAGGA  GGAC  ATG  ATA  TTG  AAA  ACA  TTC  CCG  AAA  TTT  CTT               294
                  Met  Ile  Leu  Lys  Thr  Phe  Pro  Lys  Phe  Leu
                   1                   5                        10

GCA  GCC  GTT  CTT  GCA  TTG  TCG  CTG  ACC  GCA  GCC  CTG  CCC  CCG              336
Ala  Ala  Val  Leu  Ala  Leu  Ser  Leu  Thr  Ala  Ala  Leu  Pro  Pro
                     15                       20

CTT  TTG  CCG  GCG  GTT  GTT  TAC  ACC  GAC  TGT  ACC  GAA  TCT  GGT              378
Leu  Leu  Pro  Ala  Val  Val  Tyr  Thr  Asp  Cys  Thr  Glu  Ser  Gly
 25                        30                        35

CAA  AAC  TTG  TGT  TTA  TGT  GAA  GGT  TCT  AAC  GTC  TGC  GGT  CAG              420
Gln  Asn  Leu  Cys  Leu  Cys  Glu  Gly  Ser  Asn  Val  Cys  Gly  Gln
      40                        45                        50

GGT  AAC  AAG  TGT  ATC  TTG  GGT  TCT  GAC  GGT  GAA  AAA  AAT  CAA              462
Gly  Asn  Lys  Cys  Ile  Leu  Gly  Ser  Asp  Gly  Glu  Lys  Asn  Gln
           55                        60                        65

TGT  GTC  ACT  GGC  GAA  GGT  ACT  CCA  AAG  CCA  CAA  TCC  CAC  AAC              504
Cys  Val  Thr  Gly  Glu  Gly  Thr  Pro  Lys  Pro  Gln  Ser  His  Asn
                70                        75                        80

GAT  GGT  GAC  TTC  GAG  GAA  ATT  CCT  GAA  GAA  TAC  CTA  CAA                   543
Asp  Gly  Asp  Phe  Glu  Glu  Ile  Pro  Glu  Glu  Tyr  Leu  Gln
                     85                       90

TAGTAAGCAT  GCAAGCTTGG                                                           563
```

( 2 ) INFORMATION FOR SEQ ID NO: 23:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO: 23:

-continued

TCATTCGTTC AAGGTACCCG GGGATCCGGG CCCTGTTAGA 40

( 2 ) INFORMATION FOR SEQ ID NO: 24:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO: 24:

GTCGGTGTAA ACAACTCTCT TATCCAAAGA TACACCTTGA ACGAATGA 48

( 2 ) INFORMATION FOR SEQ ID NO: 25:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO: 25:

TCATTCGTTC AAGGTGTATCT TTGGATAAG AGAGTTTACA CCGAC 45

( 2 ) INFORMATION FOR SEQ ID NO: 26:

( i ) SEQUENCE CHARACTERISTICS:
( A ) LENGTH: 13 amino acids
( B ) TYPE: amino acids
( C ) TOPOLOGY: linear ( x i ) SEQUENCE DESCRIPTION: SEQ ID NO: 26:

Ser Phe Val Gln Gly Val Ser Leu Asp Lys Arg Val Val
1 5 10

( 2 ) INFORMATION FOR SEQ ID NO: 27:

( i ) SEQUENCE CHARACTERISTICS:
( A ) LENGTH: 195 base pairs
( B ) TYPE: nucleic acid
( C ) STRANDEDNESS: single
( D ) TOPOLOGY: linear ( x i ) SEQUENCE DESCRIPTION: SEQ ID NO: 27:

GTTGTTTACA CCGACTGTAC CGAATCTGGT CAAAACTTGT GTTTATGTGA 50

AGGTTCTAAC GTCTGCGGTC AGGGTAACAA GTGTATCTTG GGTTCTRACG 100

GTGAAAAAAA TCAATGTGTC ACTGGCGAAG GTACTCCAAA GCCACAATCC 150

CACAACGATG GTGACTTCGA GGAAATTCCT GAAGAATACC TACAA 195

( 2 ) INFORMATION FOR SEQ ID NO: 28:

( i ) SEQUENCE CHARACTERISTICS:
( A ) LENGTH: 195 base pairs
( B ) TYPE: nucleic acid
( C ) STRANDEDNESS: single
( D ) TOPOLOGY: linear ( x i ) SEQUENCE DESCRIPTION: SEQ ID NO: 28:

GTGGTTTATA CGGACTGTAC CGAAAGCGGT CAGAACCTCT GCCTGTGCGA 50

GGGCTCGAAC GTCTGCGGAC AGGGGAATAA GTGCATCCTT GGATCGGACG 100

GAGAGAAGAA TCAGTGCGTA ACCGGCGAGG GGACACCAAA GCCCCAATCC 150

CACAACGACG GCGATTTCGA GGAGATACCC GAGGAATACC TGCAA 195

-continued ( 2 ) INFORMATION FOR SEQ ID NO: 29:

( i ) SEQUENCE CHARACTERISTICS:
( A ) LENGTH: 84 base pairs
( B ) TYPE: nucleic acid
( C ) STRANDEDNESS: single
( D ) TOPOLOGY: linear ( x i ) SEQUENCE DESCRIPTION: SEQ ID NO: 29:

```
ATGATCCTCA AGACCTTCCC GAAGTTCCTG GCTGCGGTCC TTGCTCTCTC    50
ACTGACGGCG GCACTCCCCC CACTGTTCCC GGCC                    84
```

( 2 ) INFORMATION FOR SEQ ID NO: 30:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO: 30:

```
TCATTCGTTC AAGGTGTATC TTTGGATAAG AGA    33
```

( 2 ) INFORMATION FOR SEQ ID NO: 31:

( i ) SEQUENCE CHARACTERISTICS:
( A ) LENGTH: 528 base pairs
( B ) TYPE: nucleic acid
( C ) STRANDEDNESS: single
( D ) TOPOLOGY: linear ( x i ) SEQUENCE DESCRIPTION: SEQ ID NO: 31:

```
CTCGAGGCCT GCATTGTCAC GAGAACATTG AAACATATAC AAAAAACAAA    50
TTTGAAATAG AAAACAAAGA ATTTACAGAA ATGACTGCCT GGTGCTAATT   100
CTTGCATATA TTTTATTTTT AATTAACTAG AAATCAGCGT CAATTATAGT   150
TTCTGGTGAG TCAGCCAATG TCTGTAAATA AAAACAATAT GCTTAATTAA   200
GAGGATTAAC AGTGGCACAA GAGGCAAAGA AGGGAAGAAG GCGTACACGT   250
CACATGAATA TATAAAAAGA AGAGGTTACA TCAATTGGAC CATCTTCGAC   300
GTTTCTATCT GCTACAAGCC TGTGTCGCCG AATTACTTTA TTGGGTCTTG   350
TAGAGACGCC GAAATACATC ATCATTCCAA GATCGACGAT AAAATCATCC   400
AAAAATTGTT GCCGAAAAAA AAATTGGAAA AGGTGAAAAA AAAATCAAAA   450
TACGGGTAAA CGAGCAATCC CTGTTCGGTG CGGTGATTGG CTTGAGGCAA   500
AGAGGTGTTA TAGGAACGCA GATCCAAA                           528
```